(12) United States Patent
Wood et al.

(10) Patent No.: US 10,172,362 B2
(45) Date of Patent: Jan. 8, 2019

(54) BIOFILMS, COMPONENTS AND METHODS OF USE TO REDUCE BIOFOULING AND CONTAMINATION

(71) Applicant: THE PENN STATE RESEARCH FOUNDATION, University Park, PA (US)

(72) Inventors: Thomas K. Wood, Port Matilda, PA (US); Manish Kumar, State College, PA (US); Thammajun L. Wood, Port Matilda, PA (US)

(73) Assignee: The Penn State Research Foundation, University Park, PA (US)

(*) Notice: Subject to any disclaimer, the term of this patent is extended or adjusted under 35 U.S.C. 154(b) by 0 days.

(21) Appl. No.: 15/334,168

(22) Filed: Oct. 25, 2016

(65) Prior Publication Data
US 2017/0112136 A1  Apr. 27, 2017

Related U.S. Application Data

(60) Provisional application No. 62/246,452, filed on Oct. 26, 2015.

(51) Int. Cl.
| | |
|---|---|
| C07K 14/21 | (2006.01) |
| C07K 14/245 | (2006.01) |
| A01N 63/02 | (2006.01) |
| C12N 9/02 | (2006.01) |
| C12N 9/10 | (2006.01) |
| C12N 9/14 | (2006.01) |
| C12N 1/00 | (2006.01) |
| C12N 1/04 | (2006.01) |
| C12N 15/70 | (2006.01) |
| C12N 15/74 | (2006.01) |
| C12N 15/78 | (2006.01) |
| C12R 1/01 | (2006.01) |

(52) U.S. Cl.
CPC .............. *A01N 63/02* (2013.01); *C07K 14/21* (2013.01); *C07K 14/245* (2013.01); *C12N 1/00* (2013.01); *C12N 1/04* (2013.01); *C12N 9/0075* (2013.01); *C12N 9/1029* (2013.01); *C12N 9/14* (2013.01); *C12N 15/70* (2013.01); *C12N 15/74* (2013.01); *C12N 15/78* (2013.01); *C12R 1/01* (2013.01); *C12Y 114/13039* (2013.01); *C12Y 203/01184* (2013.01); *C12Y 303/02003* (2013.01)

(58) Field of Classification Search
None
See application file for complete search history.

(56) References Cited

U.S. PATENT DOCUMENTS

| 6,723,321 B2 | 4/2004 | Greenberg et al. |
| 2004/0152660 A1 | 8/2004 | Cronan, Jr. et al. |
| 2009/0214674 A1* | 8/2009 | Barraud .............. A01N 59/00 424/718 |
| 2010/0011456 A1* | 1/2010 | Mathur .................. C12N 9/00 800/15 |
| 2010/0292261 A1 | 11/2010 | Yoon et al. |
| 2014/0142156 A1 | 5/2014 | Blackwell et al. |

OTHER PUBLICATIONS

Hong et al. 2012 (Synthetic quorum-sensing circuit to control consortial biofilm formation and dispersal in a microfluidic device; Nature Communications 3(613): 1-8) (Year: 2012).*
Herzberg et al. 2007 (Biofouling of reverse osmosis membranes: Role of biofilm enhanced osmotic pressure; Journal of Membrane Science 295: 11-20) (Year: 2007).*
Gusarov et al. 2008 (Bacterial Nitric-oxide Synthases Operate without a Dedicated Redox Partner; Journal of Biological Chemistry 283(9):13140-19164). (Year: 2008).*
Loo et al. 2006 (Diversity and Biocatalytic Potential of Epoxide Hydrolases Identified by Genome Analysis; Applied and Environmental Microbiology, 72(4): 2905-2917) (Year: 2006).*
Crane et al. 2010 (Bacterial Nitric Oxide Synthases; Annu. Rev. Biochem. 79:445-70) (Year: 2010).*
Parsek et al. 2005 (Sociomicrobiology: the connections between quorum sensing and biofilms; Trends in Microbiology 13(1): 27-33) (Year: 2005).*
Li et al. 2007 (Quorum Sensing in *Escherichia coli* Is signaled by Ai-2/LsrR: Effects on small RNA and Biofilnn Architecture; Journal of Bacteriology 189(16): 6011-6020); (Year: 2007).*
Ma et al. 2011 (*Escherichia coli* BdcA controls biofilm dispersal in Pseudomonas aeruginosa and Rhizobium meliloti; BMC Research Notes 4:447); (Year: 2011)*
Steindler et al. 2009 (LasI/R and RHII/R quorum sensing in a strain of Pseudomonas aeruginosa beneficial to plants; Applied and Environmental Microbiology 75(15):5131-5140). (Year: 2009).*
Barraud, Nicolas, et al. "Nitric Oxide Signaling in Pseudomonas Aeruginosa Biofilms Mediates Phosphodiesterase Activity, Decreased Cyclic Di-GMP Levels, and Enhanced Dispersal", Journal of Bacteriology, Dec. 2009, vol. 191, No. 23, pp. 7333-7342.
Geske, Grant D., et al. "Modulation of Bacterial Quorum Sensing with Synthetic Ligands: Systematic Evaluation of N-Acylated Homoserine Lactones in Multiple Species and New Insights into their Mechanisms of Action" J Am Chem Soc. (Nov. 7, 2007), 129 (44), pp. 13613-13625.
Gusarov, Ivan, et al. "Bacterial Nitric-Oxide Synthases Operate without a Dedicated Redox Partner" The Journal of Biological Chemistry, May 9, 2008, vol. 283, No. 19, pp. 13140-13147.

(Continued)

*Primary Examiner* — Mary Maille Lyons
(74) *Attorney, Agent, or Firm* — McKee, Voorhees & Sease, PLC

(57) ABSTRACT

Biofilms are provided which are capable of regulating their own thickness, reducing contamination and preventing biofouling. Constructs are introduced into bacteria that comprise nucleic acid molecules encoding an autoinducer synthase polypeptide, a transcriptional regulator and a biofilm dispersal protein. Nucleic acid molecules may also be introduced which encode a nitric oxide synthase, an epoxide hydrolase, or both. Biofilms of the bacteria may be used to reduce biofouling and contamination of a surface.

10 Claims, 41 Drawing Sheets
(28 of 41 Drawing Sheet(s) Filed in Color)

Specification includes a Sequence Listing.

(56) References Cited

OTHER PUBLICATIONS

Hong, Seok Hoon, et al. "Synthetic Quorum-Sensing Circuit to Control Consortial Biofilm Formation and Dispersal in a Microfluidic Device", Nature Communications, Published Jan. 3, 2012, 8 pages.
Kaplan, J.B., "Biofilm Dispersal: Mechanisms, Clinical Implications, and Potential Therapeutic Uses" J. Dent Res. (2010) 89 (3) pp. 205-218.
Kim, Sejin, et al. "Biofouling of Reverse Osmosis Membranes: Microbial Quorum Sensing and Fouling Propensity", Desalination (2009) 247, pp. 303-315.
Kulesekara, Hemantha, et al., "Analysis of Pseudomonas Aeruginosa Diguanylate Cyclases and Phosphodiesterases Reveals a Role for Bis-(3'-5')-cyclic-GMP in Virulence", PNAS (Feb. 21, 2016) vol. 103, No. 8, pp. 2839-2844.
Lee, Vincent T., et al. "A Cyclic-di-GMP Receptor Required for Bacterial Exopolysaccharide Production", Molecular Microbiology (2007) 65 (6), pp. 1474-1484.
Ma, Qun, et al., "*Escherichia coli* BdcA Controls Biofilm Dispersal in Pseudomonas Aeruginosa and Rhizobium Meliloti", BMC Research Notes (2011) 4: 447.
Ma, Qun, et al. "Engineering a Novel c-di-GMP-Binding Proteing for Biofilm Dispersal", Environ Microbiol (2011) 13(3), pp. 631-642.
Nakhamchik, Alina, et al. "Cyclic-di-GMP Regulates Extracellular Polysaccharide Production, Biofilm Formation, and Rugose Colony Development by Vibrio Vulnificus" Applied and Environmental Microbiology, (Jul. 2008), pp. 4199-4209.
Pesci, Everett C., et al. "Regulation of las and rhl Quorum Sensing in Pseudomonas Aeruginosa", Journal of Bacteriology (May 1997), vol. 179, No. 10, pp. 3127-3132.
Petrova, Olga E., et al. "Dispersion by Pseudomonas Aeruginosa Requires and Unusual Posttranslational Modification of BdIA", PNAS, Oct. 9, 2012, vol. 109, No. 41, pp. 16690-16695.
Ross, Peter, et al., "The Cyclic Diguanylic Acid Regulatory System of Cellulose Synthesis in Acetobacter Xylinum", The Journal of Biological Chemistry, (1990) vol. 265, No. 31, pp. 18933-18943.
Rui, Lingyum, et al., "Active Site Engineering of the Epoxide Hydrolase from Agrobacterium Radiobacter AD1 to Enhance Aerobic Mineralization of cis-1,2-Dichloroethylene in Cells Expressing an Evolved Toluene ortho-Monooxygenase", The Journal of biological Chemisty, (2004) vol. 279, No. 45, pp. 46810-46817.
Shrout, Joshua D., et al. "Monitoring Bacterial Twitter: Does Quorum Sensing Determine the Behavior of Water and Wastewater Treatment Biofilms?", Enviro. Sci. Technol. (2012), 46, pp. 1995-2005.
Siddiqui, Muhammad Faisal, et al., "Targeting N-acyl-homoserine-lactones to Mitigate Membrane Biofouling Based on Quorum Sensing using a Biofouling Reducer", Journal of Biotechnology (2012) 161, pp. 190-197.

Williams, Paul, et al., "Quorum Sensing and Environmental Adaptation in Pseudomonas Aeruginosa: a Tale of Regulatory Networks and Multifunctional Signal Molecules", Microbiology (2009), 12, pp. 182-191.
Wood, Thammajun, et al., "Living Biofouling-Resistant Membranes as a Model for the Beneficial Use of Engineered Biofilms", PNAS, May 2, 2016, 10 pages.
The Penn State Research Foundation, Application No. PCT/US2016/058701, filed Oct. 25, 2016, "The International Search Report and The Written Opinion of the International Searching Authority, or the Declaration", dated Jan. 27, 2017, 15 pages.
Castillo-Juarez, Israel, et al., "Exploiting Quorum Sensing Inhibition for the Control of Pseudomonas Aeruginosa and Acinetobacter Baumannii Biofilms", Bentham Science Publishers, (2016) 15 pages.
Castillo-Juarez, Israel, et al., "Role of Quorum Sensing in Bacterial Infections", World Class Journal of Clinical Cases (Jul. 16, 2015) 3(7) pp. 575-598.
Defoirdt, Tom, et al., "The Natural Furanone (5Z)-4-bromo-5-(bromomethylene)-3-butyl-2(5H)-Furanone Disrupts Quorum Sensing-Regulated Gene Expression in Vibrio harveyi by Decreasing the DNA-Binding Activity of the Transcriptional Regulator Protein LuxR", Environmental Microbiology (2007) 9(10), pp. 2486-2495.
Garcia-Contreras, Rodolfo, et al., "Quorum Sensing Enhancement of the Stress Response Promotes Resistance to Quorum Quenching and Prevents Social Cheating", The ISME Journal (2015) 9, pp. 115-125.
Gonzalez Barrios, Andres, et al., "Autoinducer 2 Controls Biofilm Formation in *Escherichia coli* Through a Novel Motility Quorum-Sensing Regulator (MqsR, B3022)", Journal of Bacteriology (Jan. 2006), vol. 188, No. 1, pp. 305-316.
Jayaraman, Arul, et al., "Bacterial Quorum Sensing: Signals, Circuits, and Implications for Biofilms and Disease", Annu. Rev. Biomed. Eng. (2008) 10: pp. 145-167.
Lee, Jintae, et al., "Reconfiguring the Quorum-Sensing Regulator SdiA of *Escherichia coli* to Control Biofilm Formation Via Indole and N-Acylhomoserine Lactones", Applied and Environmental Microbiology (Mar. 2009) vol. 75, No. 6, pp. 1703-1716.
Li, Jun, et al. "Quorum Sensing in *E coli* is Signaled by AI-2/LsrR: Effects on sRNA and Biofilm Architecture", American Society for Microbiology, published Jun. 8, 2007, 35 pages.
Maeda, Toshinari, et al., "Quorum Quenching Quandary: Resistance to Antivirulence Compounds", The ISME Journal (2012)6: pp. 493-501.
Ren, D. et al., "Gene Expression in *Escherichia coli* Biofilms", Appl. Microbiol. Biotechnol. (2004) 64: pp. 515-524.
Ueda, Akihiro, et al., "Connecting Quorum Sensing, c-di-GMP, Pel Polysaccharide, and Biofilm Formation in Pseudomonas Aeruginosa Through Tyrosine Phosphatase TpbA (PA3885)", PLOS, published Jun. 19, 2009, 18 pages.

\* cited by examiner

BIOFILMS, COMPONENTS AND METHODS OF USE TO REDUCE BIOFOULING AND CONTAMINATION

CROSS-REFERENCE TO RELATED APPLICATION

This application claims priority to previously filed and co-pending provisional application U.S. Ser. No. 62/246,452, filed Oct. 26, 2015, the contents of which are incorporated herein by reference.

GRANT REFERENCE

This invention was made with government support under Grant No. CBET1402063, awarded by the National Science Foundation. The Government has certain rights in the invention.

SEQUENCE LISTING

The instant application contains a Sequence Listing which has been submitted electronically in ASCII format and is hereby incorporated by reference in its entirety. Said ASCII copy, ASCII copy, created on Oct. 24, 2016, is named PSU-Wood-P11527US01_ST25.txt and is 2,130 bytes in size.

BACKGROUND OF THE INVENTION

Water is vital for all forms of life and access to clean and safe water is essential to human survival[1] and continuing progress. In addition to satisfying the needs of the public, water also plays an important role in many sectors of the economy including manufacturing, agriculture, electric power generation and extraction of minerals and energy resources[2]. As the demand for fresh water increases worldwide, membrane technologies have emerged as cost-effective approaches to utilize lower-quality water sources including brackish water, seawater and recycled wastewater[3]. Reverse osmosis (RO) is one of leading technologies for removing salts and other soluble contaminants from water[4]. However, membrane fouling by bacterial biofilms has remained a persistent and unmet challenge for the membrane-based water purification systems[1]. Bacterial biofilms reduce membrane permeability and salt rejection, and modify membrane module hydrodynamics resulting in excessive pressure drops leading to increased energy consumption[5].

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
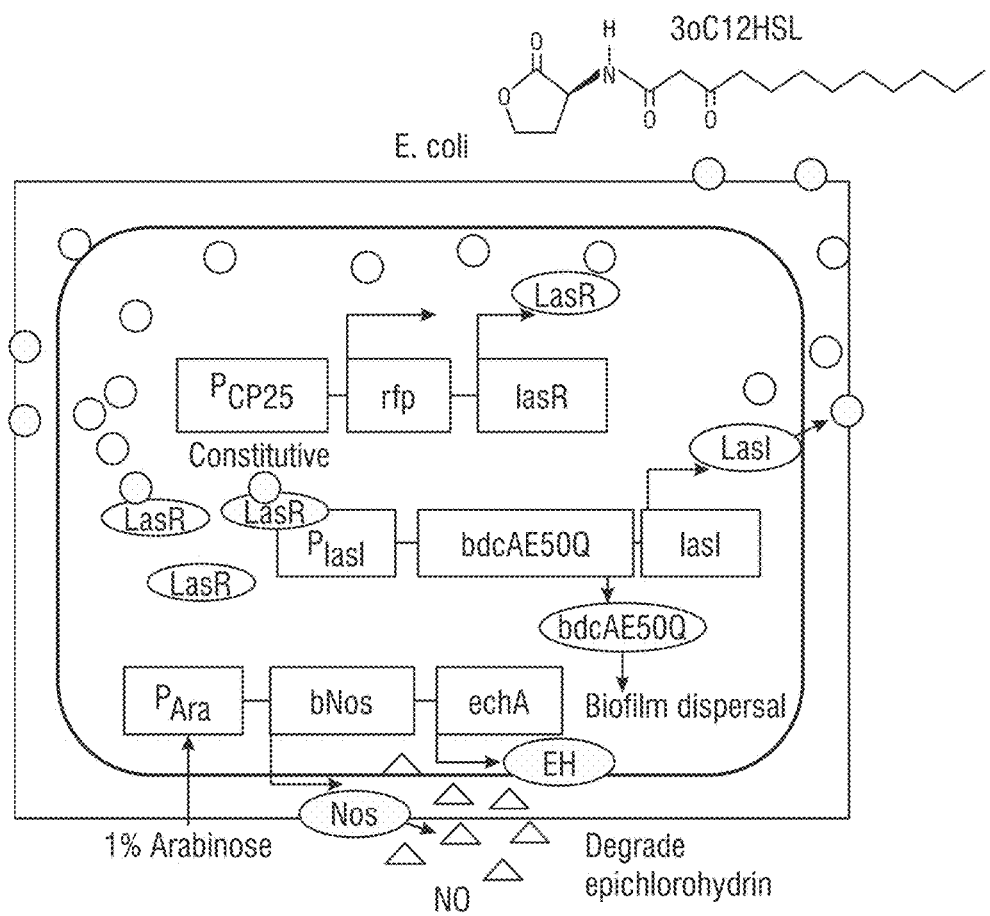
FIG. 1 is a graphic showing the self-controlled bacteria of an embodiment of the invention.

Nucleic acid constructs, bacteria, biofilms and methods are provided which result in decreased biofouling and which in an embodiment can degrade contaminants on a surface. The quorum sensing nucleic acid construct comprises a nucleic acid molecule which encodes an autoinducer synthase polypeptide, a transcriptional regulator and biofilm dispersal protein. A biofilm bacteria may be produced having the construct and which regulates its thickness. An embodiment provides that a nucleic acid sequence encoding nitric oxide synthase, a nucleic acid molecule encoding epoxide hydrolase, or both is introduced into the bacteria. The biofilm in an embodiment regulates its own thickness, prevents biofouling and degrades contaminants.

DETAILED DESCRIPTION OF THE INVENTION

The negative impact of biofouling of a surface has negative impacts in a variety of fields. For example, in reverse osmosis membrane systems, increasingly used for developing new water sources and recycling water, are a key technology to ensure water sustainability. However, as with all membrane water treatment processes, biofouling, the build-up of microbes and their polymeric matrix, clogs these systems and reduces their efficiency. Realizing that a microbial film is inevitable, an engineered beneficial biofilm is provided that prevents membrane biofouling by limiting its own thickness by sensing the number of its cells that are present via a quorum-sensing circuit; the beneficial biofilm also prevents biofilm formation by deleterious bacteria by secreting nitric oxide, a general biofilm dispersal agent. In addition, the beneficial biofilm was engineered to produce an epoxide hydrolase so that it efficiently removes the environmental pollutant epichlorohydrin. Provided here is a living reverse osmosis system that simultaneously reduces biofouling while providing a platform for biodegradation of persistent organic pollutants.

A biofilm is an aggregate of microorganisms which can be an aggregate of a single microorganism or multiple microorganisms (such as bacteria) attached to a surface and which can grow. In an embodiment, such microbial cells associated with a surface are enclosed in an extracellular polymeric substance matrix. An embodiment provides the matrix comprises polysaccharides. Bacterial biofilms are present in almost every flowing water environmental system[6], and they can play either beneficial (e.g., biocatalysis) or detrimental roles (e.g., biofouling) in many water and wastewater treatment systems[6]. There are several membrane biofouling control strategies including addition of disinfectants and biocides, influencing quorum sensing (QS) in biofilms and triggering their dispersion by adding specific molecules as dispersants[7], and membrane surface modification to reduce biofilm attachment and growth[8]. Quorum sensing, or cell-to-cell signaling plays a role in attachment and dispersal of biofilms to a surface. However, most current biofouling control techniques are either only initially effective due to the ability of the biofilm to adapt over time to the conditions imposed, or need repeated application to effectively control biofouling in the long run; hence, new methods are needed to control persistent biofouling.

One of the most prevalent biofouling strains in RO systems is *Pseudomonas aeruginosa* since it is ubiquitous in soil and water, and as a result, it has been isolated from biofilms on RO membranes[9]. *P. aeruginosa* is also used as a model bacterium for membrane fouling studies because of its ability to form biofilms and because the genetic basis of its biofilm formation is well-studied[10].

Temporal control of mixed-species biofilm formation and dispersal was achieved in a previous study using a synthetic gene circuit based on the LasI/LasR QS system of *P. aeruginosa* by combining it with the engineered Hha and BdcA biofilm dispersal proteins[11]. LasI/LasR is one of the best characterized QS systems in *P. aeruginosa*, and it plays a key role in controlling virulence factor production, swarming motility, biofilm maturation, and the expression of antibiotic efflux pumps[12]. Through this QS system, cells monitor their own cell density via exported signals produced by LasI; once a high cell density is reached, the signals diffuse back into the cells and activate genes by binding to the transcription regulator LasR. Gene circuits have not been used previously to impose self-regulation: control of biofilm formation and thickness by the strain producing the QS signal itself.

The final stage of biofilm formation is dispersal which contributes to survival and biofilm propagation in distant regions and thus contributes to disease transmission[13] by virulent strains, or in the case of engineered systems, performance degradation in distant parts of the system. Passive dispersal of cells from biofilms may be caused by fluid shear, abrasion, and grazing whereas active dispersal is caused by cell regulation[13]. Active dispersal may be triggered by changes in the environment including nutrient levels, oxygen, pH, and temperature and occurs under favorable and unfavorable conditions since both make sense for expanding the bacterial cellular population[13]. Upon these changes in the environment, active biofilm formation is regulated via quorum sensing cues like acylhomoserine lactones and 2-heptyl-3-hydroxy-4-quinolone[13], and biofilm dispersal is regulated by fatty acid signals like cis-2-decenoic acid[14], nitric oxide (NO)[15], and cyclic diguanylate (c-di-GMP)[16].

The secondary messenger c-di-GMP is ubiquitous in Gram negative bacteria and is synthesized by diguanylate cyclases and degraded by phosphodiesterases. Many proteins with GGDEF motifs enhance biofilm formation[17]; for example, c-di-GMP increases cellulose biosynthesis in *Acetobacter xylinus*[18], and c-di-GMP enhances extracellular polysaccharide production by binding the PelD protein that is a c-di-GMP receptor in *P. aeruginosa* PA14[19]. Gram negative bacteria includes bacterial which, when treated with Gram's Stain will stain pink, such as *E. coli* and *Pseudomonas* sp. Thus, biofilm formation and dispersal are controlled by a signal cascade mediated by c-di-GMP levels: high levels promote biofilm formation and low levels lead to reduced biofilm formation and increased dispersal. NO induces biofilm dispersal by enhancing the activity of phosphodiesterases resulting in the degradation of c-di-GMP[20]. NO is effective in dispersing a variety of different biofilms[15] including *P. aeruginosa* biofilms[20], and NO synthase (NOS) from *Bacillus anthracis* is active in *E. coli*[21]. Hence, NOS was used in one example to generate NO to disperse deleterious biofilms Epichlorohydrin is a common precursor for synthesizing glycerins, epoxy resins, elastomers, pesticides, textiles, membranes, paper, and pharmaceuticals[22]. As a water contaminant, epichlorohydrin harms the skin, liver, kidneys, and central nervous system, and is a potential carcinogen[23]. Epichlorohydrin also represents a class of environmental contaminants that have epoxide groups by design or where epoxide groups result from biological transformation of water pollutants such as pesticides and prescription drugs. Examples that are found in water supplies and in wastewater streams include aldrin epoxide[24], heptachlor epoxide[25], chlordane epoxide, and carbamazepine-10,11 epoxide[25]. Microsomal and soluble epoxide hydrolase (EH) present in mammalian systems play a major role in detoxifying these and other epoxide-containing xenobiotic compounds[26]. Epichlorohydrin is degraded by EH from *Agrobacterium radiobacter* AD1[27], and engineered variants of EH (F108L/1219L/C248I) enhance epichlorohydrin degradation six fold[28]; hence, engineered EH from this organism was used to degrade epichlorohydrin. Thus a wide range of epoxide based water pollutants can potentially also be detoxified using this biomimetic approach.

An embodiment provides, at least in part, the use of bacterial autoinducer synthase molecules and in an example, molecules that catalyze the synthesis of homoserine lactone autoinducers in an interaction of particular homoserine lactone substrates. This provided the capability to develop compositions and methods to modulate the quorum sensing capabilities of bacterial cells by controlling autoinducer production.

One embodiment pertains to methods that modulate the activity of an autoinducer synthase molecule by providing an effective amount of a compound that acts as a biofilm dispersal agent by binding cyclic diguanylate (c-di-GMP) which causes the cell to decrease production of biofilm adhesins. Autoinducer synthase molecules can be obtained from naturally occurring sources, e.g., by purifying cellular extracts, can be chemically synthesized or can be recombinantly produced. The manner of producing the molecules is not critical. Recombinantly produced autoinducer synthase molecules can have the amino acid sequence of a naturally occurring form of the autoinducer synthase protein. They can also have a similar amino acid sequence which include mutations such as substitutions and deletions (including truncation) of a naturally occurring form of the protein. Autoinducer synthase molecules can also include compounds which are structurally similar to the structures of naturally occurring autoinducer synthase proteins.

In referring to an autoinducer synthase molecule is intended to include molecules, e.g. proteins, which catalyze or facilitate the synthesis of autoinducer compounds, e.g. in the quorum sensing system of bacteria. It is also intended to include active portions of the autoinducer synthase protein contained in the protein or in fragments or portions of the protein. Reference to active portions is intended to include the portion of the autoinducer synthase protein which contains the homoserine lactone binding site. There are many bacterial autoinducer synthase molecules known and available to those of skill in the art, including LuxI, AinS, LucM, LasI, RhlI, PhzI, TraI, HslI, EsaI, EagI, YenI, SwrI, and AhyI. Such molecules and their production are readily available to one skilled in the art, see for example, U.S. Pat. No. 6,723,321, incorporated herein by reference in its entirety and in particular see Table 1 of the patent. In a preferred embodiment the autoinducer synthase is LasI.

According to an embodiment of the invention, a construct comprising an autoinducer synthase encoding polynucleotide operably linked to a transcriptional regulator (such as LasR) and further including a nucleotide sequence encoding a biodispersal protein (such as BdcA, Hha, or a phosphodiesterase), introduced to a bacteria cell. The polynucleotide produces an autoinducer (such as N-(3-oso-dodecanoyl)-L_homoserine lactone (3oC12HSL)) which accumulates as cell density increases and induces the formation of a biofilm dispersal protein, here BdcA, which limits the biofilm quantity and thus the thickness of the protective strain.

Thickness or biomass of the beneficial biofilm is in an embodiment capable of being reduced by at least up to two fold, three fold, four fold, five fold, six fold, seven fold, eight fold, nine fold, ten fold or more compared to a biofilm of bacteria not comprising the constructs and genetic circuit here described. Further, as discussed herein flux decline caused by uncontrolled fouling can be reduced by up to 10,%, 20%, 30%, 40%, 50%, 60%, 70%, 80%, 90% or more compared to flux decline caused by uncontrolled fouling where the biofilm does not comprise the constructs and genetic circuit here described. Further, sodium chloride rejection can be improved by up to 5%, 6,%, 7%, 8%, 9%, 10%, 11% or more compared to biofilm not comprising the constructs and genetic circuit here described.

To form a beneficial biofilm layer on RO membranes, the inventors developed a protective biofilm that does not attain a large thickness and that prevents the growth of other bacteria so that membrane permeability and salt rejection are maintained and pressure drops are minimized. Applicants devised a genetic circuit in which the bacterium senses its own presence to limit its biofilm formation (FIG. 1A). To accomplish this, the LasI/LasR quorum sensing system of *P. aeruginosa* is used to produce the autoinducer molecule N-(3-oxo-dodecanoyl)-L-homoserine lactone (3oC12HSL) signal which accumulates as the cell density increases and induces the formation of a biofilm dispersal protein, BdcA, which limits the biofilm quantity and thus thickness of the protective strain. In a preferred embodiment the BdcA E50Q variant is used as it causes six-fold higher levels of biofilm dispersal, but any BdcA E50Q variant may be used according to the invention.

In an example, the response regulator LasR is produced continuously and monitors the presence of QS signal 3oC12HSL produced by LasI; as the 3oC12HSL signal increases due to increasing cell density, additional 3oC12HSL signal is produced as LasR bound to 3oC12HSL activates lasI Increased production of the 3oC12HSL signal leads to activation of dispersal protein BdcA which leads to dispersal of the beneficial biofilm.

Applications of the invention include other membrane technologies such as membrane bioreactors and forward osmosis for contaminant degradation and biofouling prevention. The invention can also be extended to industrial and biomedical settings with proper controls on engineered biofilm proliferation. Additional industrial settings include biofilms in cooling towers, water distribution systems as well as in building HVAC systems (implicated in Legionnaires' disease). Biomedical applications include biofilm prevention in medical catheters, biomedical implants, and biofilm related human diseases such as cystic fibrosis, endocarditis, dental plaque, and chronic rhinosinusitis. The use of beneficial biofilms to combat biofilm related diseases can reduce the use of antibiotics and help combat the rise of antibiotic resistance.

In a preferred embodiment, the invention may be used in drought, water scarcity, and development of marginal water resources. Current droughts in California and the intense focus on seawater desalination and wastewater recycling all over the world have emphasized the need to develop more efficient water treatment technologies. RO is currently the best available technology for the ultimate removal of dissolved contaminants and is used widely in water treatment and wastewater recycling but suffers from performance degradation from biofouling. The proposed, easily scalable approach can be immediately applied to these systems to make them more sustainable.

Further embodiments include the addition of nucleic acids encoding that NO synthase as well as nucleic acids which encode an epoxide hydrolase to remove environmental pollutants such as epichlorohydrin.

The methods and engineered bacteria and biofilm are particularly useful where the surface is a Reverse Osmosis membrane. Reverse Osmosis (RO) membranes are being used to purify alternative sources of water such as recycled wastewater, brackish water and seawater. This technology is ideal as it can remove almost all substances dissolved in water including salt, microbial contaminants and organic contaminants. However, a major challenge to employing RO membranes is the increase in energy that accompanies fouling of these membranes. Fouling is the accumulation of unwanted material on solid surfaces to the detriment of function. The fouling material can consist of either living organisms (biological or biofouling) or a non-living substance (inorganic or organic). In particular, biological fouling caused by deposition and then growth of microbes in colonies known as biofilms, is a major challenge. Biofilms are difficult to prevent due to sensitivity of RO membranes to chemical disinfectants and once formed are extremely difficult to eradicate by current chemical cleaning methods. Here, the persistence of biofilms was used to turn the biofouling problem on its head by engineering biofilms that 1) control their own thickness and 2) release molecules (signals) that prevent colonization of this engineered biofilm by other microorganisms. This biofilm was also engineered to contribute to the removal of the contaminants that can pass through the RO membrane. In one embodiment instead of replacing membranes, they can be cleaned, such as with chlorination or the like, and reused, thus reducing costs considerably.

The ability to make bacteria dissolve deleterious biofilms by activating a series of genetic pathways (i.e., to secrete enzymes to remove the polymers that cement the bacteria in place and to make the bacteria swim away) has not been done previously for RO biofouling control. Therefore, an embodiment provides the use of metabolic engineering to create the first living membrane comprising RO membranes and a thin beneficial biofilm that both prevents biofouling as well as removes toxic wastes in water recovery systems. To control the extent of the beneficial biofilm dispersal, the diguanylate cyclase (c-di-GMP)-binding protein, BdcA, of *E. coli* was used. (See Ma et al. "*Escherichia coli* BdcA controls biofilm dispersal in *Pseudomonas aeruginosa* and *Thizobium eliloti*" BMC Research Notes 4:447 (2011).) The invention includes engineered BdcA to cause biofilm dispersal. By controlling BdcA production, the extent of biofilm formation by the beneficial biofilm is controlled. Pollutants were eliminated by incorporating contaminant-degrading enzymes in these beneficial biofilms. By controlling biofilms on RO membranes, chemicals required for disinfection and cleaning are eliminated and the overall power consumption of this critical water treatment technology is reduced. Further, the processes here are unique in using an engineered strain in a water purification system, where or not used with an RO membrane.

Quorum sensing (QS) is a process by which bacteria assess their population density through a language of low molecular weight signaling molecules (autoinducers). Gram-negative bacteria commonly use N-acylated homoserine lactones (AHLs) as their primary autoinducers and their respective receptors (R proteins) for QS. Assessing population density allows for the modulation of gene expression levels required for group behavior. Genes regulated by QS in *Pseudomonas aeruginosa* include virulence factor production and biofilm production. [Geske, G. D.; O'Neill, J. C.; Miller, D. M.; Mattmann, M. E.; Blackwell, H. E., Modulation of Bacterial Quorum Sensing: Systematic Evaluation of N-Acylated Homoserine Lactones in Multiple Species and New Insights into Their Mechanism of Action. *J. Am. Chem. Soc.* 2007, 129, 13613-13625.] At high cell densities, bacteria use this chemical signaling process to switch from a nomadic existence to that of multicellular community. This lifestyle switch is significant, as numerous pathogenic bacteria use quorum sensing to turn on virulence pathways and form drug-impervious communities called biofilms that are the basis of myriad chronic infections. Over 80% of bacterial infections in humans involve the formation of biofilms, as exemplified in lung infections by *Pseudomonas aeruginosa*, which is the primary cause of morbidity in cystic fibrosis patients. The treatment of infections by pathogens that form biofilms costs over $1 billion/year in the US alone. Biofilms are dense extracellular polymeric matrices in which the bacteria embed themselves. Biofilms allow bacteria to create a microenvironment that attaches the bacteria to the host surface and which contains excreted enzymes and other factors allowing the bacteria to evade host immune responses including antibodies and cellular immune responses. Such biofilms can also exclude antibiotics. Further, biofilms can be extremely resistant to removal and disinfection. For individuals suffering from cystic fibrosis, the formation of biofilms by *P. aeruginosa* is eventually fatal. Other bacteria also respond to quorum sensing signals by producing biofilms. Biofilms are inherent in dental plaques, and are found on surgical instruments, food processing and agriculture equipment and water treatment and power generating machinery and equipment. Any bacteria may be used which is capable of expressing the constructs and molecules described herein. In particular, by way of example, Gram negative bacteria such as *E. coli* are especially useful.

The present invention further provides a method for treating or preventing biofilm formation on a surface, the method comprising contacting said surface with one or more bacteria which have been genetically modified according to the invention. In an embodiment, the method further comprises contacting the surface with one or more bacteria of the invention.

When referring to introduction of a construct or nucleic acid molecule into a microorganism such as bacteria, is meant to include any convenient means of inserting the nucleic acid molecule into the host. Many such methods are known to a person skilled in the art and are continuing to be developed, and the methods described here are not limited to any particular method. By way of example without limitation, CaCl$_2$ incubation methods of Mandel and Higa, *J. of Mol. Biol.* 53:159 (1970), as well as numerous well-known variants thereof may be employed. Hanahan has made a detailed study of factors that affect the efficiency of transformation of *E. coli* cells (*J. Mol. Biol.* 166:557-580 (1983)) where he describes a method of producing *E. coli* cells comprising the step of washing *E. coli* cells in a buffer comprising potassium acetate, KCl, MnCl$_2$, CaCl$_2$, and hexamine cobalt chloride. Various methods of producing competent *E. coli* cells is described at U.S. Pat. Nos. 4,981,797, 5,707,841, and 6,756,220, incorporated herein by reference in their entirety. See also Hanahan, et al., "Studies on transformation of *Escherichia coli* with plasmids" *J. Mol. Biol.* 166:557-580 (1983) and Sambrook, et al. Molecular cloning: a laboratory manual, Third Edition, Cold Spring Harbor Laboratory Press, Cold Spring Harbor, N.Y. (2001).

Nucleic acid constructs comprising a nucleic acid sequence as described here, can be operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion. A nucleic acid construct is meant to include a nucleic acid molecule, either single- or double-stranded. The term nucleic acid construct is synonymous with the term expression cassette when the nucleic acid construct contains all the control sequences required for expression of a coding which directly specifies the amino acid sequence of its protein product.

The term control sequences is defined herein to include all components which are necessary or advantageous for the expression of a polypeptide. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term operably linked is defined herein as a configuration in which a control sequence is appropriately placed at a position relative to nucleic acid molecule such that the control sequence directs the expression of a polypeptide.

The control sequence may be an appropriate promoter sequence, a nucleic acid sequence which is recognized by a host cell for expression of the nucleic acid sequence. The promoter sequence may contain transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., *Proceedings of the National Academy of Sciences* USA 75: 3727-3731(1978)), as well as the tac promoter (DeBoer et al., *Proceedings of the National Academy of Sciences* USA 80: 21-25(1983)). The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used. Effective signal peptide coding regions for bacterial host cells include, by way of example without limitation, the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, *Microbiological Reviews* 57: 109-137 (1993).

The methods and components here also relate to recombinant expression vectors comprising a nucleic acid sequence as described, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors may contain one or more selectable markers which permit easy selection of transformed cells. Scorable or screenable markers are useful, where presence of the sequence produces a measurable product and can produce the product without destruction of the plant cell. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance.

A nucleic acid molecule (which may also be referred to as a polynucleotide) can be an RNA molecule as well as DNA molecule, and can be a molecule that encodes for a desired polypeptide or protein, but also may refer to nucleic acid molecules that do not constitute an entire gene, and where indicated, which do not necessarily encode a polypeptide or protein. If desired, the nucleotide sequence of interest can be optimized for translation by optimizing the codons used for bacteria and the sequence around the translational start site for bacteria. Sequences resulting in potential mRNA instability can also be avoided.

Unless otherwise indicated, a particular nucleic acid sequence also implicitly encompasses conservatively modified variants thereof (e.g. degenerate codon substitutions) and complementary sequences as well as the sequence explicitly indicated. The term conservatively modified variants applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide is implicit in each described polypeptide sequence and is within the scope of the products and processes described.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994).

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., see, e.g., Creighton, Proteins: Structures and Molecular Properties (WH Freeman & Co.; 2nd edition (December 1993)).

By encoding or encoded, with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons.

In an embodiment, the surface is a non-biological surface. In an embodiment, the surface is a natural surface. In an embodiment, the surface is a surface of a plant, seed, wood, fiber or hair. In an embodiment, the surface is a biological surface; preferably the surface is a surface of a tissue, membrane, or skin. In an embodiment, the surface is a hard surface; preferably the surface comprises a metal, an organic polymer, an inorganic polymer, a natural elastomer, a synthetic elastomer, glass, wood, paper, concrete, rock, marble, gypsum, or ceramic.

In an embodiment of this aspect, the surface is a soft surface, and may be the surface of a fiber comprising a yarn, a textile, a vegetable fiber, or rock wool. In another embodiment, the surface is a porous surface. In an embodiment, the surface is a surface of process equipment or components of cooling equipment. In a preferred embodiment, the process equipment is or is a component of a cooling tower, a water treatment plant, a dairy processing plant, a food processing plant, a chemical process plant, or a pharmaceutical process plant. In a preferred embodiment the surface is that of a filter or a membrane filter.

The following is provided by way of example and not intended to limit the scope of the invention. All references cited herein are incorporated herein by reference.

EXAMPLES

Here, a system is described to significantly reduce the biofouling of RO membranes while degrading an important class of contaminants. Specifically, we engineered a beneficial biofilm of *E. coli* via genetic circuits (i) to limit its biofilm formation, (ii) to prevent biofouling by deleterious bacteria such as *P. aeruginosa*, and (iii) to degrade the model environmental pollutant epichlorohydrin. To create these beneficial traits, a quorum sensing system, in this example, the LasI/LasR QS system of *P. aeruginosa* was fused to the engineered biofilm dispersal protein, here BdcA of *E. coli* to create the first self-controlled biofilm. Additionally, nitric oxide was generated in the beneficial biofilm by NO synthase from *B. anthracis* to prevent biofouling. We also demonstrate that epichlorohydrin (which passes through the RO membrane) is degraded by cloning the gene encoding EH from *A. radiobacter* AD1 into the beneficial biofilm.

RESULTS

Biofilm Formation is Limited in the Self-Controlled Strain. To form a beneficial biofilm layer on RO membranes, we desired a protective biofilm that does not attain a large thickness and that prevents the growth of other bacteria so that membrane permeability and salt rejection are maintained and pressure drops are minimized. Hence, a genetic circuit was devised in which the bacterium senses its own presence to limit its biofilm formation (FIG. 1). To accomplish this, we utilized the LasI/LasR quorum sensing system of *P. aeruginosa*[29] to produce the autoinducer molecule N-(3-oxo-dodecanoyl)-L-homoserine lactone (3oC12HSL) signal which accumulates as the cell density increases and induces the formation of a biofilm dispersal protein, BdcA[11], which limits the biofilm quantity and thus thickness of the protective strain. Specifically, the response regulator LasR is produced continuously and monitors the presence of QS signal 3oC12HSL produced by LasI; as the 3oC12HSL signal increases due to increasing cell density, additional 3oC12HSL signal is produced as LasR bound to 3oC12HSL activates lasI Increased production of the 3oC12HSL signal leads to activation of dispersal protein BdcA which leads to dispersal of the beneficial biofilm.

Figure 2:
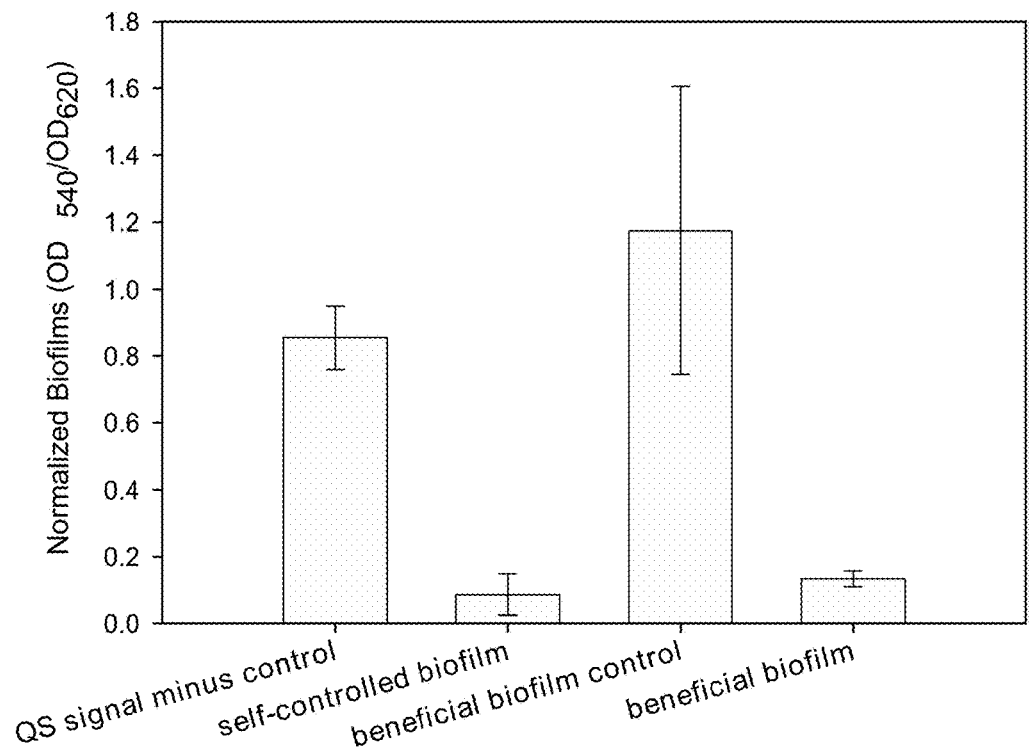
FIG. 2 is a graph showing results of assay of biofilm formation with a control film, a self-controlled film and the "beneficial self-controlled film additionally having a nitric oxide (NO) sequence where NO production is induced and not induced.

The resulting self-controlled biofilm strain is *E. coli* TG1/pBdcAE50Q-lasI-lasR (henceforth "self-controlled strain"); *E. coli* TG1/pBdcAE50Q-rfp-lasR[31], which lacks LasI (QS signal minus strain) was used as a negative control. To demonstrate that the self-controlled biofilm strain can self-regulate its biofilm, both a 96-well plate crystal violet biofilm assay and a confocal microscope biofilm assay were performed. For the 96-well plate assay, the self-controlled biofilm strain had approximately nine-fold less biofilm after 24 h compared to the QS signal minus control strain (FIG. 2). Normalized biofilm formation for the self-controlled biofilm (*E. coli* TG1/pBdcAE50Q-lasI-lasR) compared to the QS signal minus control (*E. coli* TG1/pBdcAE50Q-rfp-lasR) and for the beneficial biofilm strain (*E. coli* TG1/pBdcAE50Q-lasI-lasR/pBNos) compared to the beneficial biofilm strain without NO synthesis control (*E. coli* TG1/pBdcAE50Q-lasI-lasR/pBad). Biofilms were formed for 24 h at 37° C. in M9G with Cm (300 μg/mL), Cb (250 μg/mL), 1% arabinose, and 5 mM L-arginine.

This result was corroborated using confocal microscopy where after 2 days, the self-controlled biofilm was six fold less than the QS signal minus control strain (average biomass 0.6±0.6 μm$^3$/μm$^2$ vs. 3.5±1 μm$^3$/μm$^2$ and average thickness 1.5±1 μm vs. 7.6±2 μm, for the self-controlled and control biofilms, respectively, representative figures shown in FIG. 2). Therefore, using this gene circuit, biofilm formation was successfully controlled as a function of cell density using the biofilm dispersal protein BdcA under the control of a QS circuit.

In detail, see FIG. 1 (*a*) Gene circuit for the self-controlled biofilm strain. *E. coli* was engineered to limit its own biofilm formation using the LasI/LasR QS module of *P. aeruginosa*. The LasI protein and the engineered biofilm dispersal protein BdcA E50Q are controlled by the lasI promoter. When LasI is produced, it synthesizes the QS signal 3oC12HSL, and upon reaching a threshold value based on increasing cell density, the QS signal binds to LasR (which is constitutively produced via the CP25 promoter along with RFP to visualize the cells). The 3oC12HSL+LasR complex activates the lasI promoter which leads to increasing production of dispersal protein BdcA E50Q as cell density increases. The BNos and epoxide hydrolase are induced by adding arabinose. See FIG. 2 where biofilm formation is visualized with confocal microscopy on glass surfaces after 48 h for the QS signal minus control strain that lacks LasI (TG1/pBdcAE50Q-rfp-lasR) and the LasI/LasR self-controlled biofilm strain (TG1/pBdcAE50Q-lasI-lasR). Scale bar indicates 20 μm. LasI (control) vs. LasI/LasR biofilm values for these figures were 4.2 μm$^3$/μm$^2$ vs. 0.52 μm$^3$/μm$^2$ for average biomass and 9.11 μm vs. 1.18 μm for average thickness, respectively.

Figure 4A:
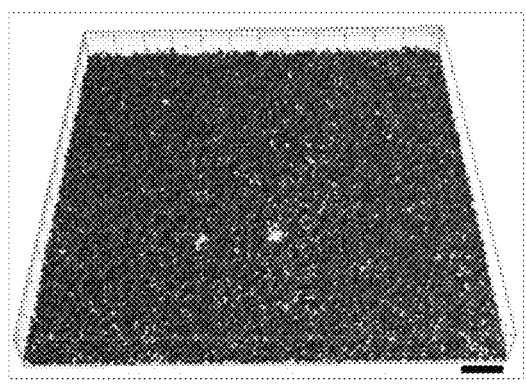
FIG. 4A-B are confocal microscopy visualizations of grown of uncontrolled biofilm (A) and self-controlled biofilm (B) on an RO membrane.
Figure 4B:
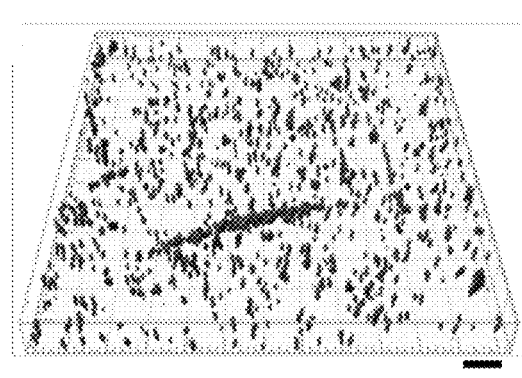
Figure 5A:
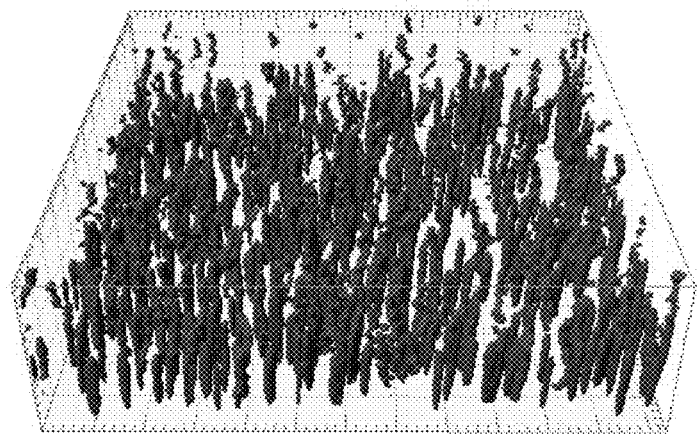
FIG. 5A-F are images of growth of biofilms on NF90 membranes.
Figure 5B:
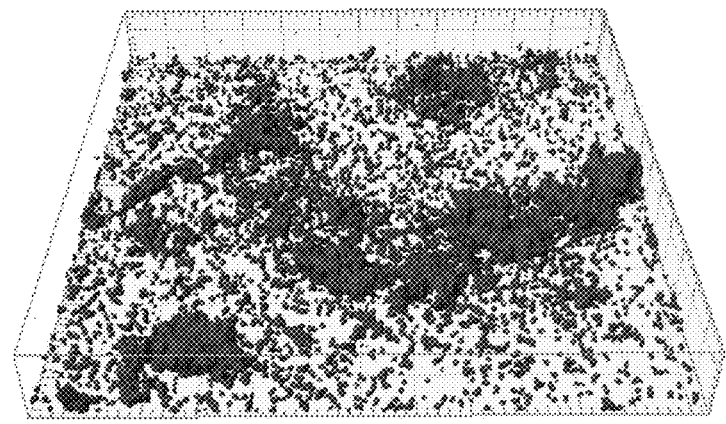
Figure 5C:
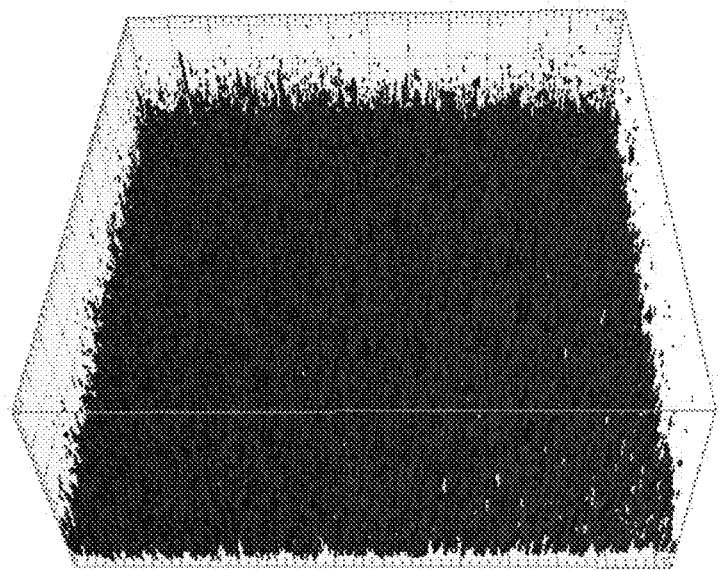
Figure 5D:
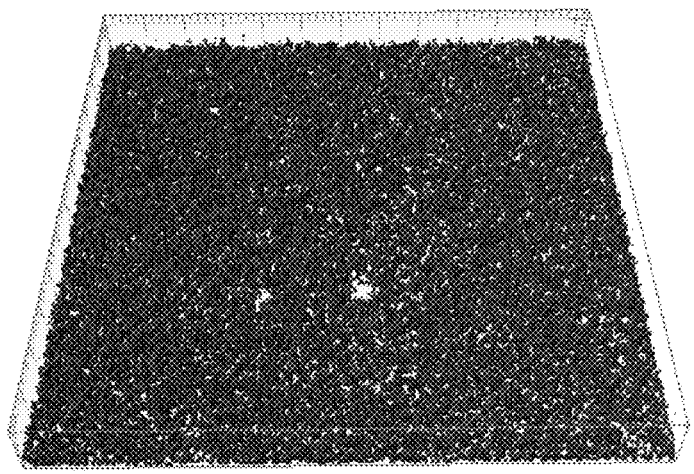
Figure 5E:
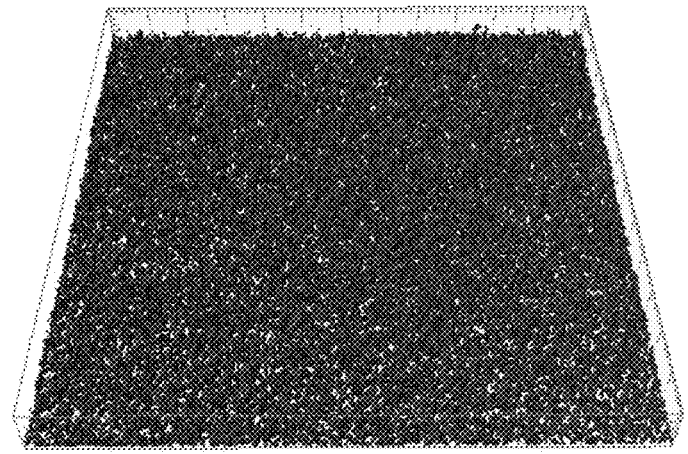
Figure 5F:
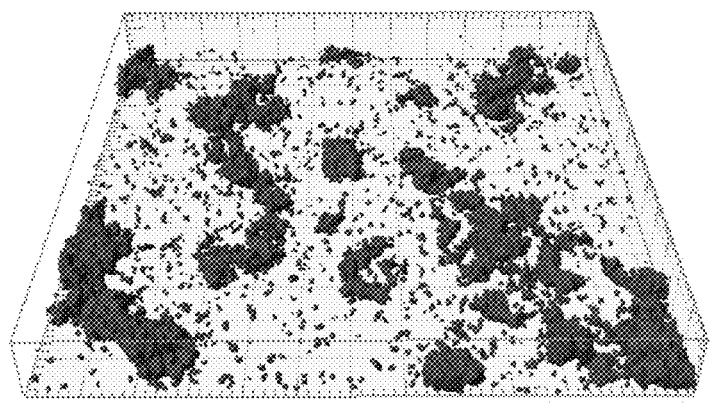

Permeate Flux is Increased with the Self-Controlled Biofilm. Biofilms of the self-controlled biofilm strain and the QS signal minus strains were grown on commercially available NF90 thin film composite (TFC) polyamide membranes as a representative of polyamide TFC RO membranes. The QS signal minus strain formed thick and more uniform biofilms over the polyamide NF90 membrane (FIGS. 4A and 4B) while the self-controlled strain developed considerably thinner and more heterogeneous biofilm with approximately 42-fold lower biomass amounts (0.2±0.1 μm$^3$/μm$^2$) than the QS signal minus control strain (8.4±7 μm$^3$/μm$^2$) (FIG. 7 and the table with referenced figures below). The figures show a 3D reconstruction of LasR (*E. coli* TG1/pBdcAE50Q-rfp-lasR) biofilm formation using IMARIS. The biofilms were grown on NF90 membranes in M9G medium with Cm (300 μg/mL) for 24 h at an initial OD$_{600\ nm}$ of 0.5. FIG. 5*a* is shown in FIG. 4. All the biomass and average thickness data were calculated using COMSTAT. Each major grid bar represents 20 μm.

TABLE 1

| FIG. | Biomass (μm$^3$/μm$^2$) | Average Thickness (μm) |
|---|---|---|
| 5A | 15.81 | 38.94 |
| 5B | 2.97 | 4.10 |
| 5C | 17.34 | 37.62 |
| 5D | 5.82 | 7.52 |
| 5E | 5.65 | 7.07 |
| 5F | 2.56 | 3.25 |
| Average | 8.36 | 16.42 |

Figure 6A:
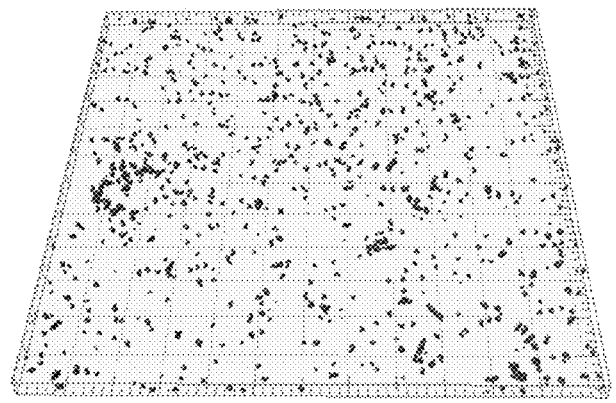
FIG. 6A-F are images of growth of biofilms on NF90 membranes
Figure 6B:
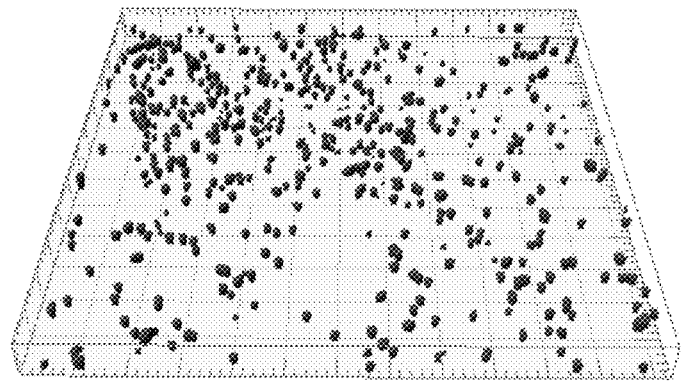
Figure 6C:
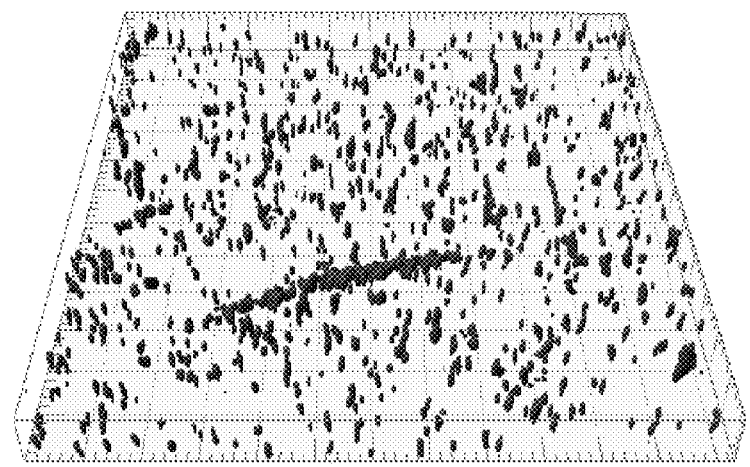
Figure 6D:
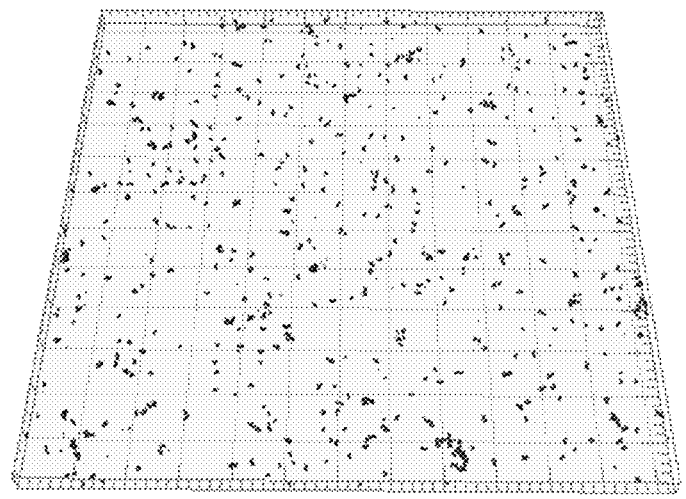
Figure 6E:
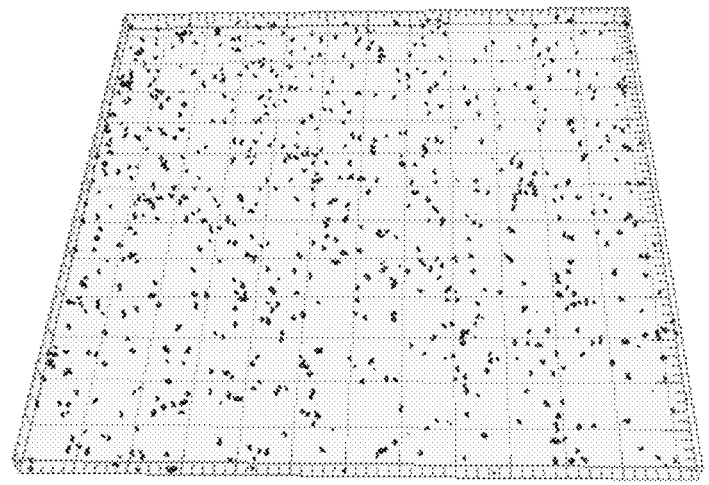
Figure 6F:
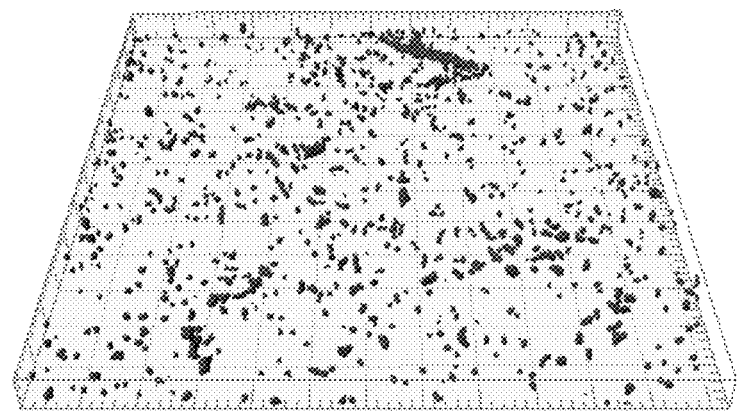

The figures referenced in Table 2 below show 3D reconstruction of LasI/LasR (*E. coli* TG1/pBdcAE50Q-lasI-lasR) biofilm formation using IMARIS. The biofilms were grown on NF90 membranes in M9G medium with Cm (300 μg/mL) for 24 h at an initial OD$_{600\ nm}$ of 0.5. FIG. 6C is shown in FIG. 4. All biomass and average thickness data were calculated using COMSTAT. Each major grid bar represents 20 μm.

TABLE 2

| FIG. | Biomass (μm$^3$/μm$^2$) | Average Thickness (μm) |
|---|---|---|
| 6A | 0.09 | 0.15 |
| 6B | 0.28 | 0.73 |
| 6C | 0.30 | 0.40 |
| 6D | 0.10 | 0.13 |
| 6E | 0.12 | 0.16 |
| 6F | 0.34 | 0.45 |
| Average | 0.20 | 0.34 |

In detail, see FIG. 4 for comparison of growth and resulting permeate fluxes for *E. coli* TG1/pBdcAE50Q-lasI-lasR (self-controlled strain) and *E. coli* TG1/pBdcAE50Q-rfp-lasR[31], which lacks LasI (QS signal minus strain) on NF90 reverse osmosis membranes. FIG. 4 (*a*) is a representative image of the uncontrolled biofilm formed for the QS signal minus strain on membranes after 24 h. Additional images of biofilm are provided in FIGS. 5(*a*)-(*f*). See FIG. 4 (*b*) for a representative image of the biofilm formed by the self-controlled strain on membranes after 24 h. Additional images of biofilm are provided are provided in 6(*a*)-(*f*)

Figure 7A:
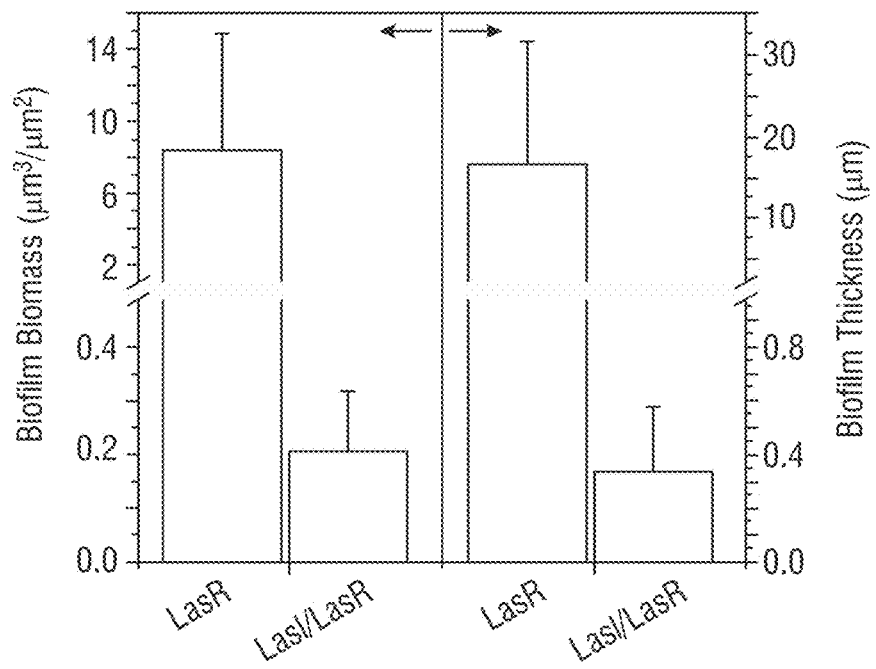
FIG. 7A-B are graphs showing measurement of biomass and thickness (A) and NaCl concentration (B).

See FIG. 7 (*a*) showing permeate flux comparisons membranes with the self-controlled strain and the QS signal minus control strain. See FIG. 7 (*b*) showing biofilm biomass and average biofilm thickness for the QS signal minus strain and the self-controlled strain. All values are averages of three independent colonies (N=3) and the error bars are standard deviation from 6 samples.

This result confirms our previous results showing the QS circuit reduces biofilm formation (FIG. 2); this biofilm formation is common on polyamide membranes[32]. More importantly, it shows that the synthetic circuit assembled regulates its own biofilm amount and thickness on actual desalination membranes.

Water fluxes through the membrane were measured at different feed salt (NaCl) concentrations to compare the effect of biofouling by the self-controlled strain to that by the QS signal negative strain. By measuring filtered water flux, known as permeate flux, at a series of NaCl concentrations; the resistance of the membrane to water flow was evaluated. Comparing clean membrane fluxes (incubated with medium) to fouled membrane (incubated with medium and biomass) fluxes provide a measure of the biofilm resistance. On the other hand, tracking salt rejection for different biofilms provides an understanding of the extent of salt accumulation (or degree of concentration polarization) at the membrane surface, and its contribution to flux decline. An accounting of the clean membrane and biofilm resistances under various conditions are provided in Table 3 and FIG. 8. The membrane resistance was evaluated after incubation of the membrane at 37° C. for 24 h with M9G and LB medium in quantities similar to that used for biofilm growth. See Table 3 below. Similarly, consortial biofilms were incubated in M9G medium with an initial overnight turbidity of 0.5 at 600 nm. All media contained Cm (300 μg/mL) and Cb (250 μg/mL) along with 15 mM L-arginine and 1.6% L-arabinose. The membranes were subjected to a series of different NaCl feed concentrations (0, 5, 10 and 15 mM) at 50 psi and 400 rpm. The resistance was calculated based on measured permeate flux at no salt feed.

$$R_c = \frac{\Delta P}{J\mu} - R_m \quad (3)$$

Figure 7B:
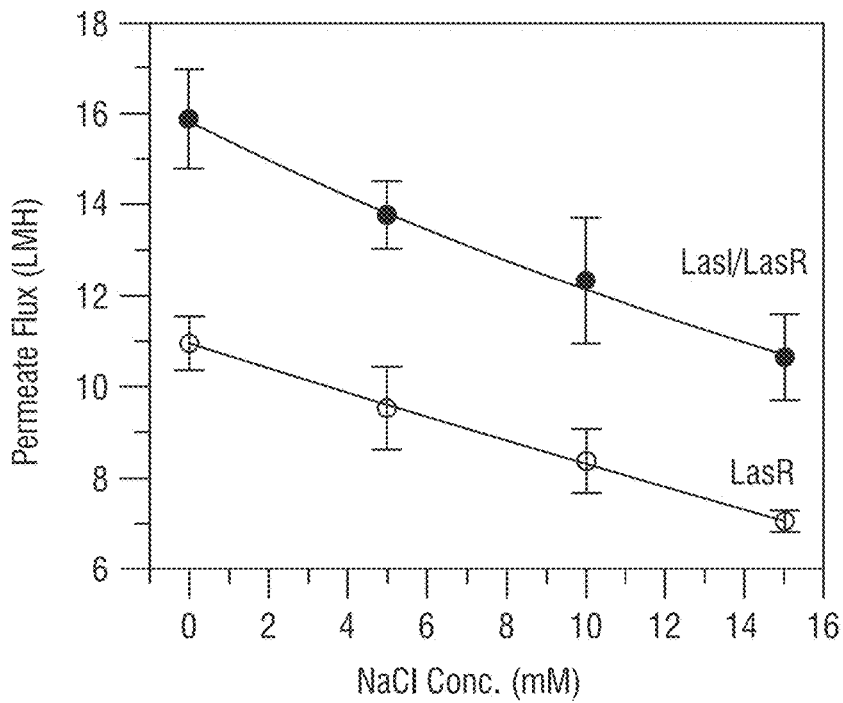
Figure 8:
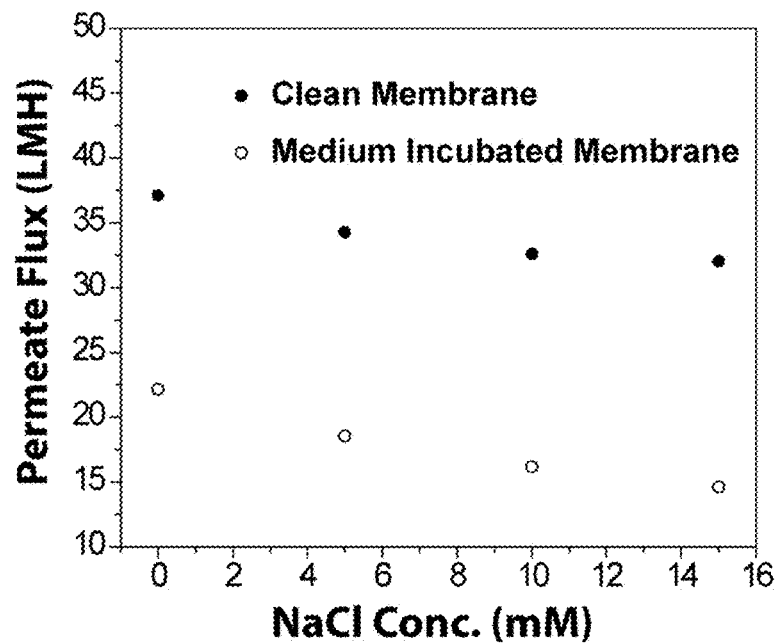
FIG. 8 is a graph showing NF90 membrane permeate flux behavior without a biofilm at different concentrations of NaCl.

FIG. 8 shows NF90 membrane permeate flux behavior without a biofilm. Time averaged permeate flux (liter/m²/h, LMH) was measured over ~30 minutes with different concentrations of NaCl through a NF90 membrane at 50 psi and 400 rpm stirring. The clean membrane flux was almost twice that of the membrane with biofilms shown in FIG. 7b at the same NaCl concentrations over ~30 minutes. However, the medium incubated membrane, developed according to the membrane biofilms method (without bacteria) shown above, demonstrated comparable flux (only an average of ~20% higher flux) behavior compared to membranes with biofilms at the same NaCl concentrations over ~30 minutes. These results are in line with previous studies where growth media leads to lowered fluxes even without the presence of bacteria.

A series of flux experiments for three independent colonies of each strain revealed that application of the self-control synthetic circuit can decrease flux decline caused by uncontrolled fouling by 50% (FIG. 7B). Moreover, NaCl rejection was improved by more than 11% for the case of the self-controlled strain, which was indicative of lower concentration polarization. See Table 4 showing salt rejection improvement with self-controlled (LasI/LasR) biofilm over QS signal negative (LasR) biofilm. The membrane fluxes and related conductivities were evaluated after incubation of the membrane at 37° C. for 24 h with M9G containing Cm (300 μg/mL). The membranes were subjected to 10 mM

TABLE 3

| Average Membrane Resistance ($m^{-1}$) | PAO1/E. coli NO− Average Biofilm Resistance ($m^{-1}$) | PAO1/E. coli NO+ Average Biofilm Resistance ($m^{-1}$) | % Increase in Biofilm Resistance for Control Strain w.r.t. Beneficial Strain |
|---|---|---|---|
| $4.45 \times 10^{13}$ | $4.02 \times 10^{13}$ | $1.51 \times 10^{13}$ | 165.5 |

The membrane resistance ($R_m$) was calculated using NF90 membranes treated according to 'Membrane biofilms' method, but without adding any bacterial cells. Therefore, the resistance provided quantification of medium incubated membrane. This resistance was evaluated using the following equation:

$$R_m = \frac{\Delta P}{\mu J_0} \quad (1)$$

Where, ΔP denotes the applied external pressure differential, μ is medium viscosity (assumed pure water viscosity at 25° C.) and $J_0$ signifies the pure water flux through the medium-incubated membrane. The pure water flux (J) through the biofilm-grown membrane at no salt feed is as follows:

$$J = \frac{\Delta P}{\mu(R_m + R_c)} \quad (2)$$

Therefore, the biofilm resistance, which should be deconvoluted from total resistance, could be calculated using Equation (2) as follows—

NaCl feed concentration at 50 psi and 400 rpm. The feed conductivity was the average of start of run and end of run measurements. The permeate conductivity was measured at the end of run.

TABLE 4

| 10 mM NaCl Feed | Feed conductivity (μS/cm) at room temperature | Permeate conductivity (μS/cm) at room temperature | % Average Rejection (R) |
|---|---|---|---|
| 1. LasR | 1184 | 271 | 75 |
| 2. LasR | 1172 | 352 | |
| 3. LasR | 1154 | 236 | |
| 1. LasI/LasR | 1146 | 160 | 86 |
| 2. LasI/LasR | 1181 | 122 | |
| 3. LasI/LasR | 1177 | 215 | |

Overall, by controlling its biofilm formation, the self-controlled biofilm increases permeate flux significantly by reducing biofouling.

Deleterious Biofilm Formation is Reduced and Permeate Flux is Increased by the Beneficial Biofilm that Produces NO. To create a strain capable of dispersing a wide-range of biofilms so as to limit biofouling on RO membranes, the gene encoding NO synthase from *B. subtilis*[21] (bNos) was added to the self-controlled strain to form the strain that limits its own biofilm formation as well as produces NO to disperse deleterious biofilms. This strain is referred to as *E. coli* TG1/pBdcAE50Q-lasI-lasR/pBNos, FIG. 1, henceforth "beneficial biofilm strain".

Figure 3:
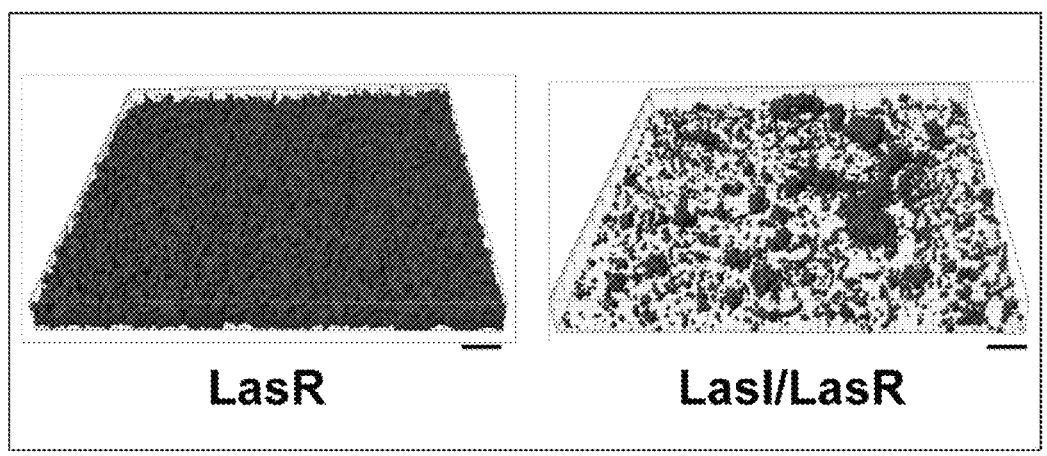
FIG. 3 is confocal microscopy visualizations of a control strain (LasR) and a self-controlled strain (LasI/LasR) on glass surfaces.

A 96-well plate assay was performed to confirm that the QS circuit was still active after the addition of pBNos plasmid; the beneficial biofilm strain had six-fold less biofilm after 24 h compared to the negative control strain (*E. coli* TG1/pBdcAE50Q-lasI-lasR/pBad) (FIG. 3). After 24 h, the beneficial biofilm strain produced 11±4 µM of NO which was 3 to 6 fold higher than the control strain (*E. coli* TG1/pBdcAE50Q-lasI-lasR/pBad) which lacks NO synthesis (FIG. 9).

Figure 12A:
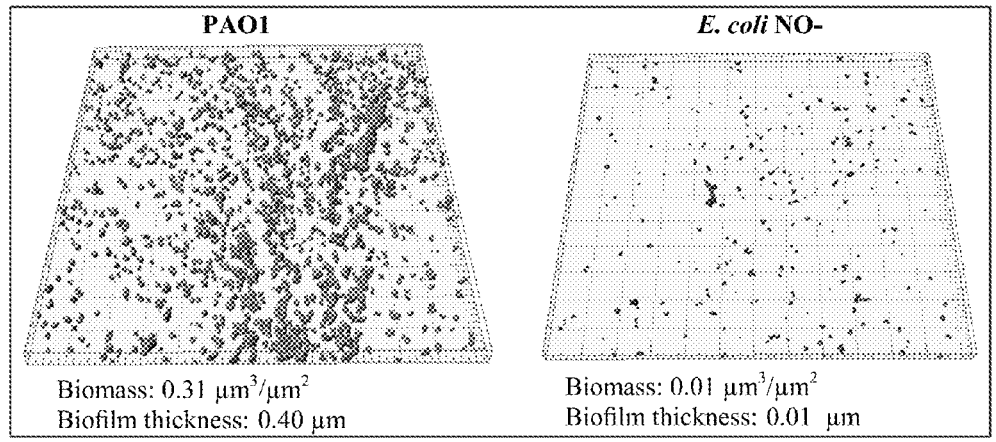
FIG. 12A-O are images of consortial biofilms of $P.$ aeruginosa PAO1 and $E.$ coli NO-.
Figure 12B:
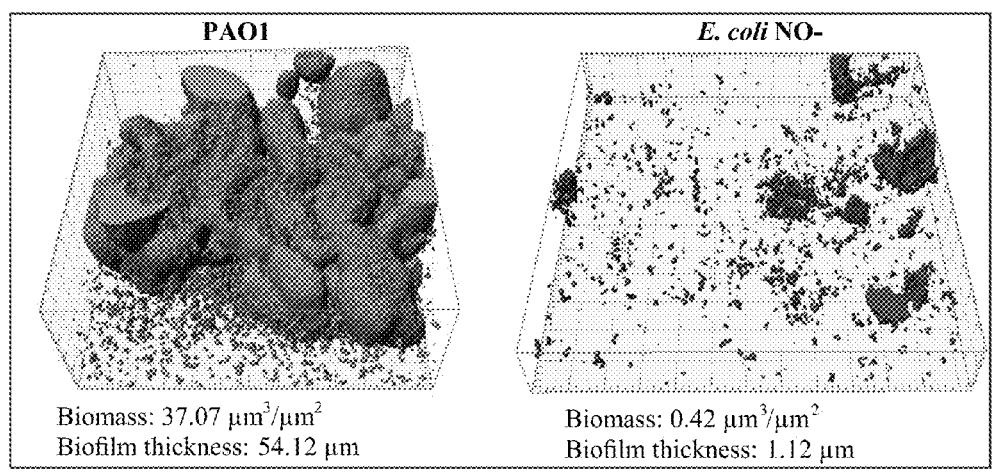
Figure 12C:
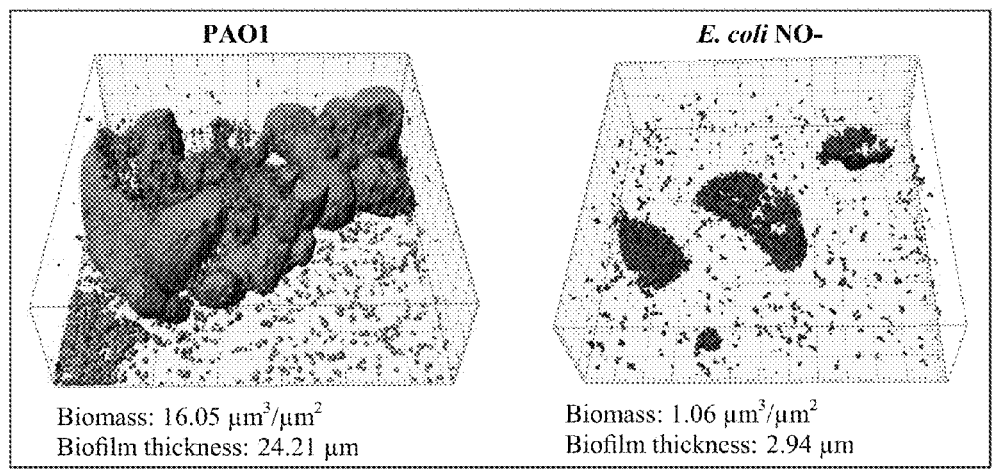
Figure 12D:
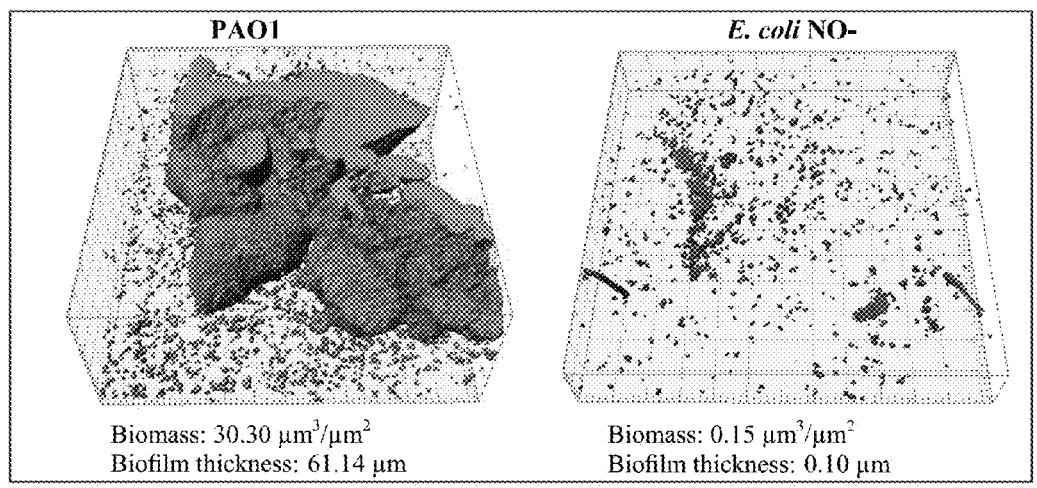
Figure 12E:
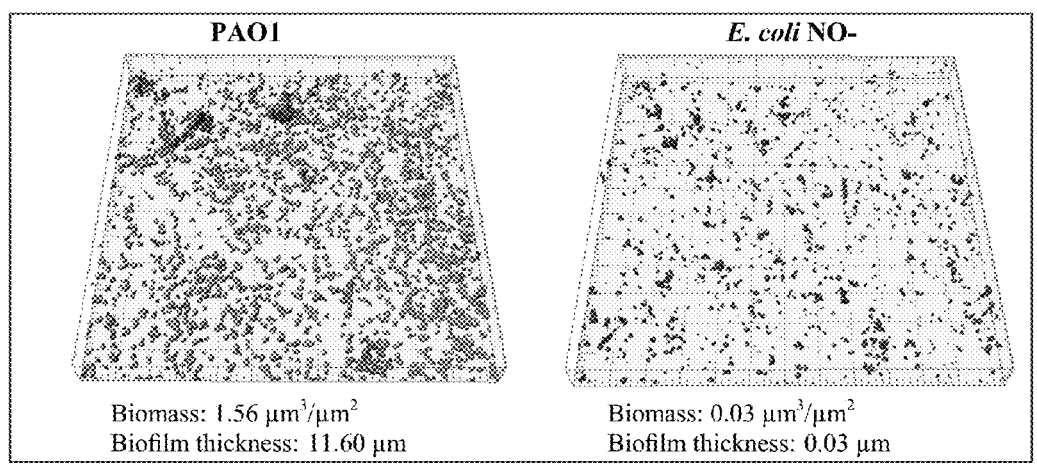
Figure 12F:
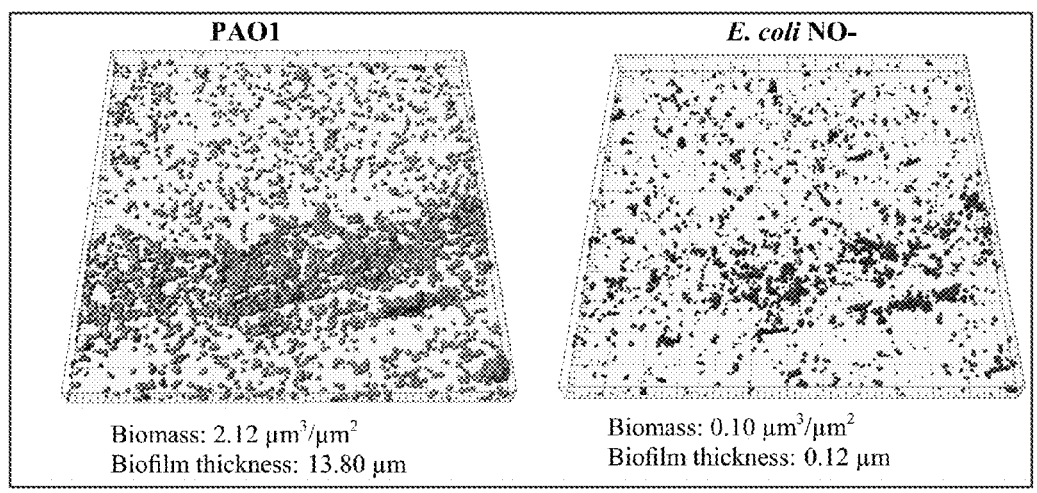
Figure 12G:
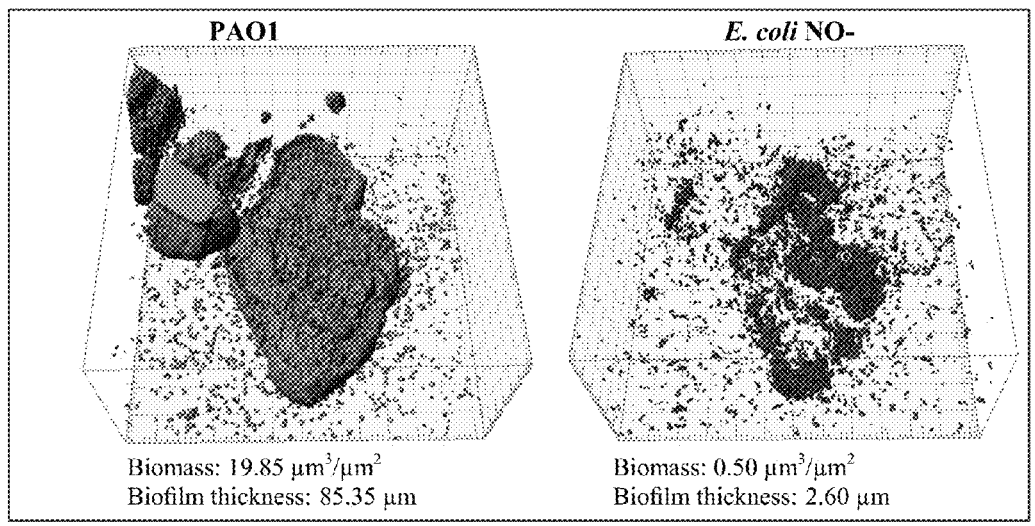
Figure 12H:
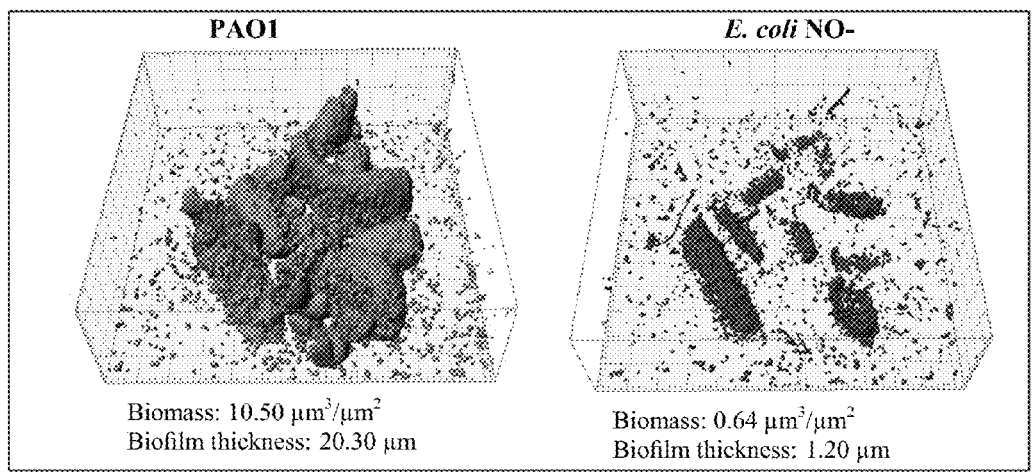
Figure 12I:
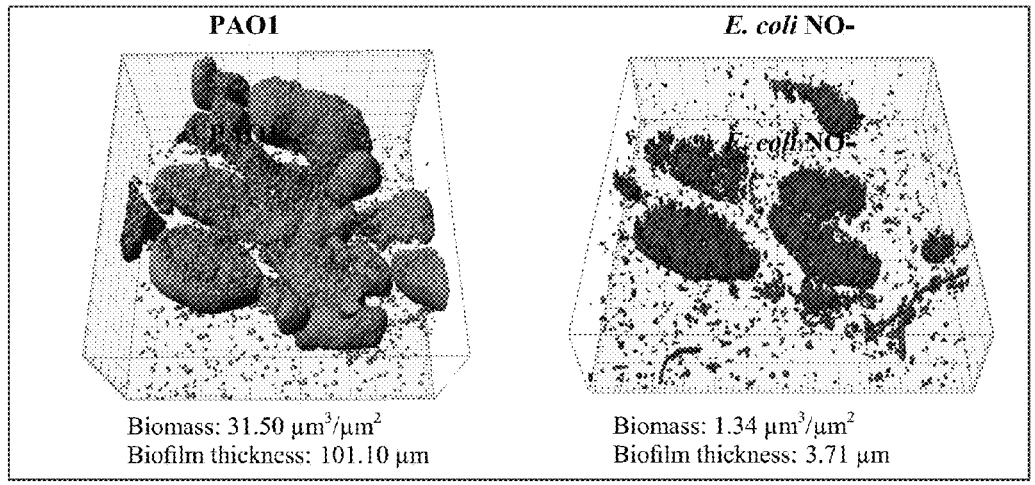
Figure 12J:
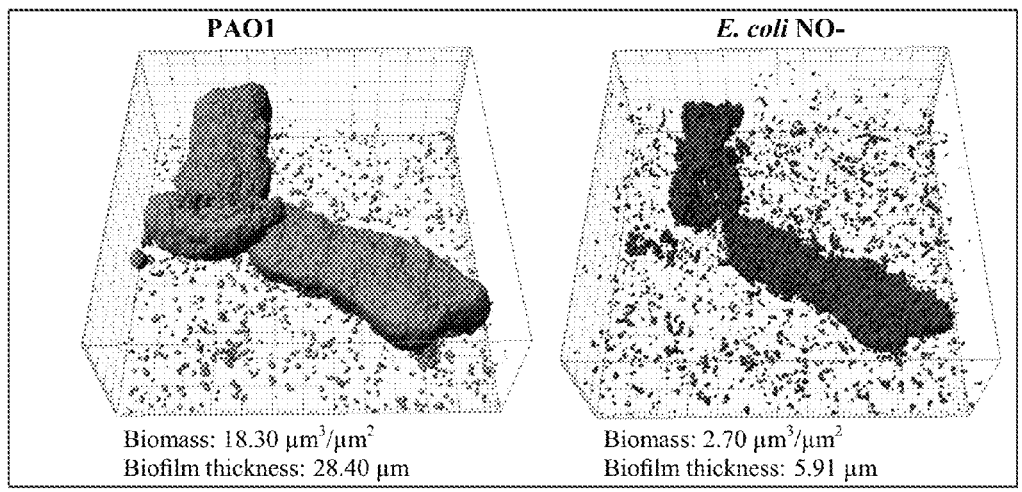
Figure 12K:
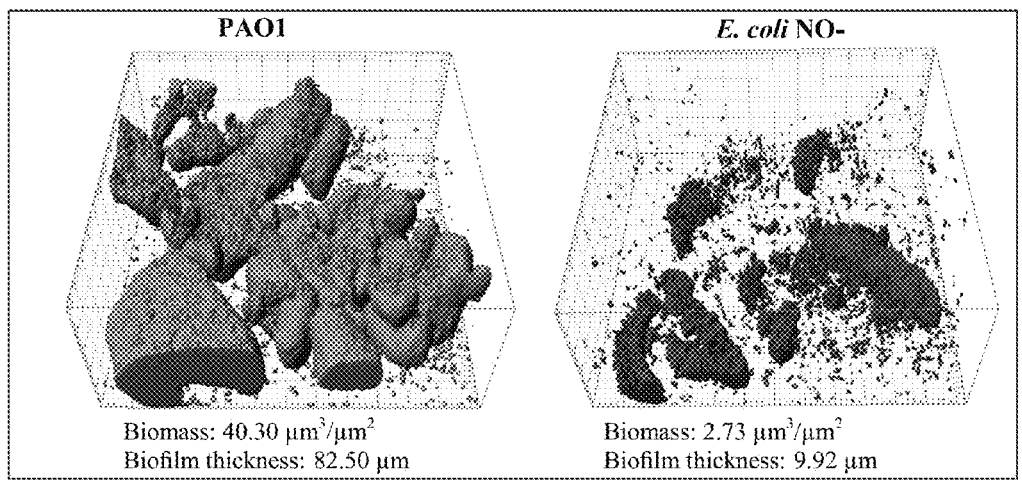
Figure 12L:
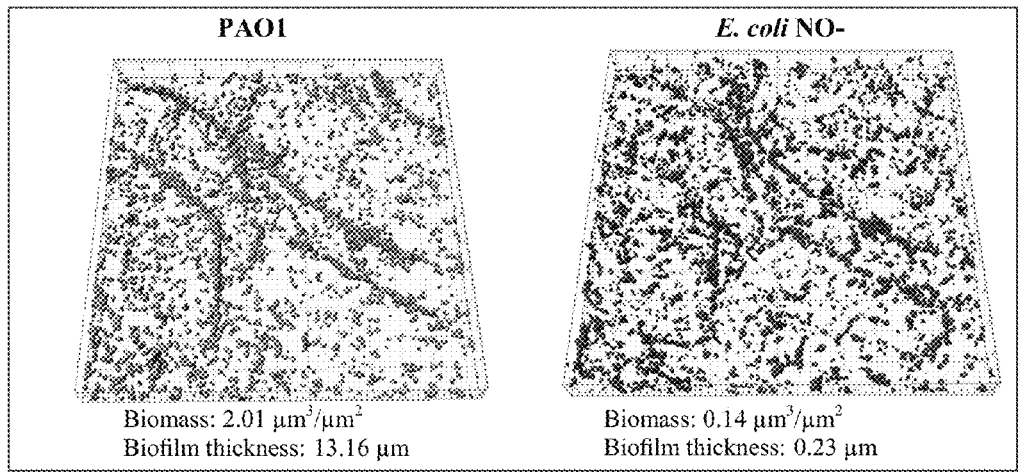
Figure 12M:
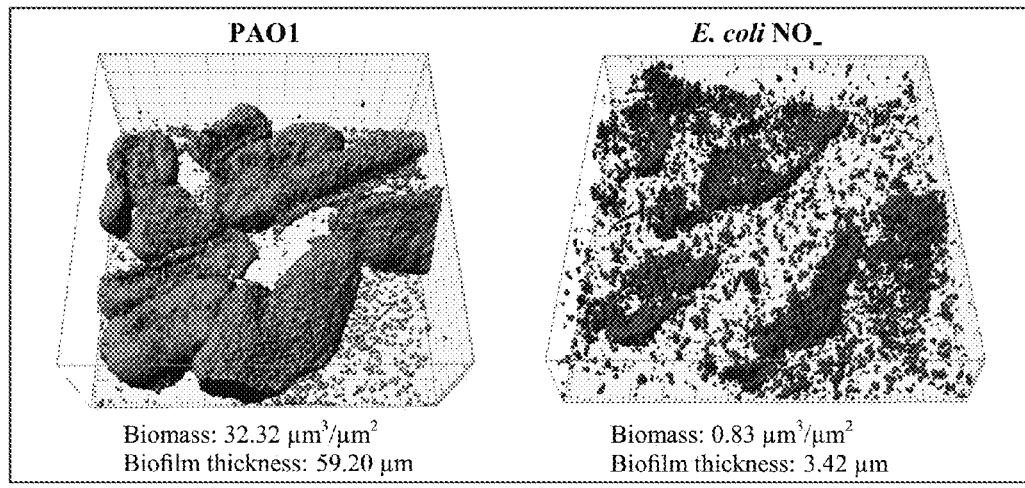
Figure 12N:
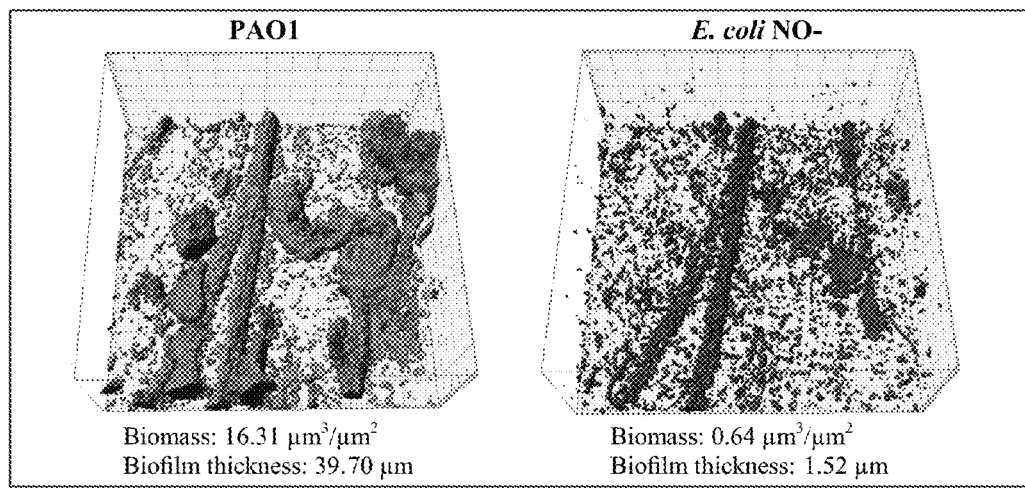
Figure 12O:
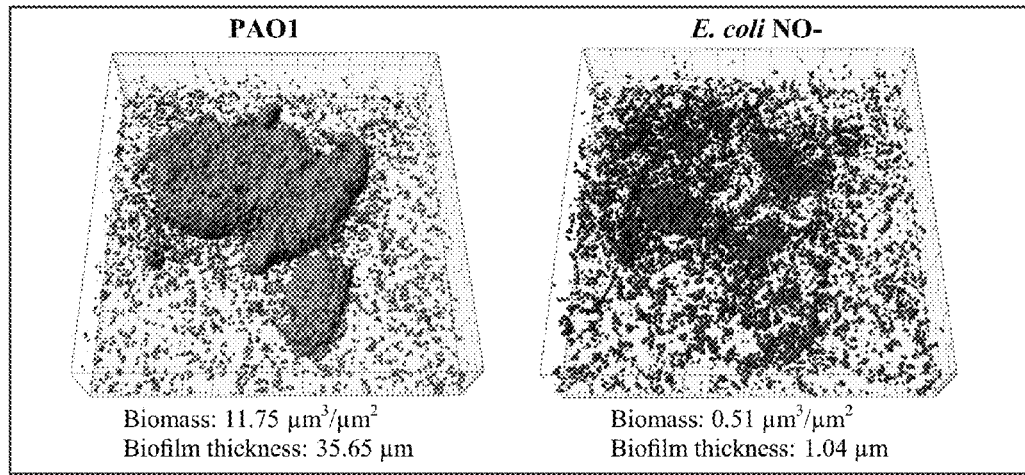
Figure 13:
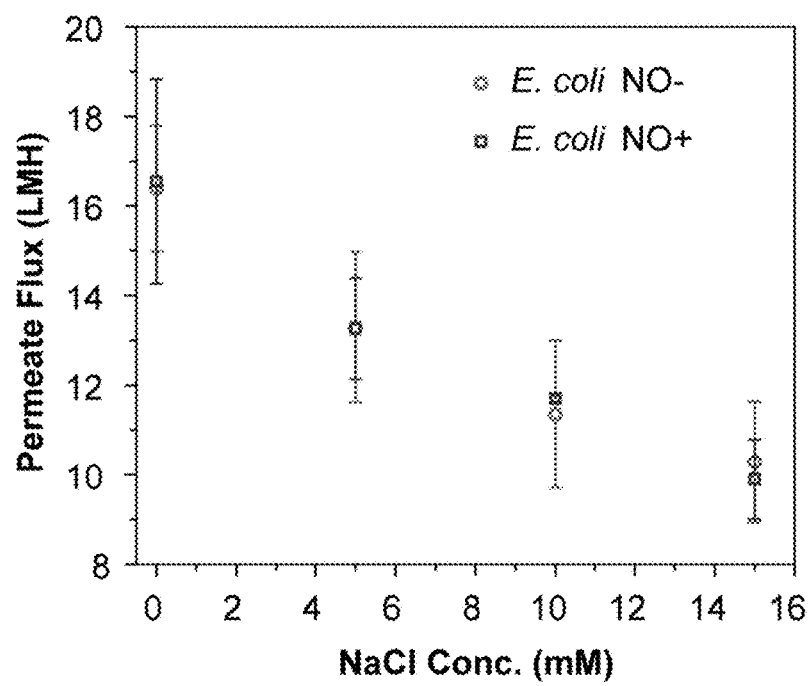
FIG. 13 is a graph showing permeate flux with control $E.$ coli NO-, TG1/pBdcAe50Q-lasI-lasR/pBad) and beneficial strain ($E.$ coli NO+, TG1/pBdcAE50Q-lasI/lasR/pBNos) at different concentrations of NaCl.
Figure 14A:
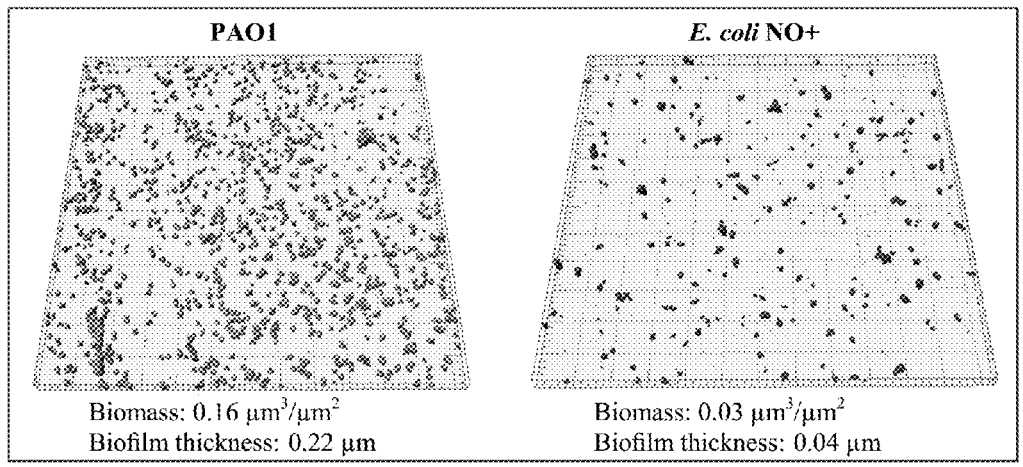
FIG. 14A-O are images of consortial biofilms of $P.$ aeruginosa PAO1 and $E.$ coli NO+.
Figure 14B:
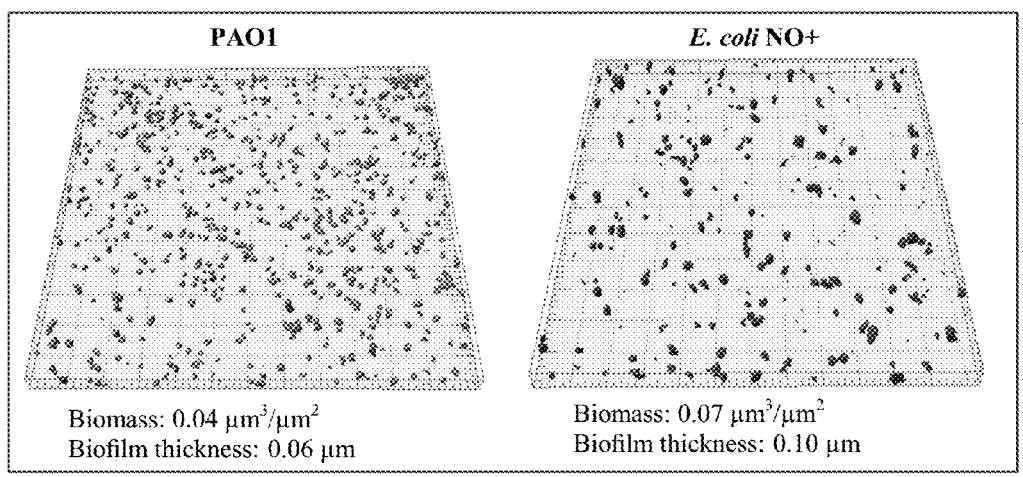
Figure 14C:
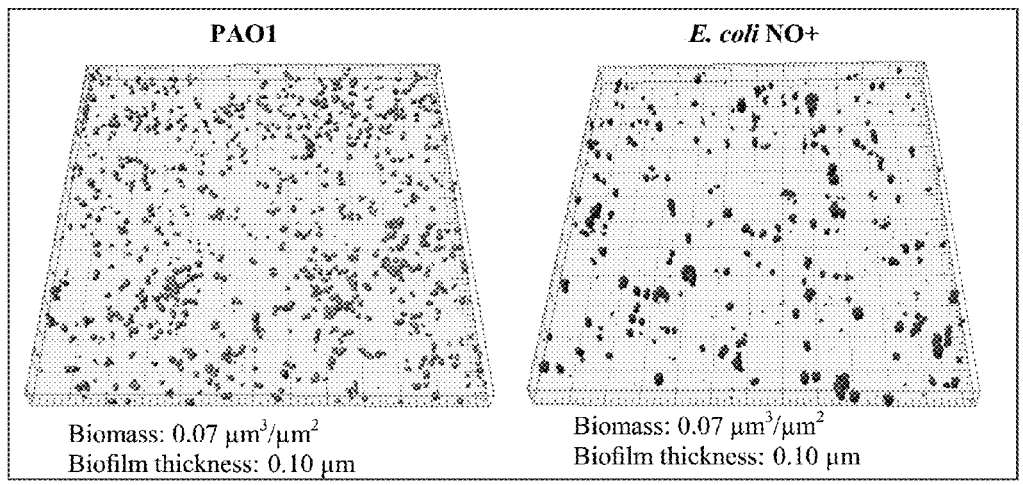
Figure 14D:
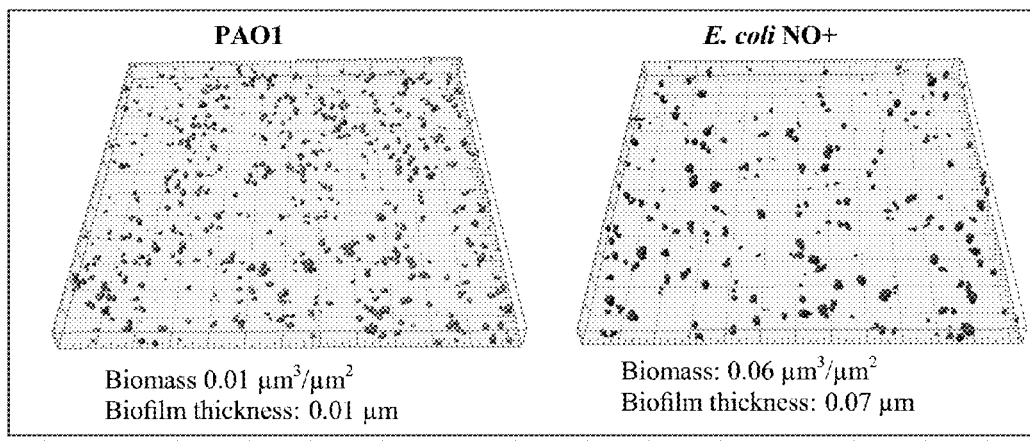
Figure 14E:
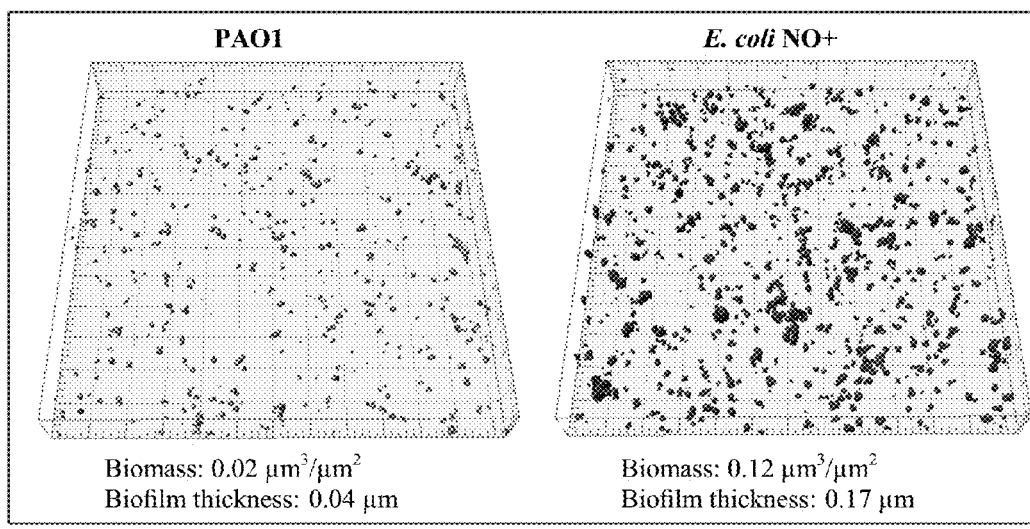
Figure 14F:
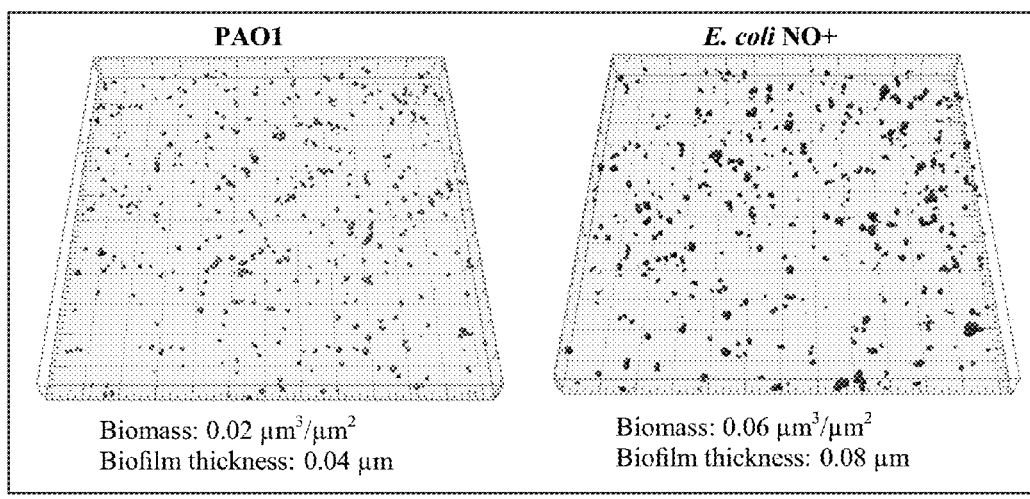
Figure 14G:
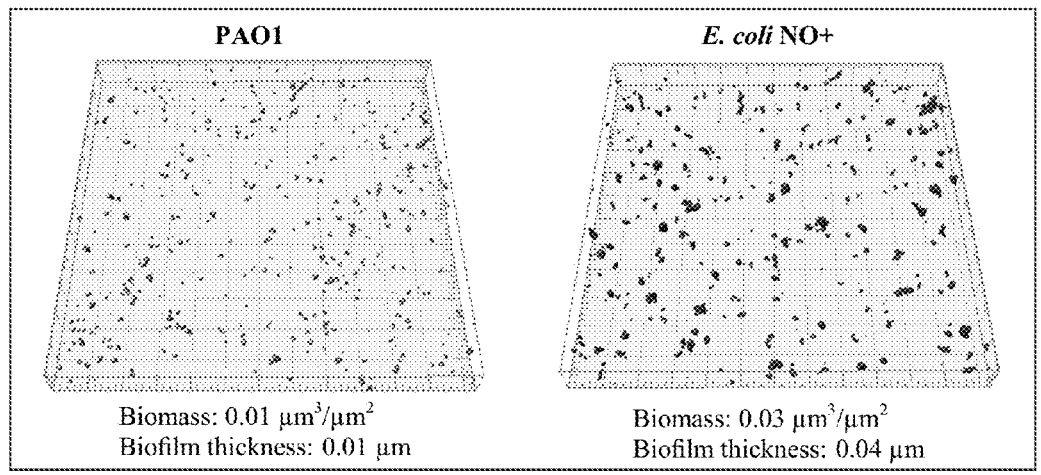
Figure 14H:
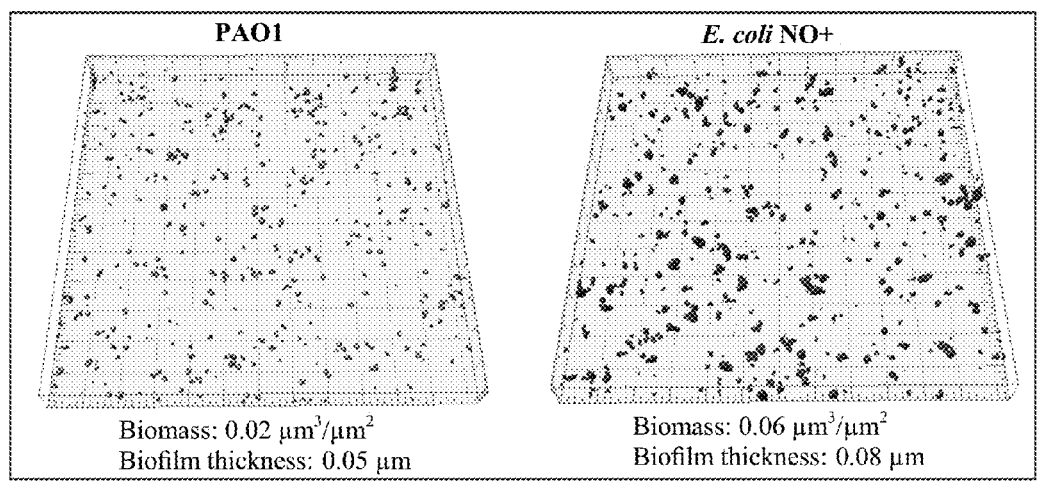
Figure 14I:
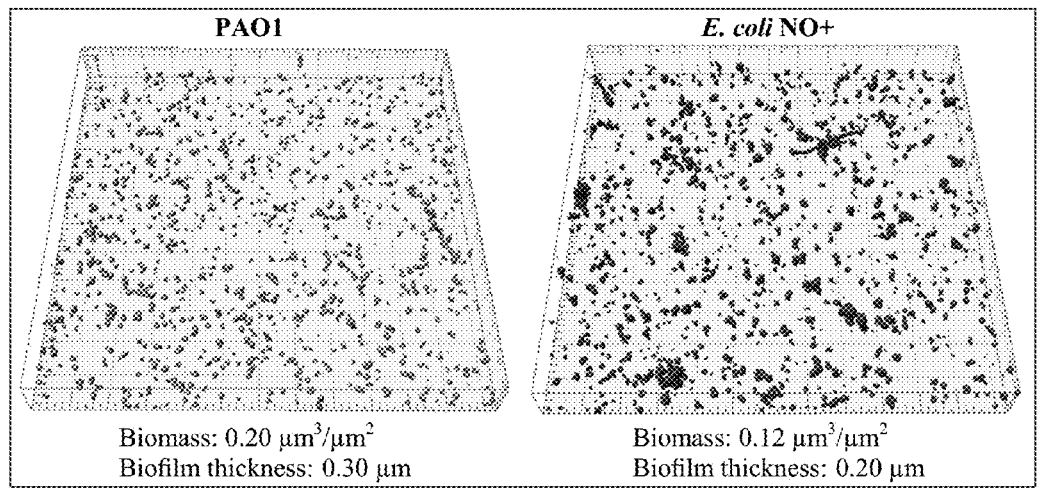
Figure 14J:
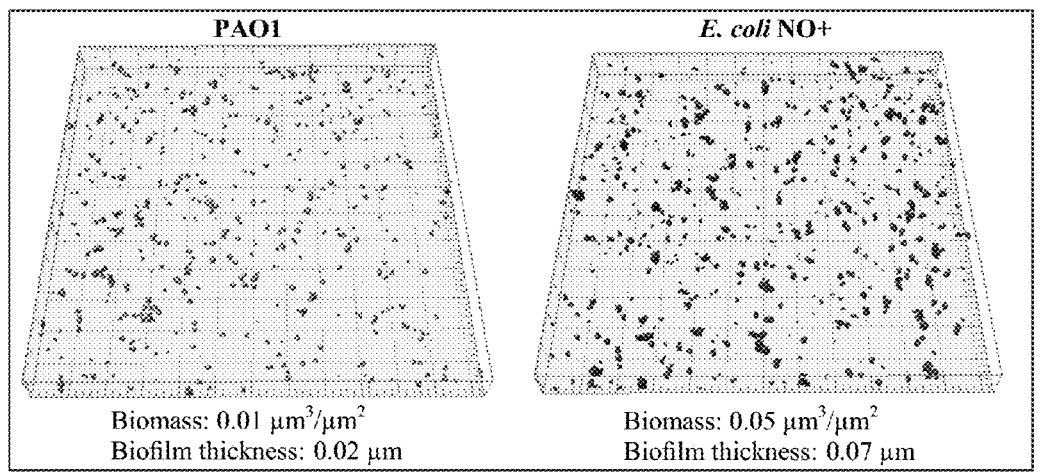
Figure 14K:
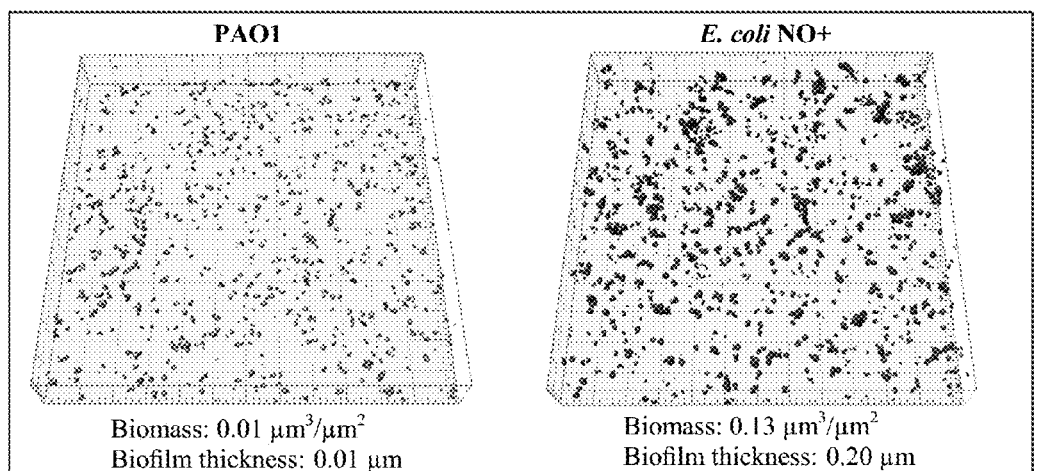
Figure 14L:
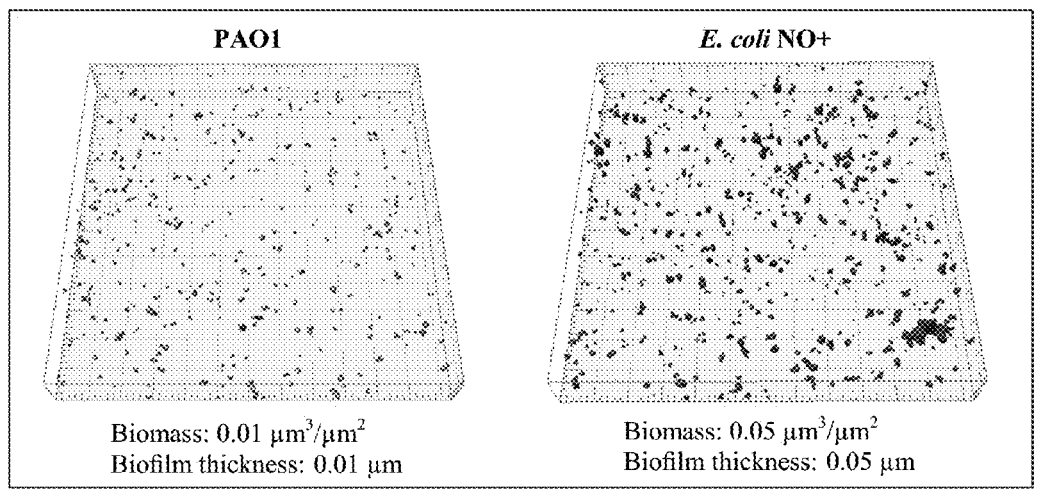
Figure 14M:
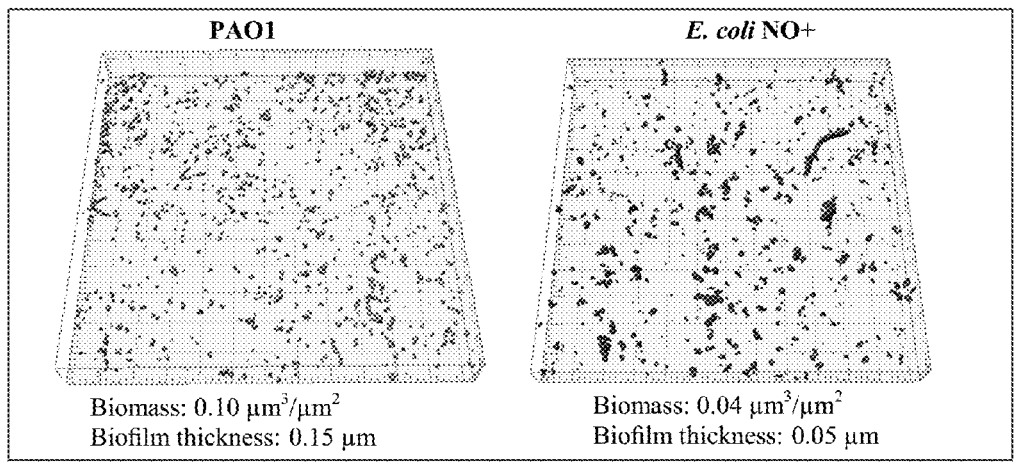
Figure 14N:
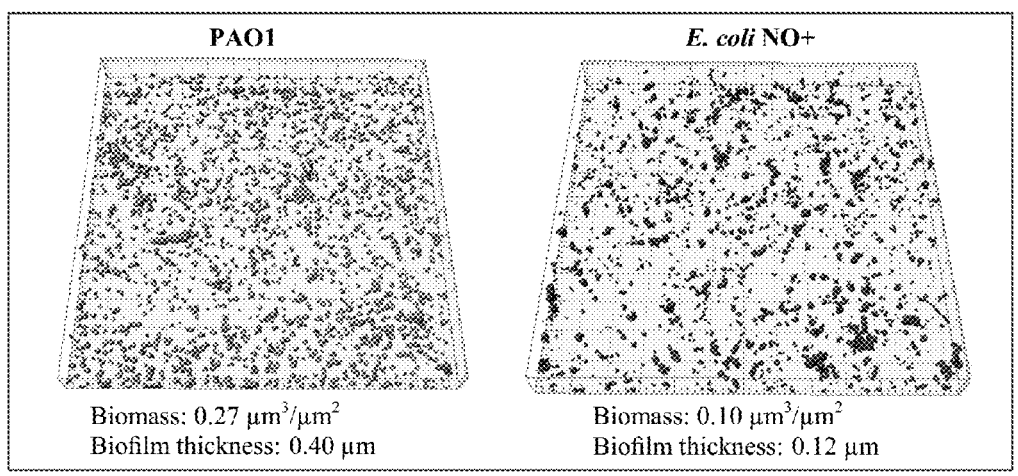
Figure 14O:
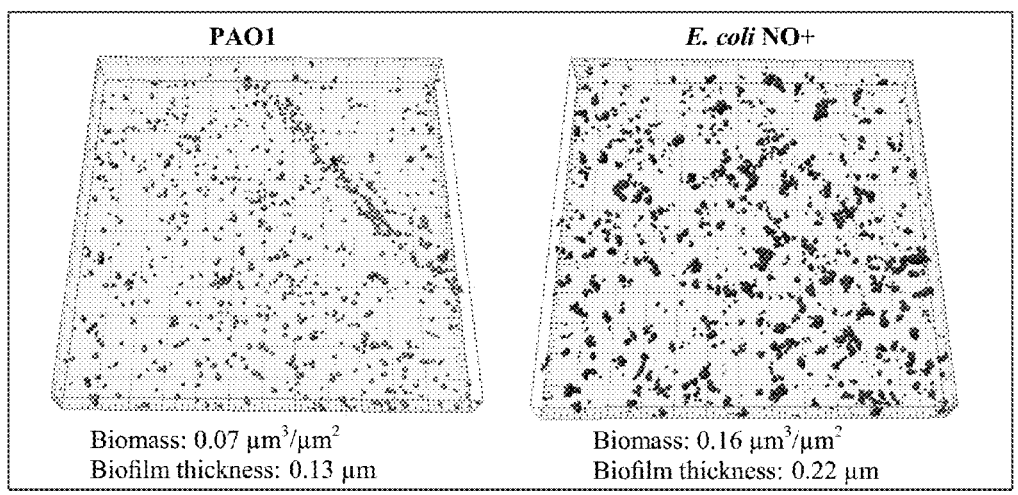
Figure 15:
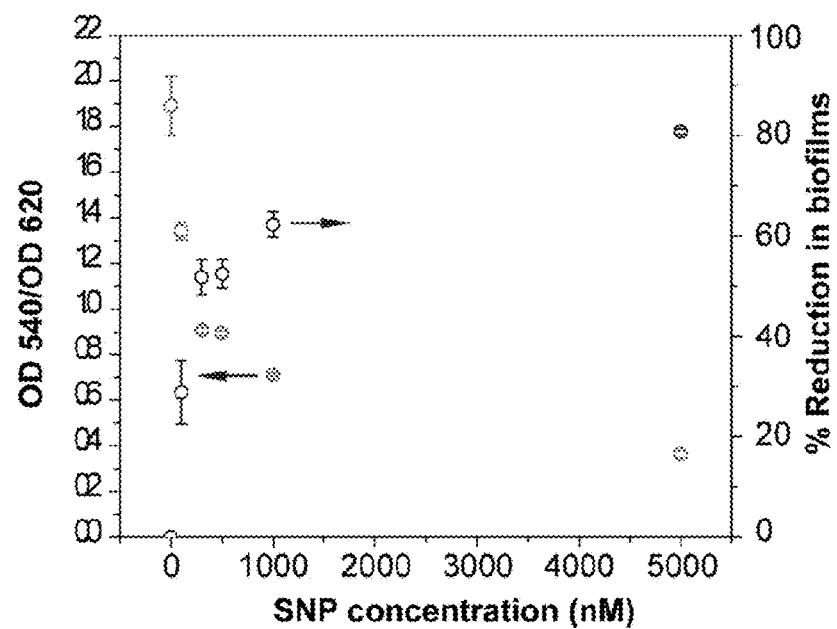
FIG. 15 is a graph showing normalized $P.$ aeruginosa biofilm formation in 96-well plates with SNP as the NO donor and measuring reduction in biofilms.

To demonstrate that the beneficial biofilm strain can inhibit biofilm formation on RO membranes by deleterious bacteria, the activity of NO against the biofilm formation of *P. aeruginosa* was assayed by tagging the beneficial biofilm with the red fluorescent protein (RFP) and *P. aeruginosa* with the green fluorescent protein (GFP). Using confocal microscopy (FIG. 10A-D, the beneficial biofilm strain reduced the amount of the *P. aeruginosa* biofilm biomass by around 40 fold and reduced the average biofilm thickness by around 100 fold (FIG. 11A) compared to the negative control that does not produce NO (*E. coli* TG1/pBdcAE50Q-lasI-lasR/pBad). Critically, in the absence of NO, the *P. aeruginosa* biofilm dominates over the beneficial biofilm by forming sporadic patches on the membrane, often where *E. coli* was present (PAO1/*E. coli* NO– in FIG. 12A-O), reducing membrane flux by almost 31% after 24 h compared to the self-controlled strain without *P. aeruginosa* (PAO1/*E. coli* NO– in FIG. 11B and *E. coli* NO– in FIG. 13. The average of PAO1 in FIG. 12 A-O measurements was biomass of 18.01 µm³/µm², biofilm thickness of 42.03 µm and roughness co-efficient of 0.18. Average of *E. coli* NO– was biomass of 0.80 µm³/µm², biofilm thickness of 2.25 µm and roughness co-efficient of 1.95. FIG. 13 shows permeate flux with the control (*E. coli* NO–, TG1/pBdcAE50Q-lasI-lasR/pBad) and beneficial strain (*E. coli* NO+, TG1/pBdcAE50Q-lasI-lasR/pBNos). Biofilms were formed for 24 hr on NF90 membranes with M9G medium, Cm (300 µg/mL), Cb (250 µg/mL), 1.6% arabinose, and 15 mM L-arginine. The RO system was pressurized at 50 psi and stirred at 400 rpm; 0, 5, 10, and 15 mM NaCl feed concentrations were used to test the permeate flux through membranes with the biofilms. There is no significant difference for flux values between the *E. coli* NO+ and *E. coli* NO– biofilm covered membrane–; the flux is also similar to that of the *E. coli* LasI/LasR (TG1/pBdcAE50Q-lasI-lasR) biofilm-covered membrane shown in FIG. 7D. However, production of NO by the beneficial biofilm strain reduced biofouling by reducing the biofilm of the deleterious species (PAO1/*E. coli* NO+ in FIG. 14A-O. Average measurement of PAO1 NO+ in FIG. 14A-O was biomass of 0.06 µm³/µm², biofilm thickness of 0.10 µm and roughness co-efficient of 2.00. Average measurement of *E. coli* NO+ was biomass of 0.07 µm³/µm², biofilm thickness of 0.10 µm and roughness co-efficient of 1.94. Without the presence of the beneficial biofilm, the control biofilm generated 165% more resistance to flux due to *P. aeruginosa* infiltration into the biofilm (Table 3). Thus, the control consortial biofilm generated an additional resistance which approximately doubles the clean membrane resistance while the beneficial biofilm essentially negated this increase. The beneficial biofilm produced similar permeate flux (LasI/LasR in FIG. 7B compared to *E. coli* NO+ in FIG. 13) compared to the self-controlled strain, so the production of NO by the beneficial strain did not affect permeate flux. As a positive control for NO dispersal of *P. aeruginosa*, sodium nitroprusside (SNP) was used to generate NO which dispersed the *P. aeruginosa* biofilm in 96 well plates; at 5 µM SNP, normalized *P. aeruginosa* biofilm was reduced by 80% See FIG. 15 showing normalized *P. aeruginosa* biofilm formation in 96-well plates with SNP as the NO donor. 80% reduction in normalized biofilm was attained with 5 mM SNP. The filled circles represent normalized biofilms (ratio of OD 540 nm to OD 620 nm) and the empty circles represent % reduction in normalized biofilms with respect to no SNP addition. Biofilms were formed for 24 h at 37° C. in M9G in a 96 well plate without shaking. The error bars represent standard deviation for 3 independent colonies.

Therefore, by controlling the biofilm formation of the deleterious strain, the self-controlled biofilm increased permeate flux and increased operating flux.

Figure 9:
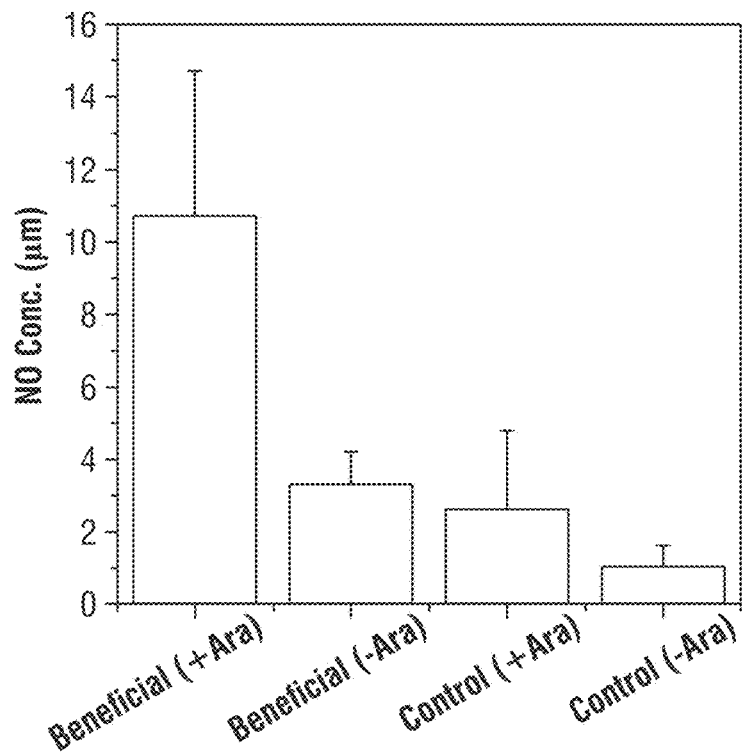
FIG. 9 is a graph showing NO concentration for the control or "beneficial" self-controlled strain having NO encoding sequences added with and without inducing arabinose added (+Ara or -Ara).

In detail, see FIG. 9. FIG. 9 shows NO production for the beneficial biofilm strain (*E. coli* TG1/pBdcAE50Q-lasI-lasR/pBNos) after 24 h in M9G medium with 15 mM arginine (substrate for NO synthase) compared to the control strain (*E. coli* TG1/pBdcAE50Q-lasI-lasR/pBad). Arabinose induces the bNos gene.

Figure 10A:
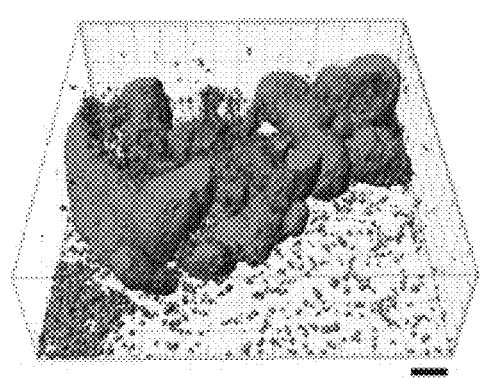
FIGS. 10A-D are confocal microscopy visualizations of biofilm formation of biofilm consortium on reverse osmosis membrane, with $P.$ aeruginosa consortium biofilm (green), consortium biofilm of $E.$ coli control strain (red), showing control (A), "beneficial" strain with no inducement of NO production (B), control with NO (C) and "beneficial" strain with NO production (D).
Figure 10B:
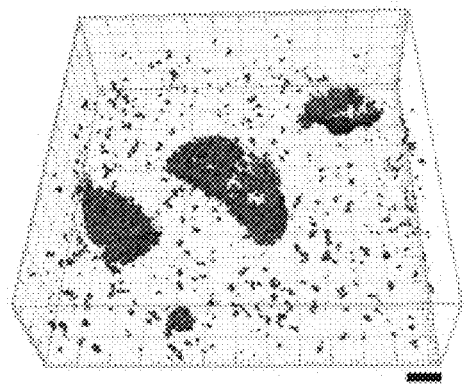
Figure 10C:
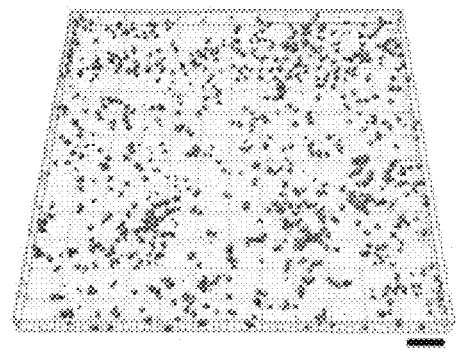
Figure 10D:
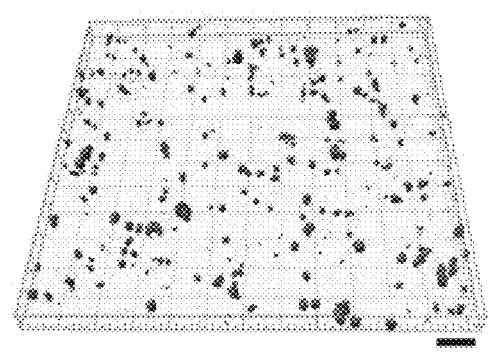

Confocal microscopy was used to discern the biofilm formation of *P. aeruginosa* and the *E. coli* beneficial biofilm consortium developed on the reverse osmosis membrane after 48 h. The biofilm formation of each bacterium in the consortium is shown separately. *P. aeruginosa* consortial biofilm ("PAO1") (green) (FIG. 10A) and consortial biofilm of the *E. coli* control strain (TG1/pBdcAE50Q-lasI-lasR/pBad) (red) that does not produce NO ("*E. coli* NO–") (FIG. 10B). Consortium of the *P. aeruginosa* biofilm (FIG. 10C) and the beneficial biofilm strain (*E. coli* TG1/pBdcAE50Q-lasI-lasR/pBNos, "*E. coli* NO+") FIG. 10D. Scale bars, 20 µm.

Figure 11A:
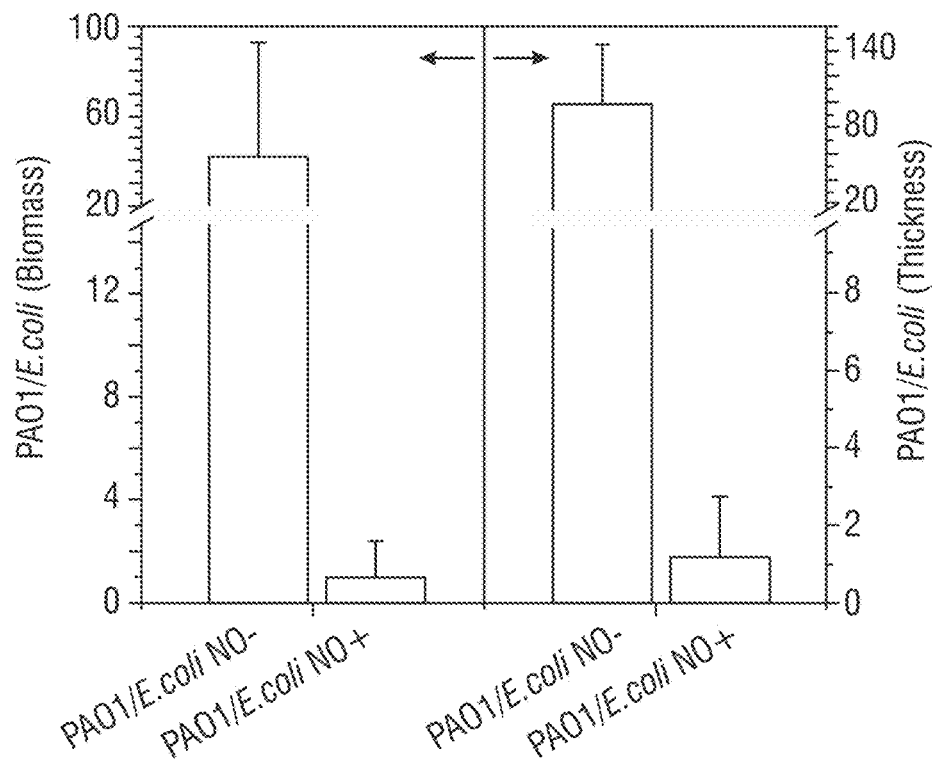
FIGS. 11A-B are graphs showing analysis of consortium biofilm biomass and average thickness with and without NO (A) and NaCl concentration (B).
Figure 11B:
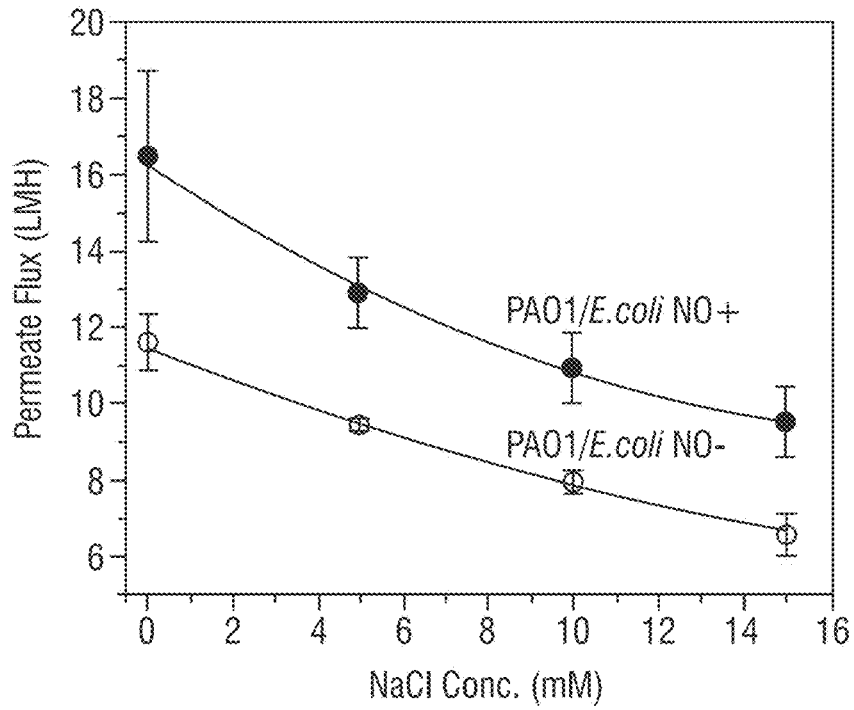

FIG. 11A shows COMSTAT analysis of consortia biofilm biomass and average thickness. The error bars represent standard deviations from a sample size of 15. (FIG. 11B) RO flux measurements with the *P. aeruginosa* ("PAO1")/*E. coli* biofilm consortia on NF90 membranes. The error bars are standard deviations from three independent experiments for each type of consortial challenge, PAO1/*E. coli* NO– and PAO1/*E. coli* NO+.

Figure 16A:
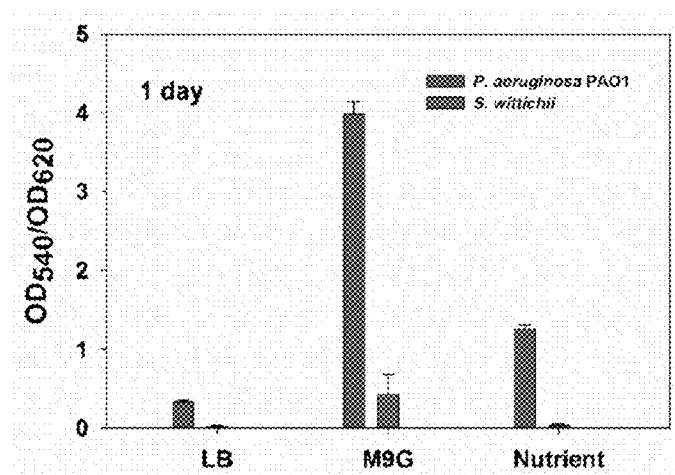
FIG. 16A-C are graphs showing normalized $P.$ aeruginosa PAO1 and $S.$ wittichii biofilm formation in 96-well plates after one day (A), two days (B) and three days (C) growth as grown in LB, M9G medium or nutrient medium containing peptone and beef extracts.
Figure 16B:
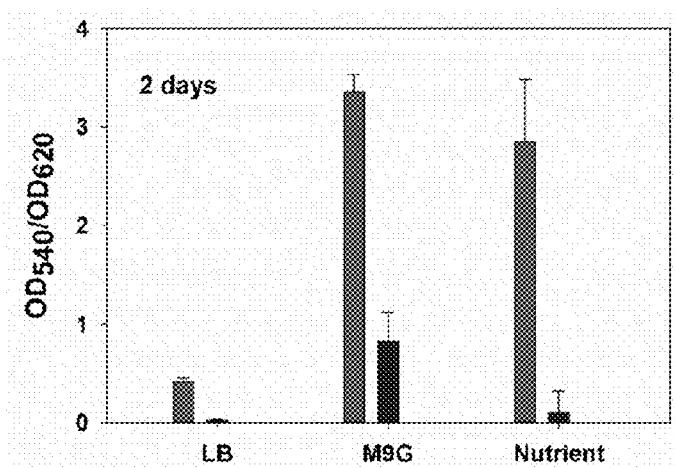
Figure 16C:
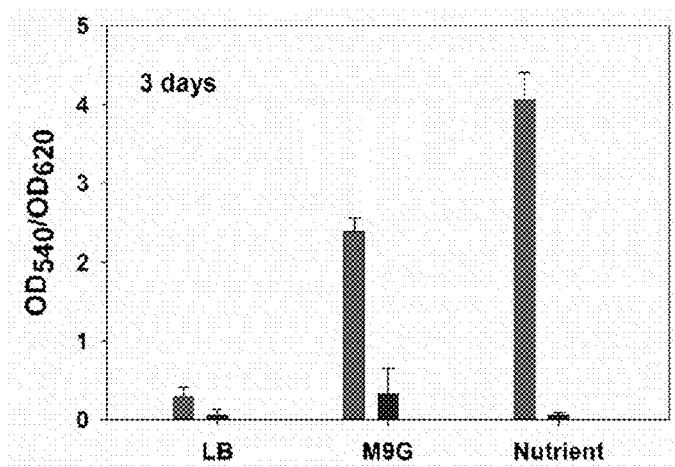

We also investigated the ability of the beneficial biofilm to inhibit the biofilm of the other prominent biofouling organism, *S. wittichii*. Compared to *P. aeruginosa*, *S. wittichii* produced less biofilm under all conditions tested. See FIG. 16 showing normalized *P. aeruginosa* PAO1 and *S. wittichii* biofilm formation in 96-well plates at 30° C. after 1 (a), 2 (b), and 3 (c) days shows *P. aeruginosa* biofilm formation dominates that of *S. wittichii* in all media tested. The strains were grown in LB, M9G, and nutrient medium containing peptone (5 g/L) and beef extract (3 g/L).

Figure 17A:
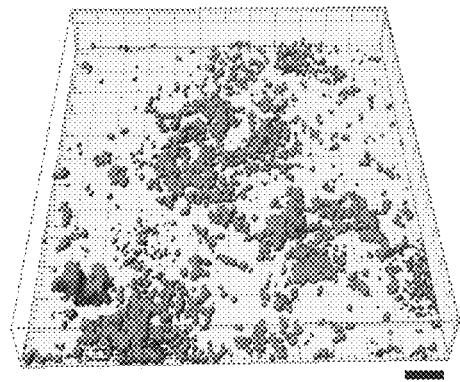
FIG. 17 A-D are images of consortial biofilms of $S.$ wittichii and $E.$ coli where $S.$ wittichii biofilm formed in the absence of NO (A) relative to $E.$ coli control strain (B), and in the presence of NO by the beneficial biofilm strain ($E.$ coli TG1/pBdcAE50Q-lasI-lasR/pBNos), total biofilm formation is reduced (C) and biomass of the beneficial strain also shown (D).
Figure 17B:
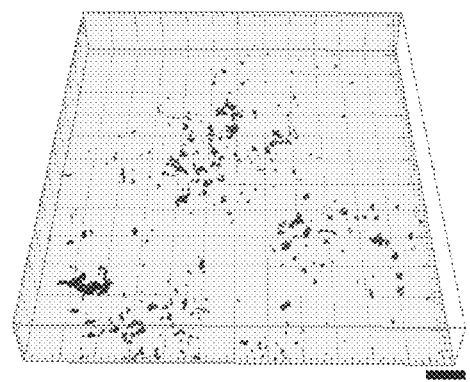
Figure 17C:
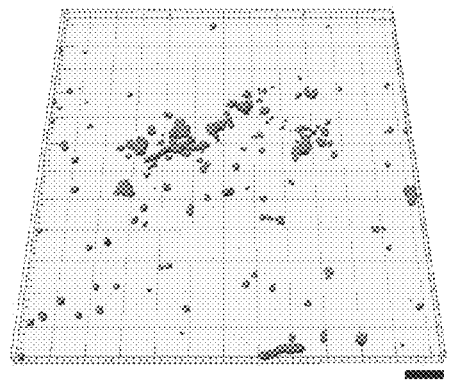
Figure 17D:
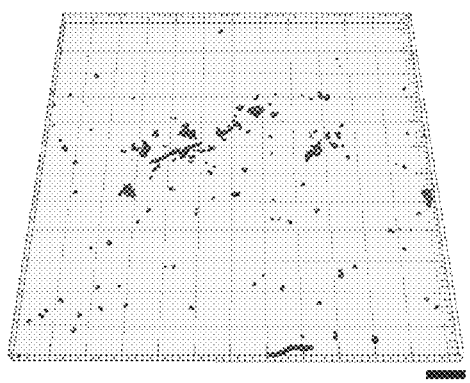
Figure 18:
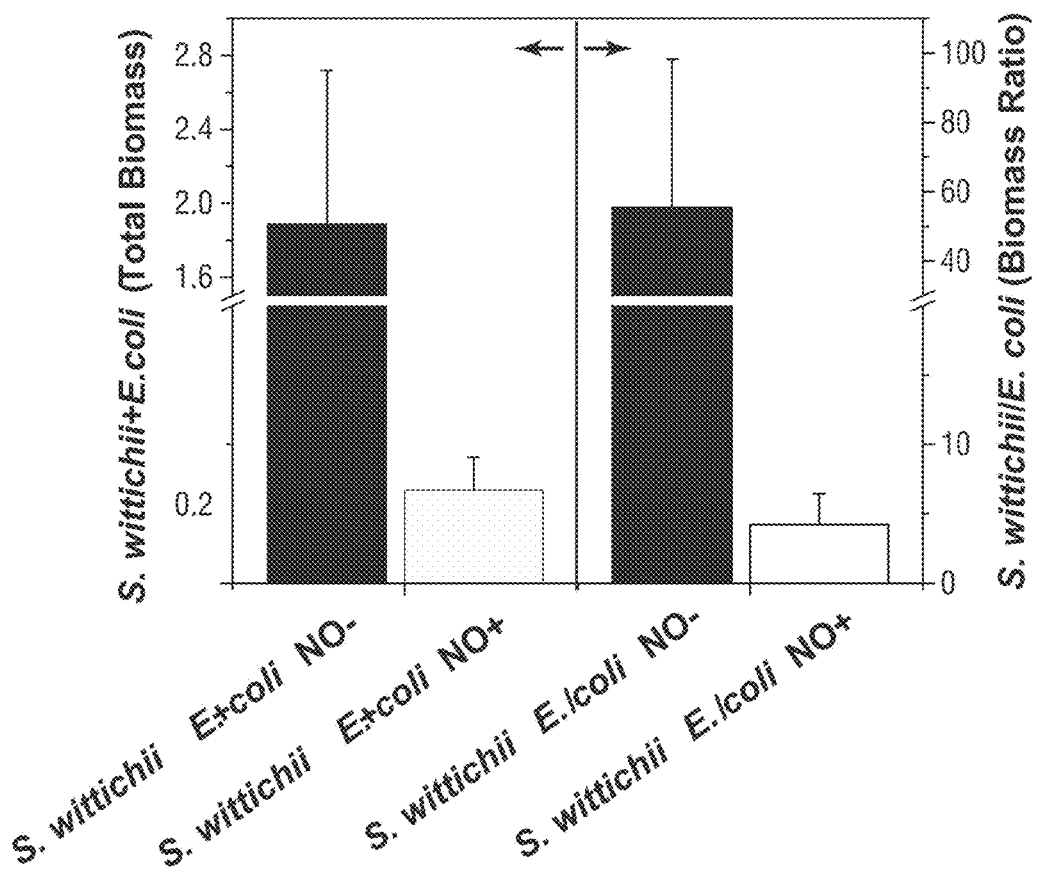
FIG. 18 is a graph showing reduction of $S.$ wittchii biomass and total biomass when NO was or as not produced.

On membranes with consortia, without the presence of NO, the control strain (*E. coli* TG1/pBdcAE50Q-lasI-lasR/pBad) could not prevent *S. wittichii* biofilm formation after two days as evident from larger total biofilm biomass found on the membrane (FIG. 17A) relative to the *E. coli* control strain portion of the consortial biofilm (FIG. 17B); in fact, most of the consortial biofilm was that of *S. wittichii*. In contrast, in the presence of NO produced by the beneficial biofilm strain (*E. coli* TG1/pBdcAE50Q-lasI-lasR/pBNos), total biofilm formation (FIG. 17C) was reduced by more than an order of magnitude (FIG. 18). Since the biofilm biomass of the portion of the consortium that is the beneficial strain (FIG. 17E) is roughly the same as the total biofilm (FIG. 17C), the *S. wittichii* biofilm was almost completely eliminated when NO was produced. Hence, *S. wittichii* biomass was reduced 17-fold when NO was produced by the beneficial biofilm strain (FIG. 18). Therefore, our beneficial strain is a general solution for preventing biofouling since it reduced the biofilm formation of both *P. aeruginosa* and *S. wittichii*. Note that unlike the consortial biofilm experiments with *P. aeruginosa* in which the pseudomonad was tagged with GFP, to determine the *S. wittichii* biofilm levels, we subtracted the *E. coli* biofilm levels (determined by RFP levels) from the total biofilm that was determined by staining both strains with SYTO9 (green).

Figure 19A:
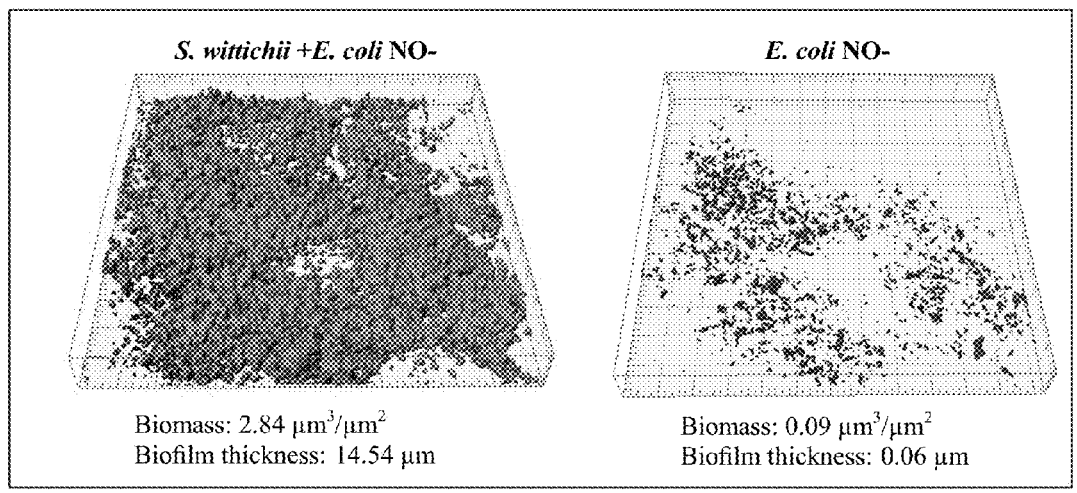
FIG. 19A-F are images of consortial biofilms of $S.$ wittchii and $E.$ coli NO-(control $E.$ coli TG1/pBdcAE50Q-lasI-lasR/bPBad) grown on NF90 membranes.
Figure 19B:
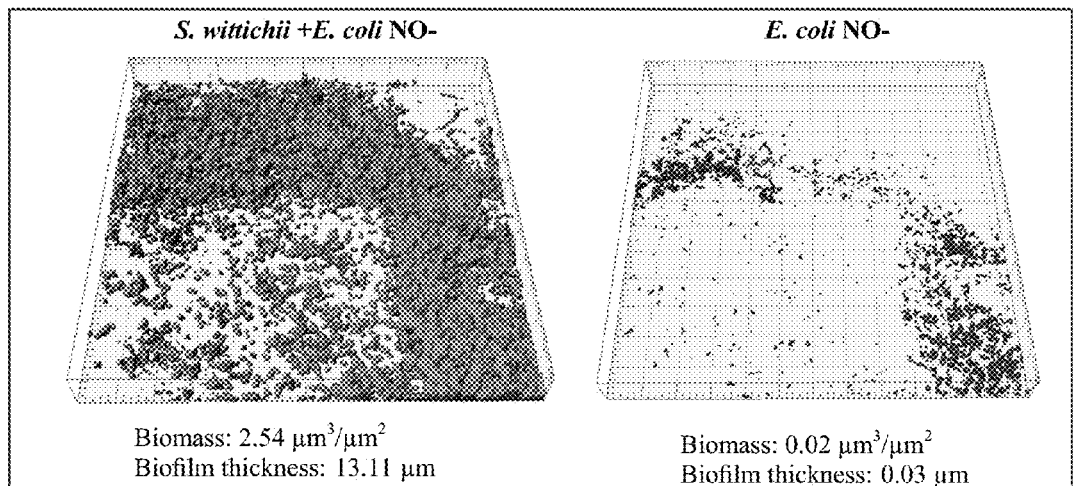
Figure 19C:
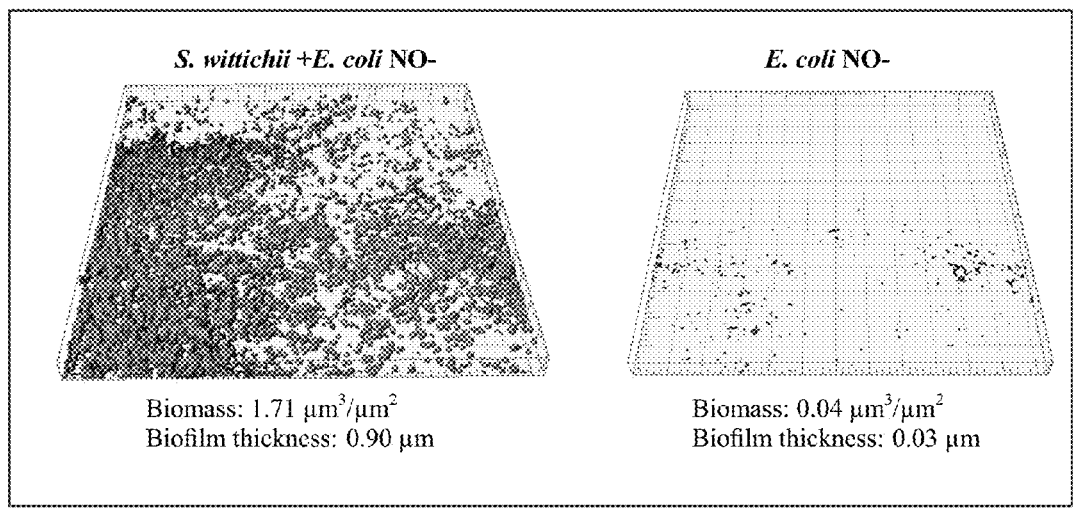
Figure 19D:
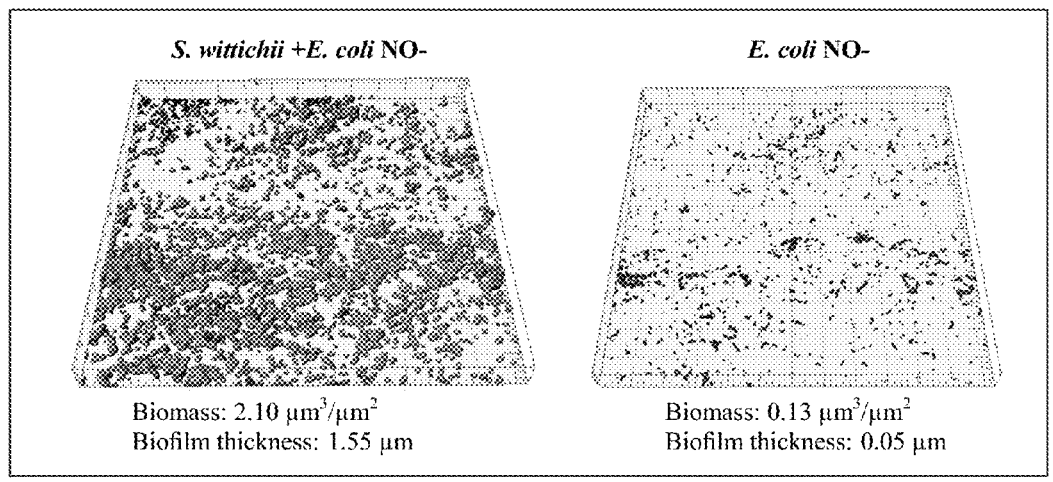
Figure 19E:
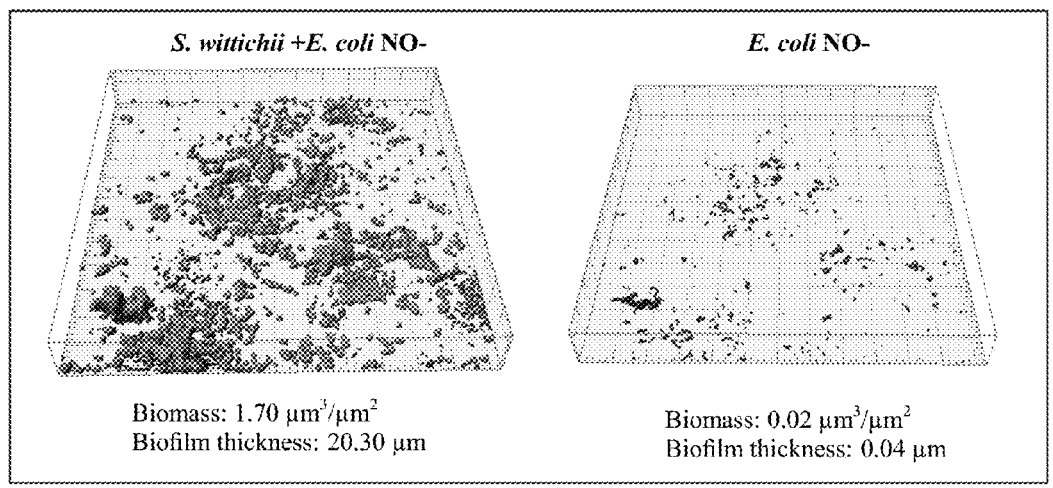
Figure 19F:
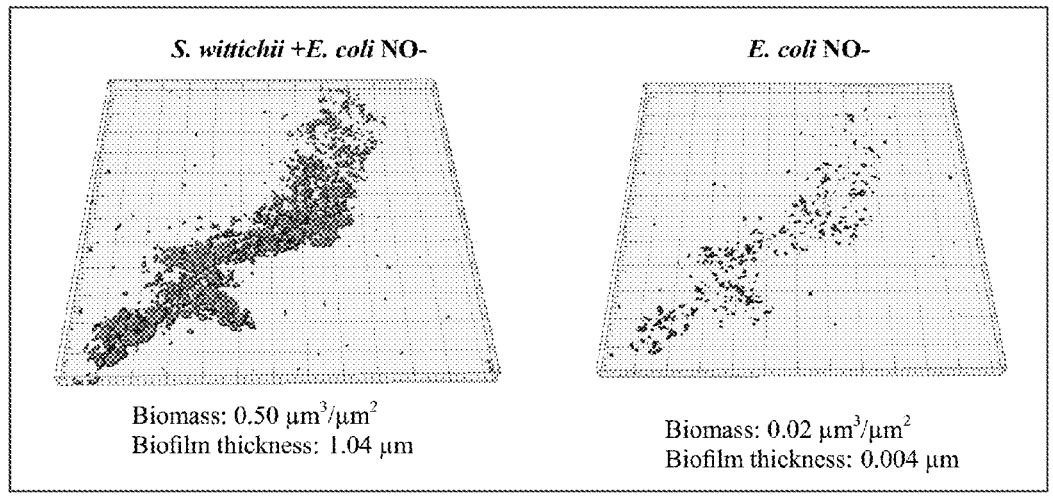
Figure 20A:
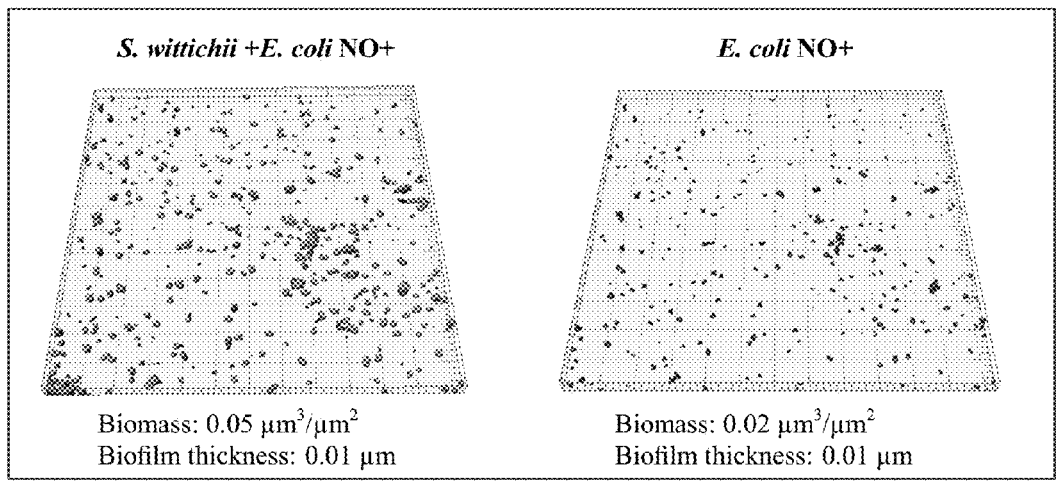
FIG. 20A-F are images of consortial biofilms of $S.$ wittchii and $E.$ coli NO-+(TG1/pBdcAE50Q-lasI-lasR/bPNos) grown on NF90 membranes.
Figure 20B:
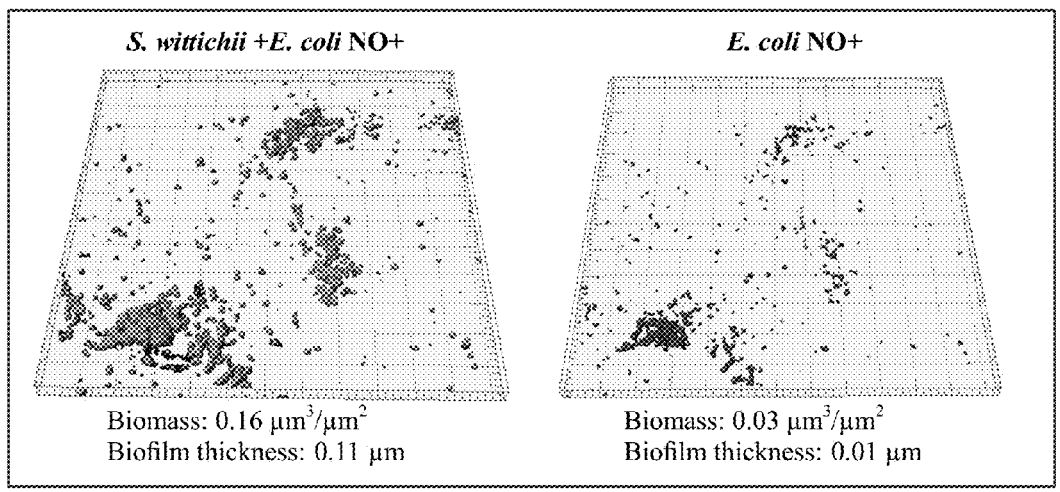
Figure 20C:
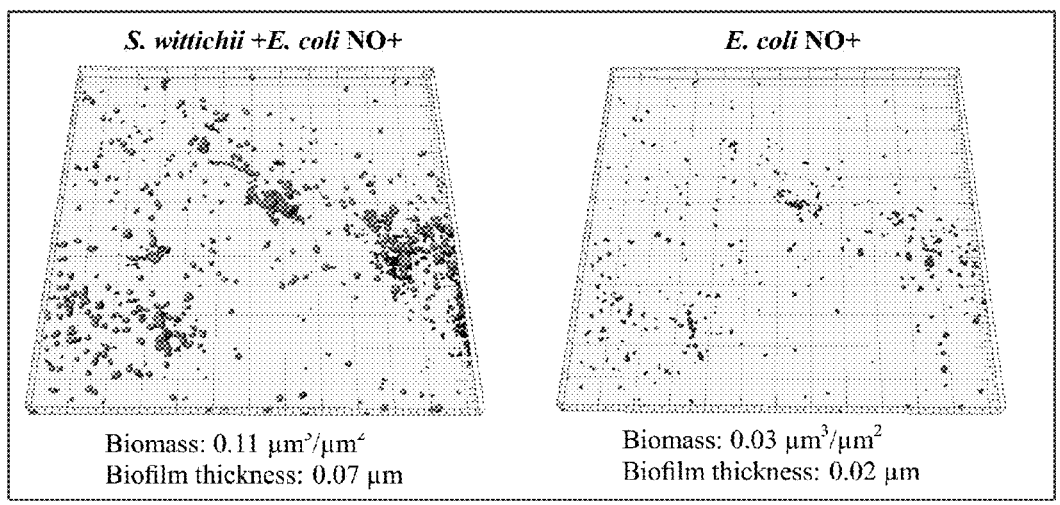
Figure 20D:
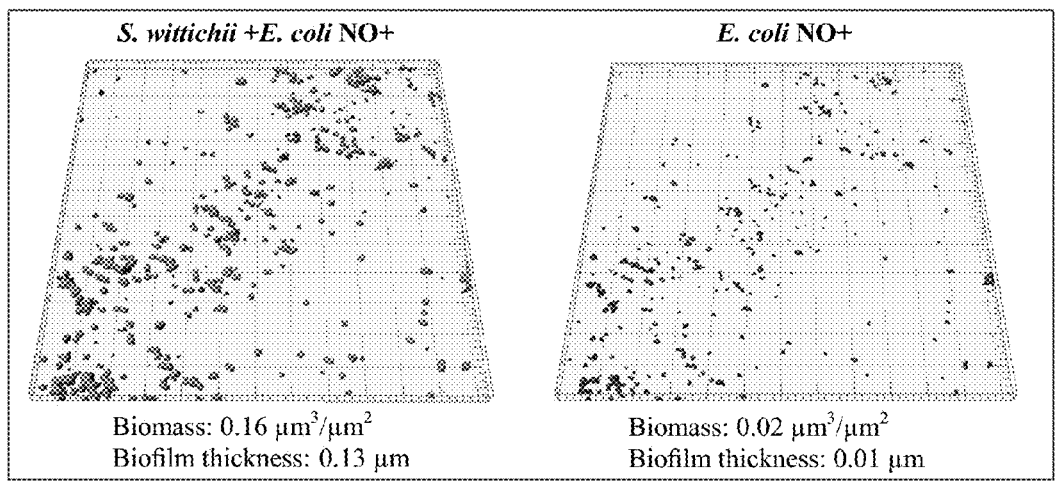
Figure 20E:
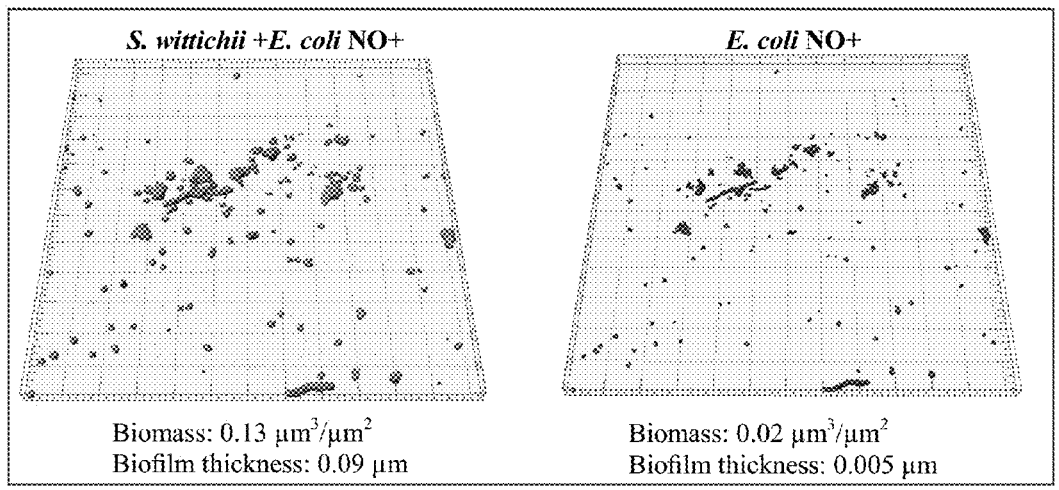
Figure 20F:
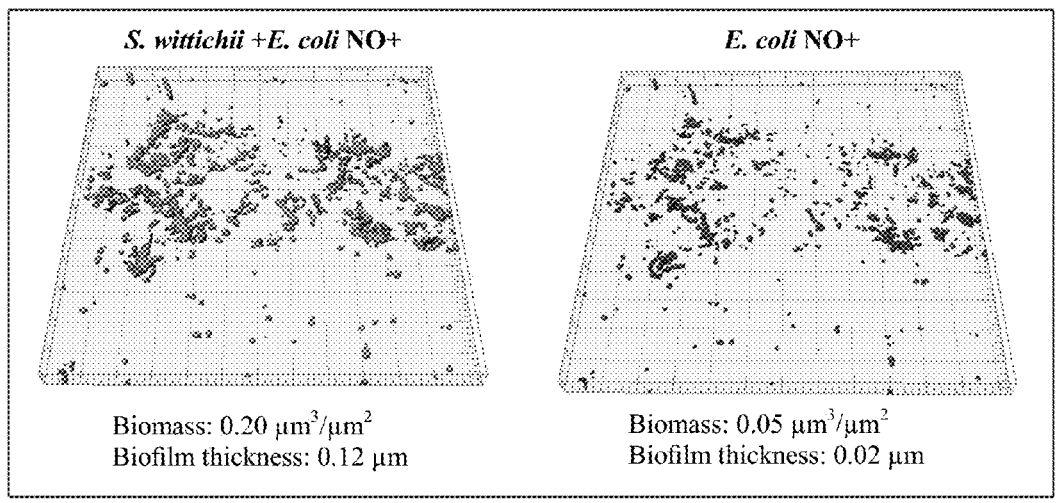
Figure 21A:
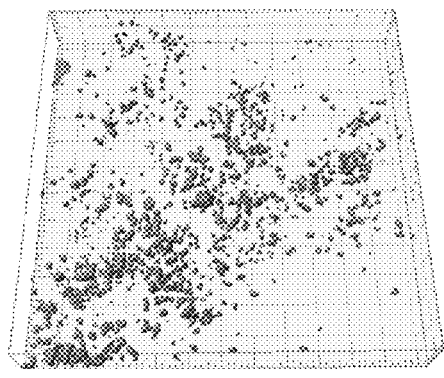
FIG. 21A-D are images of biomass where are challenged by $P.$ aeruginosa showing PAO1 consortial biofilm on NF90 membrane (A), $E.$ coli control strain no producing NO consortial biofilm (B), consortial biofilm on NF90 membrane (C), and beneficial biofilm (D).
Figure 21B:
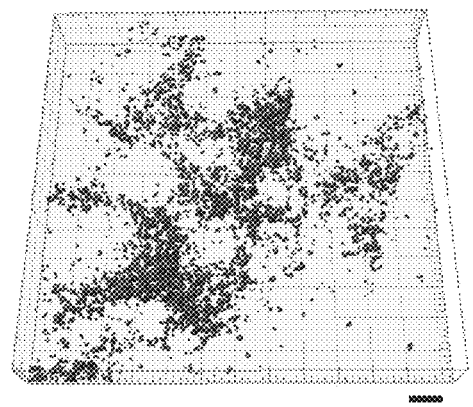
Figure 21C:
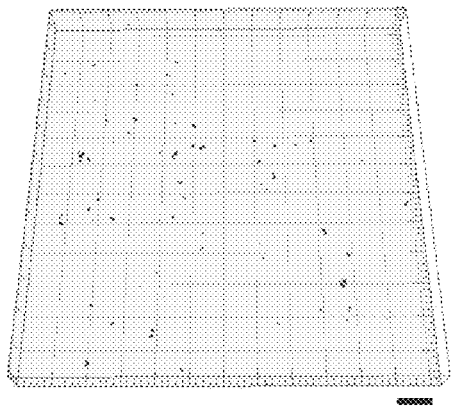
Figure 21D:
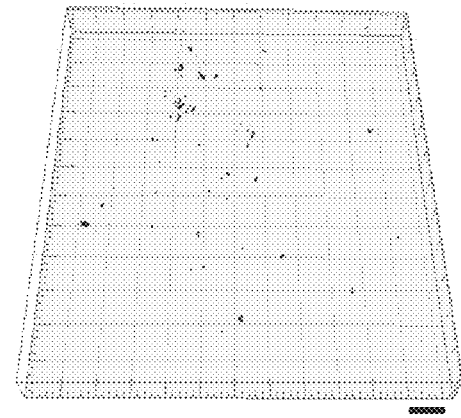

FIG. 19A-F show deconvoluted IMARIS images of consortial biofilms of *S. wittichii* and *E. coli* NO−(control, *E. coli* TG1/pBdcAE50Q-lasI-lasR/pBad) grown on NF90 membranes. The *E. coli* NO− biofilm was formed in M9G medium with Cm (300 μg/mL) and Cb (250 μg/mL) supplemented with 15 mM L-arginine and 1.6% L-arabinose for 24 h, then the medium was replaced with fresh M9G medium supplemented with 15 mM L-arginine and 1.6% L-arabinose without any antibiotics, and the membrane was challenged by the addition of *S. wittichii* for 48 h; *S. wittichii* was added at an initial turbidity of 0.5 at 600 nm. To observe the *S. wittichii/E. coli* combined biofilms (green) with confocal microscopy, the membrane samples were incubated with 5 mL of 5 μM SYTO 9 in 0.85% NaCl for 1 h under light insulated conditions to stain the total biofilm. The *E. coli* biofilms were visualized using the RFP tag. All the biomass and biofilm thickness data were quantified using COMSTAT. Each major grid bar represents 20 μm. The average of *S. wittchii+E. coli* NO− of FIG. 19A-F was biomass of 1.9 $\mu m^3/\mu m^2$, biofilm thickness of 8.6 μm; and *E. coli* NO− average was biomass of 0.05 $\mu m^3/\mu m^2$, and biofilm thickness of 0.03 μm. FIG. 19E is shown in FIG. 17. FIG. 20A-F also shows results, here where *E. coli* NO+ biofilm was formed. The average of *S. wittichii+E. coli* NO+ measurements was biomass of 0.13 $\mu m^3/\mu m^2$ and biofilm thickness of 0.09 μm; and *E. coli* NO+ average was biomass of 0.03 $\mu m^3/\mu m^2$ and biofilm thickness of 0.01 μm.

Figure 22A:
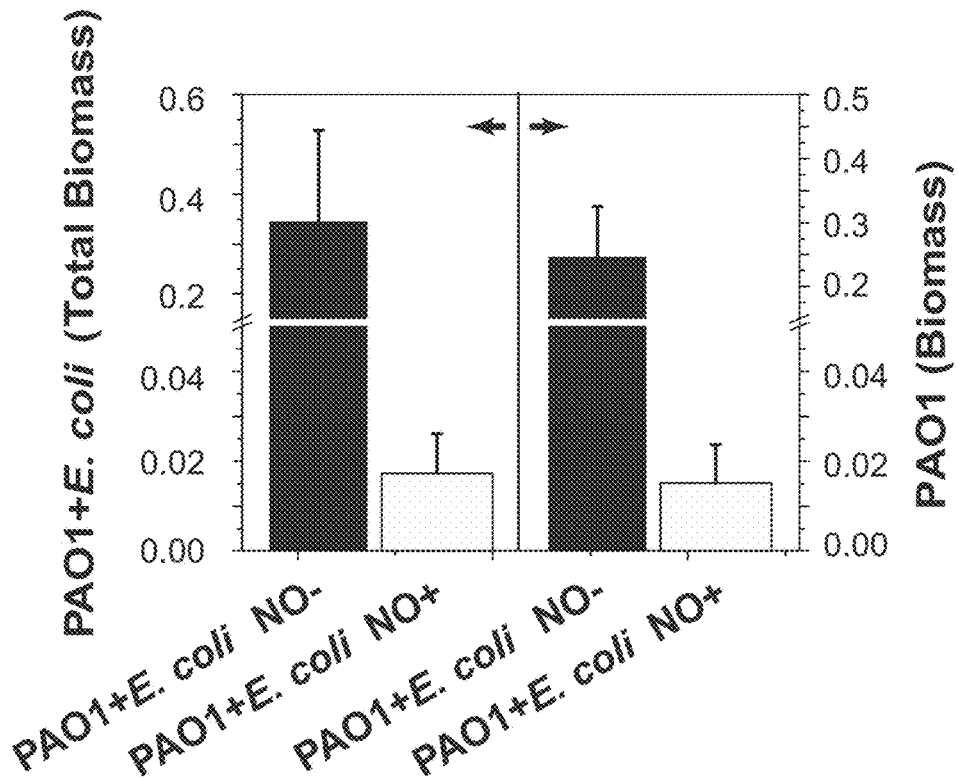
FIG. 22A-B are graphs showing total biomass and PAO1 biomass of control biofilms compared to beneficial biofilms with and without NO (A) and showing average normalized flux over time of control and beneficial strain biofilms with and without NO (B).
Figure 22B:
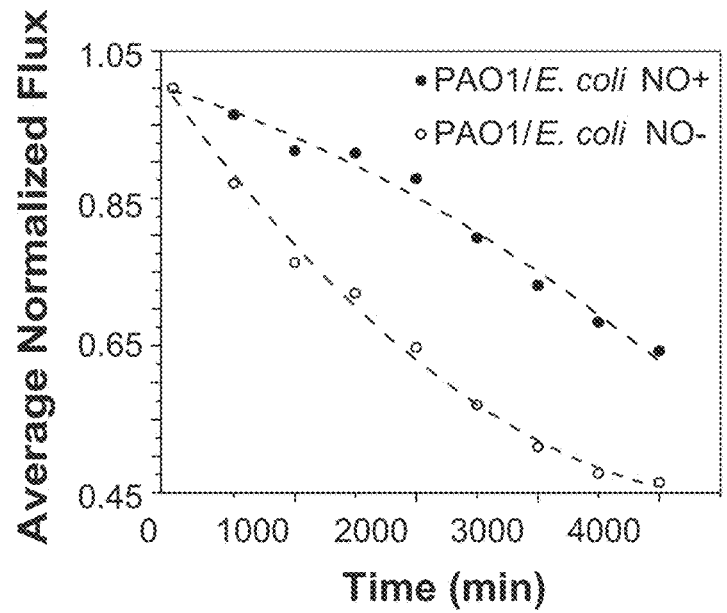
Figure 23:
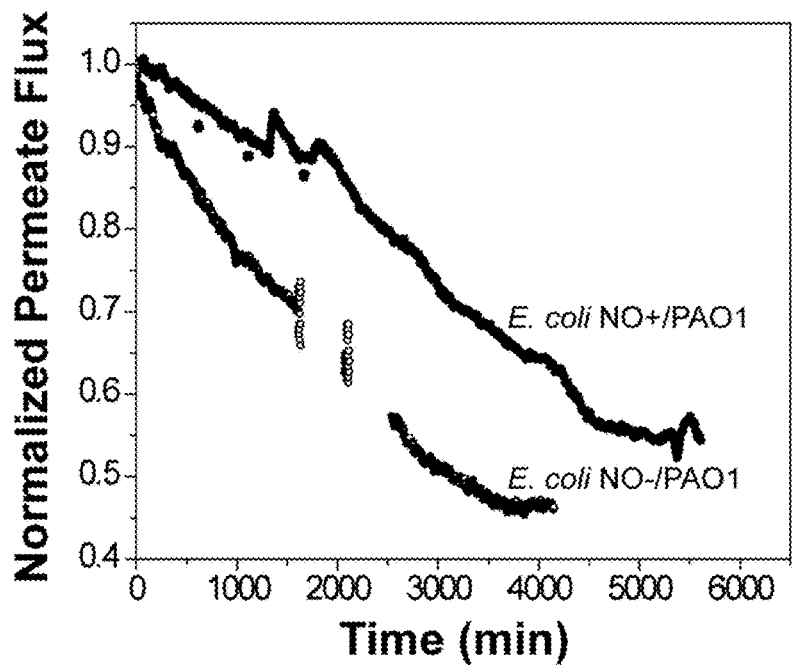
FIG. 23 is a graph showing normalized permeate flux over time of cross flow challenge with *P. aeruginosa* PAO1 with control and beneficial strains with a feed spacer.
Figure 24:
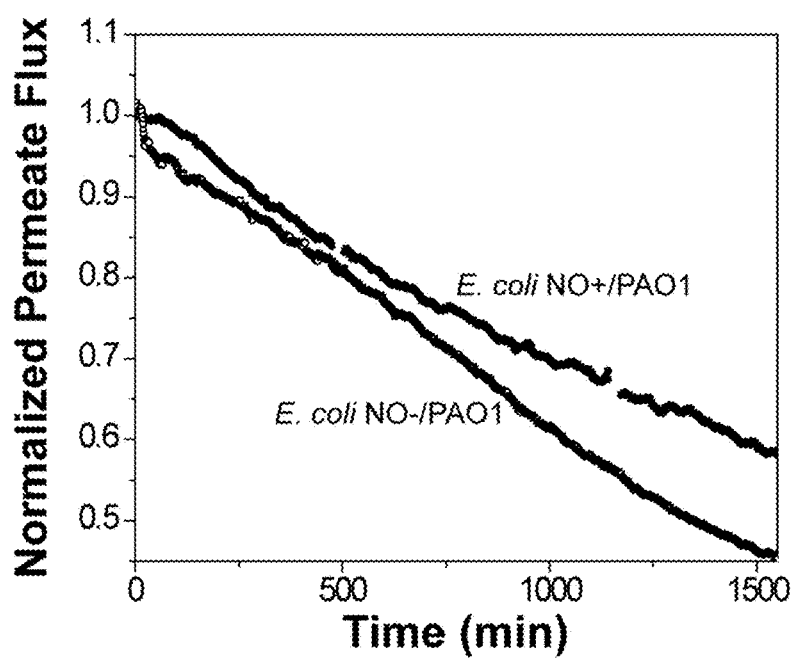
FIG. 24 is a graph showing normalized permeate flux over time of cross flow challenge experiments with *P. aeruginosa* PAO1 with control and the beneficial strain without a feed spacer under increased microbial load over time.

We also conducted long-term, crossflow filtration challenge tests to determine the robustness of our approach under shear and pressure conditions typically seen in spiral-wound membrane systems operating at plant scales. We conducted these tests (2 to 5 days leading to substantial productivity declines reaching over 50%) with a well-validated crossflow system (Osmonics SEPA® Cell) with Dow NF90 membranes and a computerized control system built to allow operation at constant pressure. In all experiments, the membranes were first conditioned with either the control strain (self-controlled strain but with no release capabilities, "*E. coli* NO−", TG1/pBdcAE50Q-lasI-lasR/pBad) or the beneficial strain (self-controlled strain with NO release capabilities, "*E. coli* NO+", TG1/pBdcAE50Q-lasI-lasR/pBNos) for 24 hours in crossflow mode but with minimal permeation by maintaining a transmembrane pressure of 40 psi. The system conditioned with control biofilms (*E. coli* NO−) showed rapid flux decline in 4000 minutes (~3 days) to ~55% of initial flux, while the beneficial biofilm restricted the flux decline to ~34%, a decrease of ~40% (FIG. 22). Critically, the beneficial biofilm enhanced membranes could be run for ~4 days under challenge conditions without the flux decline reaching 50%. (See FIG. 23 showing real time flux behavior of crossflow challenge experiments with *P. aeruginosa* PAO1 with control (*E. coli* NO−, TG1/pBdcAE50Q-lasI-lasR/pBad) and beneficial strains (*E. coli* NO+, TG1/pBdcAE50Q-lasI-lasR/pBNos) with a feed spacer. *E. coli* biofilms were formed for 24 h on NF90 membranes with M9G medium, Cm (300 μg/mL) and Cb (250 μg/mL) under cross flow conditions at ~40 psi and 27° C. without filtration at an initial $OD_{600\ nm}$ of 0.01. PAO1 was introduced along with fresh M9G medium with Cm (300 μg/mL) and Cb (250 μg/mL) supplemented with 1.6% arabinose, and 15 mM L-arginine into the feed tank at time t=0 min and at an initial $OD_{600\ nm}$ of 0.002. There is significant difference for flux values between the *E. coli* NO+ and *E. coli* NO− biofilm covered membranes due to nitric oxide-mediated dispersal of the *P. aeruginosa* PAO1 biofilms by the former strain under similar hydrodynamic conditions. In these experiments the conditioning biofilms were started with an initial *E. coli* turbidity at 600 nm of 0.01 in the system feed and challenged with *P. aeruginosa* PAO1 at an initial turbidity of 0.002 in the system feed. Another set of experiments was conducted with higher microbial loads (initial conditioning films with *E. coli* turbidity of 0.05 and *P. aeruginosa* PAO1 at a turbidity of 0.01) and led to similar differences in flux decline but over a shorter time scale (~24 h of challenge, FIG. 24). See FIG. 24 for a showing of real time flux behavior of crossflow challenge experiments with *P. aeruginosa* PAO1 with the control (*E. coli* NO−, TG1/pBdcAE50Q-lasI-lasR/pBad) and the beneficial strain (*E. coli* NO+, TG1/pBdcAE50Q-lasI-lasR/pBNos) without a feed spacer under increased microbial load and in the absence of a feed spacer. *E. coli* biofilms were formed for 24 h on NF90 membranes with M9G medium, Cm (300 μg/mL) and Cb (250 μg/mL) under crossflow conditions at ~40 psi and 27° C. without filtration at an initial $OD_{600\ nm}$ of 0.05. PAO1 was introduced along with fresh M9G medium with Cm (300 μg/mL) and Cb (250 μg/mL) supplemented with 1.6% arabinose, and 15 mM L-arginine into the feed tank at time t=0 min and at an initial $OD_{600\ nm}$ of 0.01. The flux decline ~1500 minutes is similar in magnitude to flux decline with a spacer ~4000 minutes. This rapid flux decline can be attributed to more biofilm formation and less mixing in the absence of a spacer.

Biofilm analysis of the membranes subjected to the long-term, crossflow (3 to 4 days) tests corroborated the permeate flux results in that an order of magnitude less colonization of the membranes was seen by the challenge organisms (*P. aeruginosa* PAO1) when the membranes were conditioned by the beneficial biofilm (*E. coli* NO+) compared to when membranes were conditioned by the control biofilm (*E. coli* NO−) (FIG. 22). The total biomass for the beneficial biofilm conditioned membranes challenged by *P. aeruginosa* PAO1 was limited to 0.017 (±0.001) $\mu m^3/\mu m^2$ while it was 0.35 (±0.02) $\mu m^3/\mu m^2$ for the membranes conditioned by control biofilms. Since both of these biofilms (control and beneficial) were based on the self-controlled LasI/LasR system, the overall biofilm formation was limited as expected. The biomass values of the control strain alone was ~0.10 $\mu m^3/\mu m^2$ (i.e., the difference between the total biomass and the *P. aeruginosa* PAO1 biomass) at the end of ~4 days, similar to that seen after 1 day for the batch experiments (FIG. 7, ~0.20 $\mu m^3/\mu m^2$) indicating the self-controlled strain was maintained.

Figure 25A:
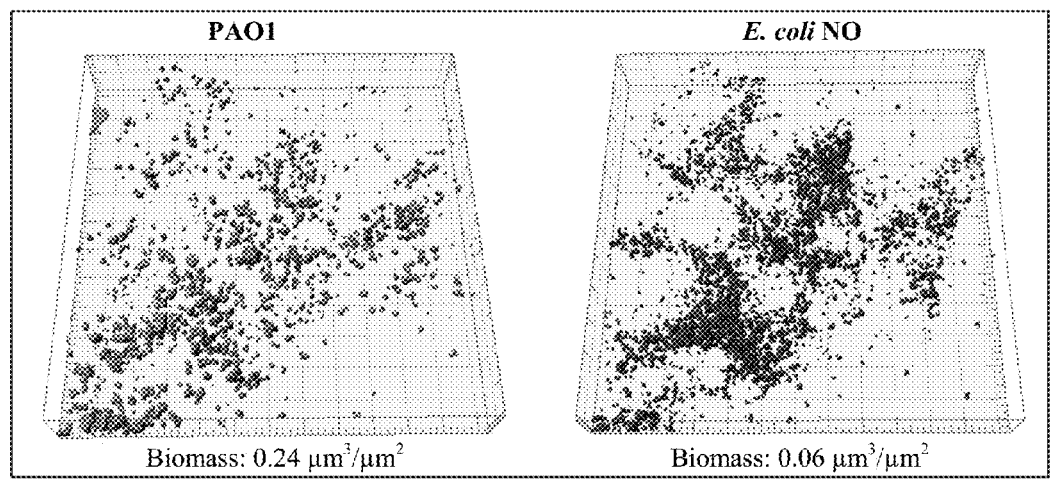
FIG. 25A-F are images showing consortial biofilms. of *P. aeruginosa* PAO1/pMRP9-1 and *E. coli* NO−.
Figure 25B:
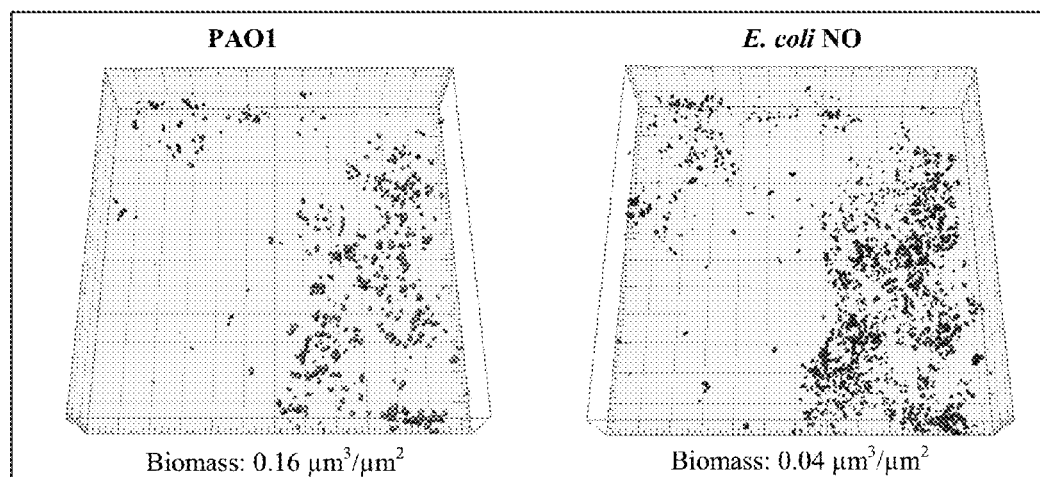
Figure 25C:
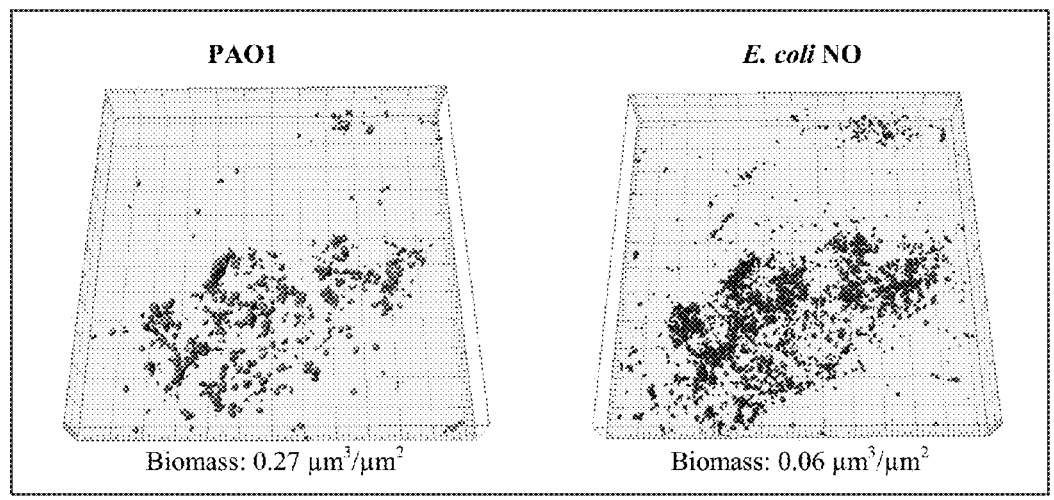
Figure 25D:
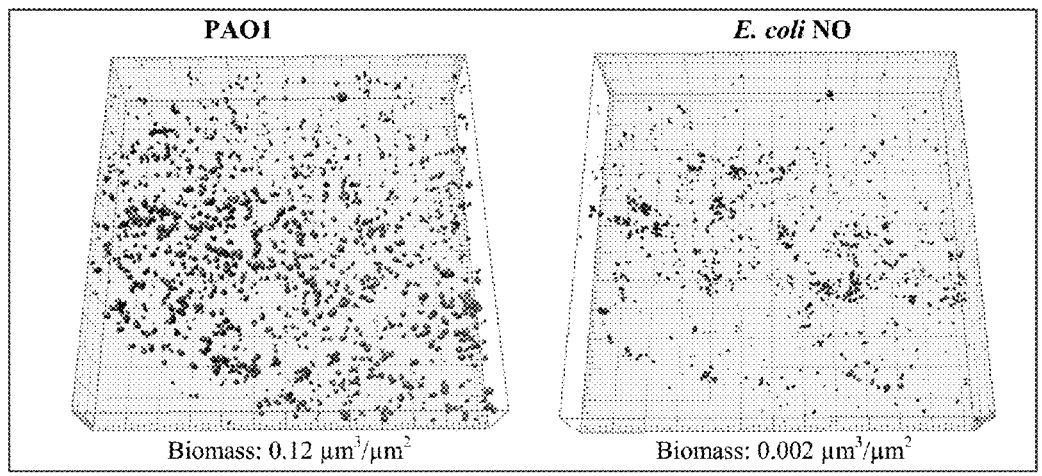
Figure 25E:
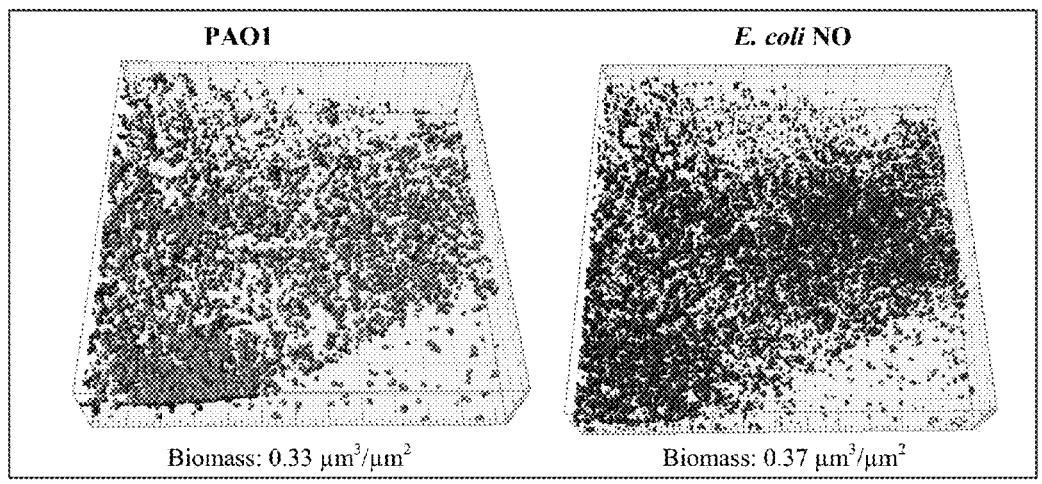
Figure 25F:
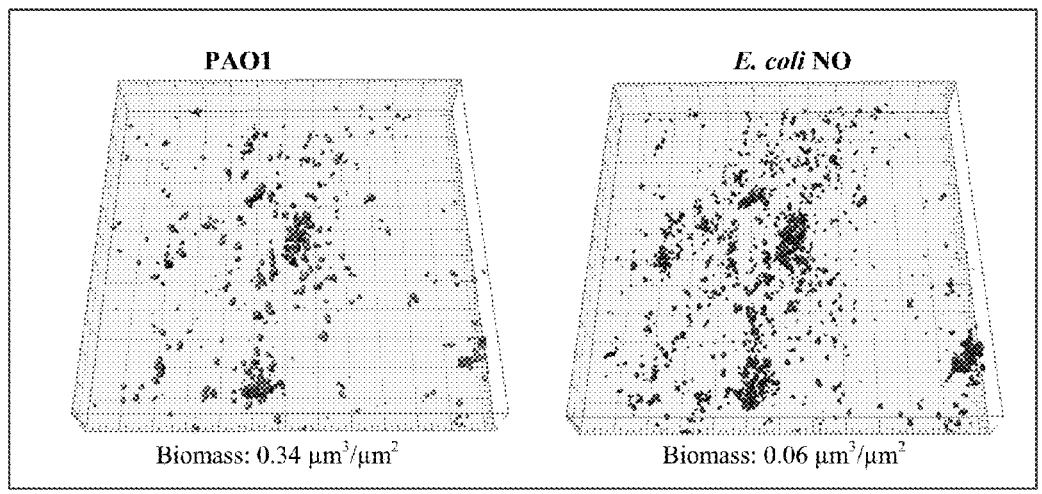
Figure 26A:
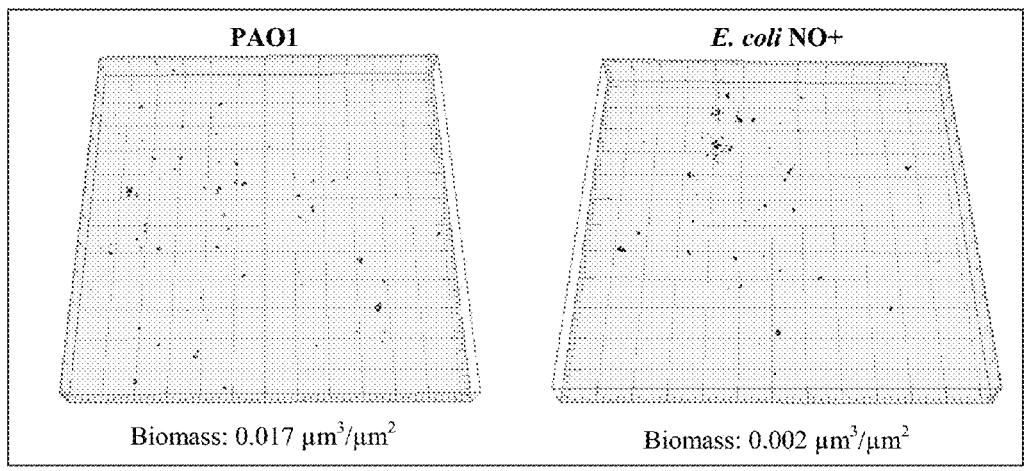
FIG. 26 A-F are images of consortial are images showing consortial biofilms. of *P. aeruginosa* PAO1/pMRP9-1 and *E. coli* NO+.
Figure 26B:
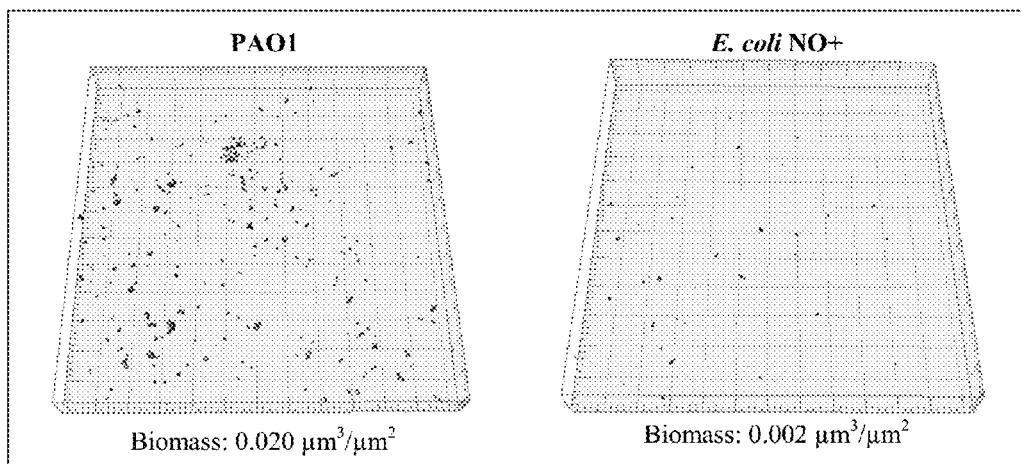
Figure 26C:
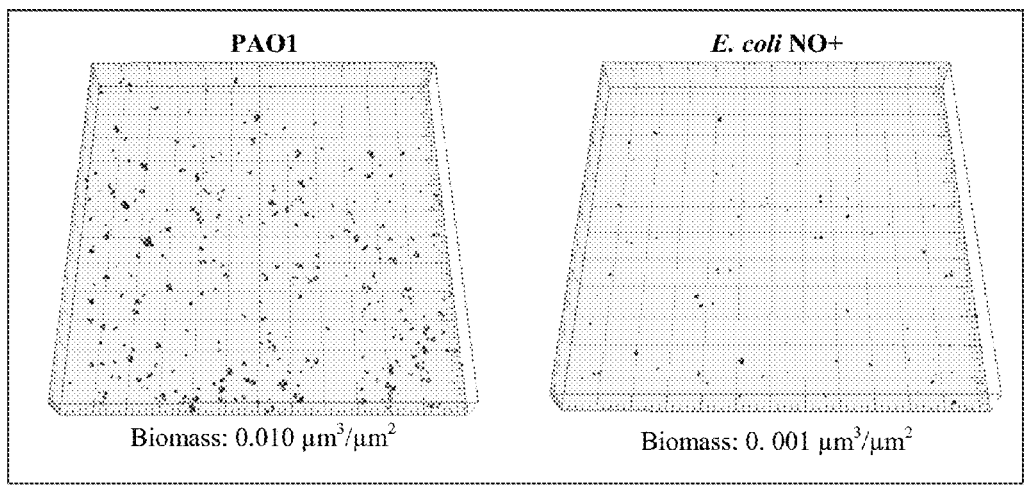
Figure 26D:
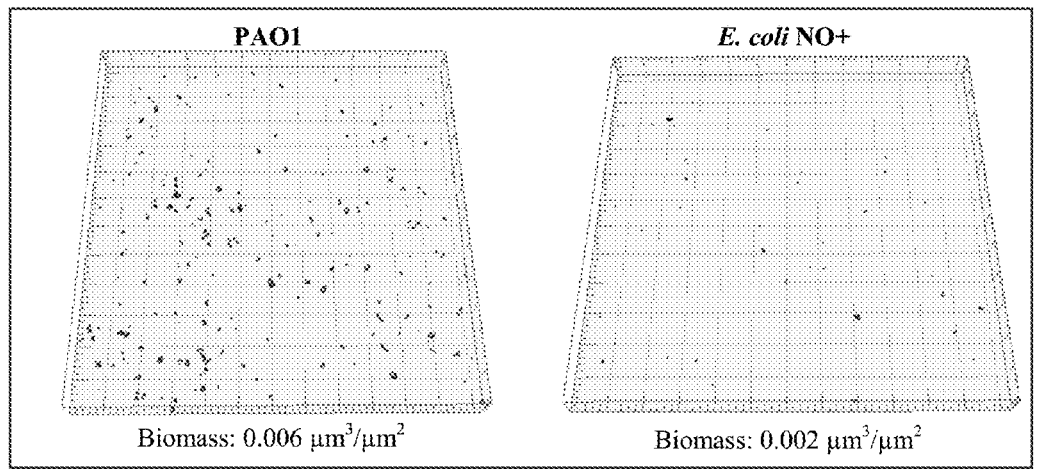
Figure 26E:
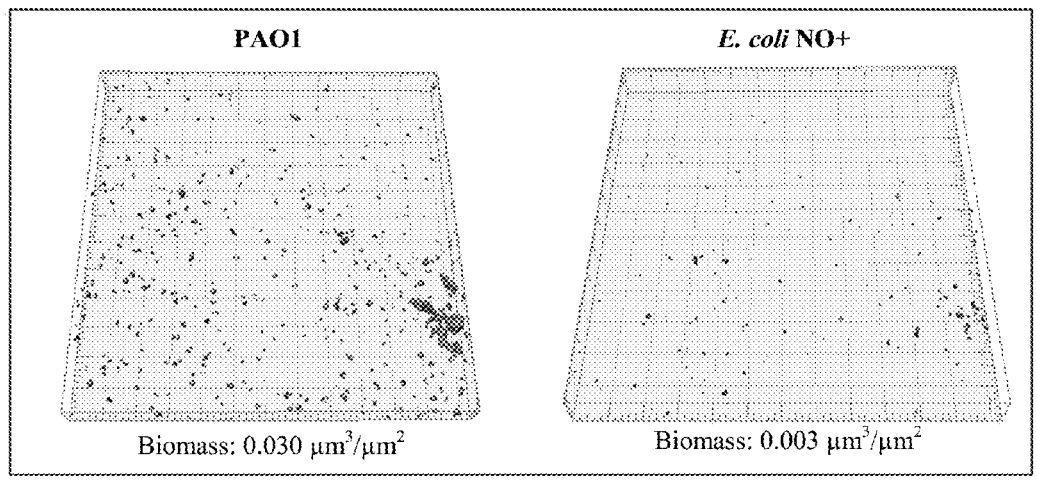
Figure 26F:
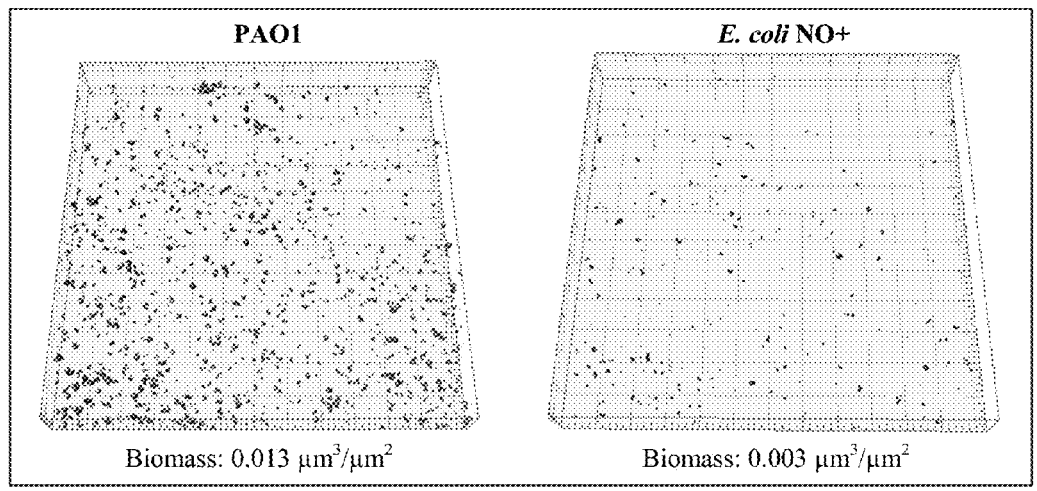

FIG. 24A-F shows deconvoluted IMARIS images of consortial biofilms of PAO1 (*P. aeruginosa* PAO1/pMRP9-1) and *E. coli* NO–(control, TG1/pBdcAE50Q-lasI-lasR/pBad) grown on NF90 membranes (crossflow conditions). The *E. coli* NO– biofilm was formed in M9G medium with Cm (300 µg/mL) and Cb (250 µg/mL) with an initial $OD_{600\,nm}$ of 0.01 for 24 h at 40 psi under crossflow conditions and then challenged by the addition of PAO1 with fresh M9G medium with Cm (300 µg/ml) and Cb (250 µg/ml) supplemented with 15 mM L-arginine and 1.6% L-arabinose for another 72 h at an initial $OD_{600\,nm}$ of 0.002 and at 200 psi under cross flow conditions. All the biomass and biofilm thickness data were quantified using COMSTAT. Each major grid bar represents 20 µm. FIG. 25A was shown in FIG. 22. Average biomass measured of PAO1 NO– was 0.24 $\mu m^3/\mu m^2$ and *E. coli* NO– was 0.10 $\mu m^3/\mu m^2$. FIG. 26A-F shows images with *E. coli* NO+ biofilm formed. Image 1 was shown in FIG. 5. Average biomass of PAO1 NO+ was 0.015 $\mu m^3/\mu m^2$ and of *E. coli* NO+ was 0.002 $\mu m^3/\mu m^2$.

Figure 27:
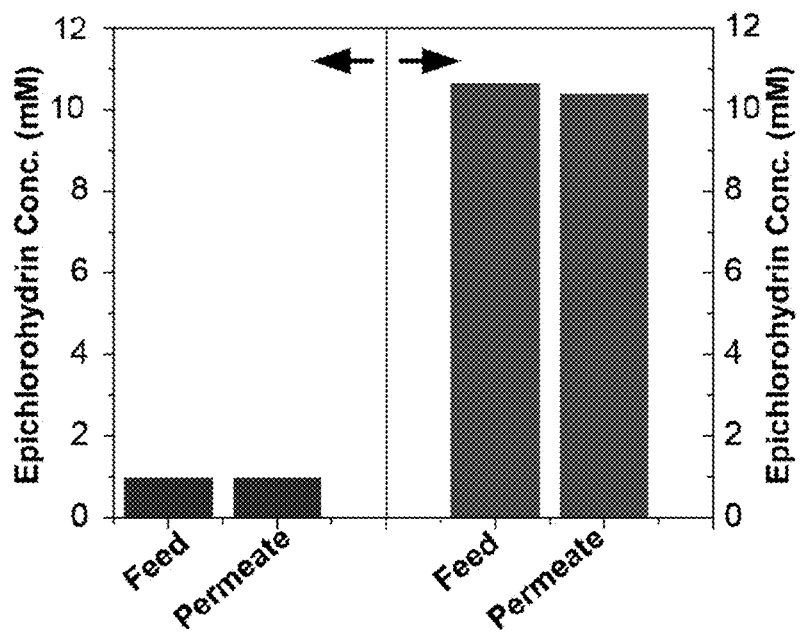
FIG. 27 is a graph showing epichlorohydrin concentration with NF90 membranges with 1 mM (left half) and 10 mM (right half) epichlorohydrin fee concentrations.
Figure 28:
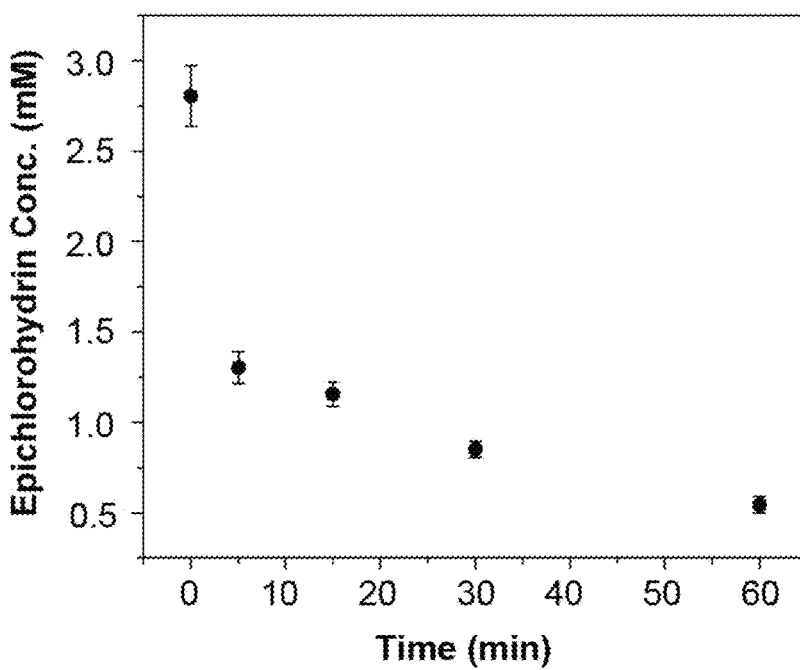
FIG. 28 is a graph showing epichlorohydrin concentration over time as degraded by the beneficial strain.

Beneficial Biofilm Degrades Epichlorohydrin. Epichlorohydrin is an emerging water contaminant for which treatment techniques are not well studied. Further, this small hydrophobic compound passes through the membrane used. (See FIG. 27 showing rejection experiments conducted with NF90 membranes (no biofilm) with 1 mM (left half) and 10 mM (right half) epichlorohydrin feed concentrations. Measurements were taken 30 min after permeation began. Feed was in 5 mM NaCl (pH 9.0). To add to the ability of the beneficial biofilm to simultaneously perform bioremediation while preventing biofouling, the beneficial biofilm was engineered to produce an engineered EH that degrades epichlorohydrin[28]. As planktonic cultures, the beneficial strain that produces EH (*E. coli* TG1/pBdcAE50Q-lasI-lasR/pBNos-echA) degraded epichlorohydrin at a rate of 3.7±0.4 nmol/min/mg of protein (See FIG. 28) whereas there was no epichlorohydrin degradation in the control strain that lacks EH (*E. coli* TG1/pBdcAE50Q-lasI-lasR/pBNos). FIG. 28 shows rejection experiments conducted with NF90 membranes (no biofilm) with 1 mM (left half) and 10 mM (right half) epichlorohydrin feed concentrations. Measurements were taken 30 min after permeation began. Feed was in 5 mM NaCl (pH 9.0). Furthermore, when grown on the NF90 membrane, the beneficial biofilm that produces EH degraded epichlorohydrin by more than 39±4% in single pass batch filtration (See FIGS. 29 and 30). FIG. 30 shows biofilms that produce epoxide hydrolase degrade epichlorohydrin in a single pass through NF90 membrane. Biofilms grown for 24 h on NF90 membranes were challenged with 10 mM epichlorohydrin in 5 mM NaCl feed solution (pH 9). The left and adjacent right bars indicate the molar removal of epichlorohydrin (%) at 20 min and 30 min respectively, after starting filtration. The removal of epichlorohydrin by adsorption to cellular biomass was estimated using a dead cell control experiment. EH– is *E. coli* TG1/pBdcAE50Q-lasI-lasR/pBNos and EH+ is *E. coli* TG1/pBdcAE50Q-lasI-lasR/pBNos-echA. Dead cells were obtained by autoclaving overnight cultures of the EH+ strain. The error bars are standard deviation for three independent colonies.

Therefore, the beneficial biofilm that produces EH is capable of degrading the environmental pollutant epichlorohydrin while controlling its own biofilm formation and limiting the biofilm formation of deleterious strains.

Figure 29A:
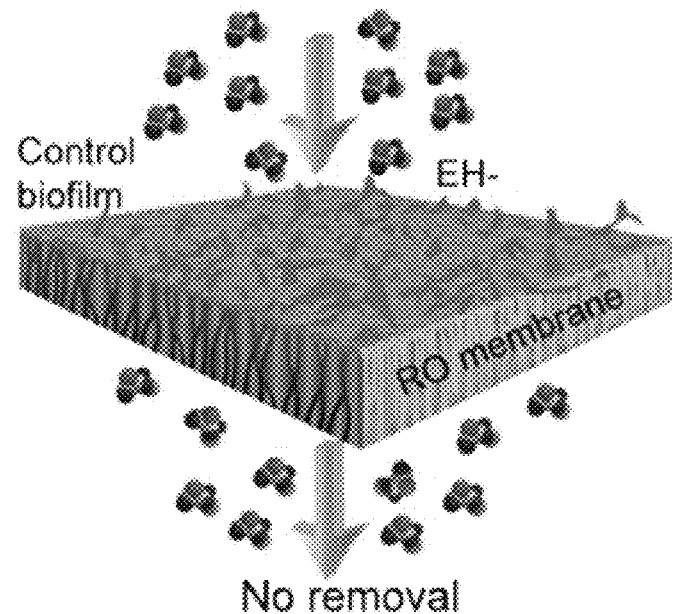
FIG. 29A-B are graphics showing testing of ephichlorohydrin removal on control biofilm (A) and the self-controlled biofilm (B).
Figure 29B:
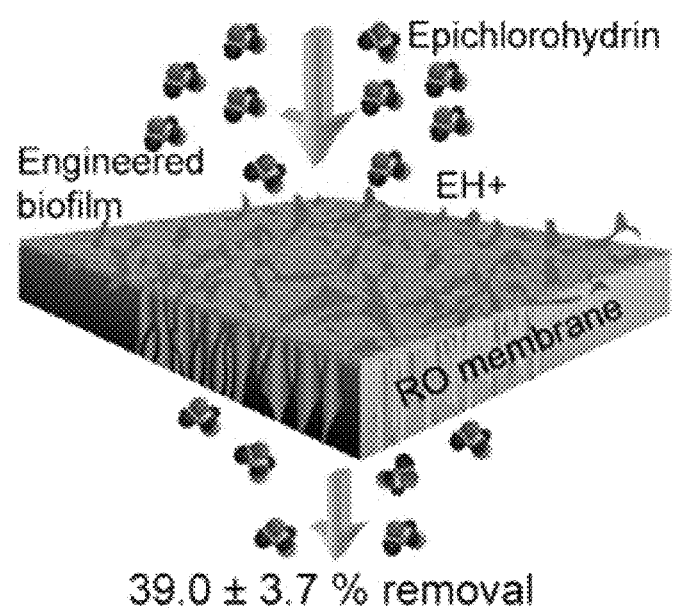
Figure 30:
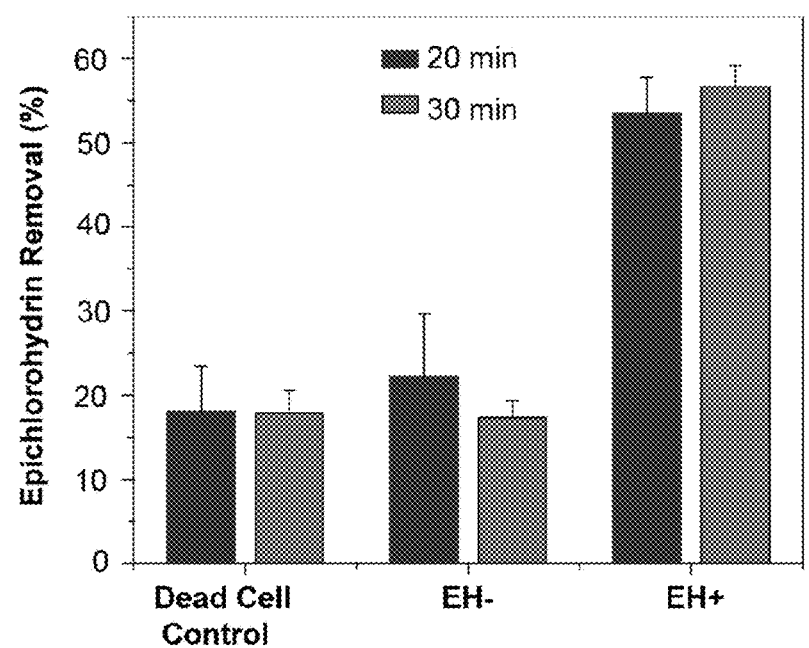
FIG. 30 is a graph showing ephichlorohydrin removal the first bar shows rmolar1 removal at 20 minutes and the adjacent bar to the right shows removal at 30 minutes after starting filtration. EH− is *E. coli* TG1/pBdcAE50Q-lasI-lasR/pBNos and EH+ is *E. coli* TG1/pBdcAE50Q-lasI-lasR/pBNos-echA.

In detail, see FIG. 29. Epichlorohydrin removal was tested using biofilms of *E. coli* (TG1/pBdcAE50Q-lasI-lasR/pBNos (EH–) and *E. coli* TG1/pBdcAE50Q-lasI-lasR/pBNos-echA (EH+)) developed in 24 h on NF90 membranes in M9G medium with 15 mM arginine and 1.6% arabinose. The control biofilm was challenged with 10 mM epichlorohydrin in 5 mM NaCl feed solution (pH ~9.0). Epichlorohydrin adsorption to the cellular biomass was subtracted from the total removal amount to determine the actual enzymatic removal levels shown here (FIG. 27). In FIG. 29A no enzymatic removal was observed with the control biofilm of *E. coli* TG1/pBdcAE50Q-lasI-lasR/pBNos (EH–) on RO membranes. See FIG. 29 (*b*) where removal of epichlorohydrin by beneficial biofilm (*E. coli* TG1/pBdcAE50Q-lasI-lasR/pBNos-echA or EH+) was 39% at 30 min after the filtration began under similar process and feed conditions. The error values are standard deviation for three independent colonies.

Here is demonstrated a novel approach for combating biofouling in membrane systems by using the feature of biofilms that makes them a challenge in many systems, their persistence, in a beneficial manner. We further developed the biofilm into a platform for treating pollutants such as refractory pollutants that escape or are modified through the upstream treatment process and can even pass through RO membranes. Currently micropollutants that pass through NF and RO membranes, such as N-nitrosodimethylamine[33] and 1,4-dioxane[34], have to be treated using even more advanced techniques such as high intensity ultraviolet radiation[35]. The approach proposed can be extended to other membrane technologies such as membrane bioreactors and forward osmosis for contaminant degradation and biofouling prevention. It may also be extended to industrial and biomedical settings with proper controls on engineered biofilm proliferation. Additional industrial settings include biofilms in cooling towers, water distribution systems as well as in building HVAC systems (implicated in Legionnaires' disease[36, 37]). Biomedical applications include biofilm prevention in medical catheters[38], biomedical implants[39], and biofilm-related human diseases[40] such as cystic fibrosis[41], endocarditis[42], dental plaque[43] and chronic rhinosinusitis[44]. The use of beneficial biofilms to combat biofilm related diseases could reduce the use of antibiotics and help combat the rise of antibiotic resistance. Treatment of antibiotic resistant *Helicobacter pylori* infection is relevant in this context[45], since, the first line of antibiotics is proving increasingly ineffective against *H. pylori* biofilms[46], and the beneficial biofilm after suitable modifications, could possibly be used as an alternative treatment strategy. Overall, the general scheme we developed has the potential for combating many problems that arise due to uncontrolled proliferation of bacteria in biofilms.

Methods

Bacterial Strains and Culture Conditions. All strains and plasmids used are summarized in Table 1. All strains were grown in lysogeny broth (LB)[47] or minimal medium with 0.4% glucose (M9G)[48] at 37° C. Chloramphenicol (Cm) 300 µg/mL was used to maintain pCA24N-based plasmids in *E. coli*, carbenicillin (Cb) 250 µg/mL was used to maintain pBad in *E. coli*, and Cb (250 µg/mL) was used to maintain pMRP9-1 in *P. aeruginosa* PAO1. During co-culture with *E. coli*, *P. aeruginosa* was grown with Cm (300 µg/mL) since it is naturally-resistant to this antibiotic.

TABLE 1

Bacterial strains and plasmids used. $Cm^R$ and $Cb^R$ denote chloramphenicol and carbenicillin resistance, respectively.

| Strains or plasmids | Description | Source |
|---|---|---|
| Strains | | |
| E. coli TG1 | supE thi-1 Δ(lac-proAB) Δ(mcrB-hsdSM)5, $(r_K^- m_K^-)$ F' [traD36 proAB⁺ lacI^q lacZΔM15] | 48 |
| P. aeruginosa PAO1-UW | Wild-type from University of Washington | 53 |
| Plasmids | | |
| pHha13D6-gfp-lasI | $Cm^R$; lacI^q, pCA24N $P_{T5\text{-}lac}$::hha13D6⁺ | 31 |
| pBdcAE50Q | $Cm^R$; lacI^q, pCA24N $P_{lasI}$::bdcAE50Q⁺ | 31 |
| pBdcAE50Q-rfp-lasR | $Cm^R$; lacI^q, pCA24N $P_{lasI}$::bdcAE50Q⁺ $P_{CP25}$::rfp⁺-lasR⁺ | 31 |
| pBdcAE50Q-lasI-lasR | $Cm^R$; lacI^q, pCA24N $P_{lasI}$::bdcAE50Q⁺-lasI⁺ $P_{CP25}$::rfp⁺-lasR⁺ | This study |
| pBNos | $Cb^R$; pBad $P_{Ara}$::nos⁺ | 21 |
| pBNos-echA | $Cb^R$; pBad $P_{Ara}$::nos⁺- echA(F108L/I219L/C248I)⁺ | This study |
| pBad/Myc-HisB | $Cb^R$; araC | Invitrogen |
| pMRP9-1 | $Cb^R$; pUCP18 carrying a gene encoding enhanced green fluorescent protein (GFP) | 54 |

Plasmid Construction. Plasmid pBdcA E50Q-lasI-lasR contains bdcAE50Q[30] and lasI under the control of lasI promoter and rfp and lasR under the control of the constitutive CP25 promoter. lasI (See, UniProt LASI_PSEAE (as in *Pseudomonas aeruginosa* Ref. P33883)) was amplified from pHha13D6-gfp-lasI[31] using the lasI-SalI-f and lasI-HindIII-r primers (Table 2) and cloned into pBdcAE50Q[31] at the SalI and HindIII restriction sites to form pBdcAE50Q-lasI. The constitutive promoter CP25, rfp (UniProt RFP_DISSP (as in Q9U6Y8, Red fluorescent protein)), and lasR (UniProt LASR PSEAE (as in P25084 Transcriptional activator protein LasR)) fragment was obtained by digesting the pBdcAE50Q-rfp-lasR plasmid[31] with BlpI and was inserted into the pBdcAE50Q-lasI plasmid at BlpI site downstream of lasI gene to form pBdcAE50Q-lasI-lasR.

To construct pBNos-echA plasmid, the echA gene was amplified by PCR using pBSKan (EH, F108L/I219L/C2481)[28] as the template with the EH HindIII forward and EH SalI reverse primers (Table 2). The PCR products were double digested with HindIII-HF and SalI-HF and ligated into pBNos[21] yielding pBNos-echA.

All plasmids were verified by DNA sequencing. The oligonucleotides were synthesized by Integrated DNA Technologies (Coralville, Iowa).

Biofilm Formation Assay Using Crystal Violet. Biofilm formation was assayed in 96-well polystyrene plates using 0.1% crystal violet staining as described previously[49] with some modifications. Diluted overnight cultures at an initial turbidity at 600 nm of 0.05 were inoculated into 96-well-plates with M9G with appropriate antibiotics and the bacteria were cultured for 24 h at 37° C. without shaking. After the crystal violet was added to each well, the wells were rinsed and dried, and ethanol was added to dissolve the crystal violet. The total biofilm formation samples were measured at 540 nm, whereas cell growth was measured at 620 nm. Biofilm formation was normalized by the bacterial growth to reduce any growth effect. At least three independent cultures were used for each strain.

Biofilm Formation Assay Using Confocal Microscopy. The overnight cultures were diluted to an initial turbidity at 600 nm of 0.05 and thereafter, inoculated into glass bottom dishes (catalog number 150680, Nunc, Thermo Scientific) in M9G for 24 h at 37° C. without shaking. Fresh M9G medium 1 mL was added into the dishes, and they were incubated for another 24 h at 37° C. For the biofilm experiments with *P. aeruginosa*, diluted overnight cultures of *E. coli* (turbidity at 600 nm of 0.01) were inoculated into

TABLE 2

Oligonucleotides used for cloning and sequencing. All restriction enzyme sites are underlined. "f" indicates forward primer and "r" indicates reverse primer.

| Primer name | Sequence (5'→3') |
|---|---|
| Cloning | |
| lasI-SalI-f | GCTGAGCTTCTTCA<u>GTCGAC</u>TATTTGGA (SEQ ID NO: 1) |
| lasI-HindIII-r | AAGCTCAGCA<u>AAGCTT</u>CGTCATGAAACCGCC (SEQ ID NO: 2) |
| EH HindIII-f | ATAGC<u>AAGCTT</u>ACAACGGTTTCCCT (SEQ ID NO: 3) |
| EH SalI-r | TTATTGCT<u>GTCGAC</u>CAGTCATGCTAGCC (SEQ ID NO: 4) |
| Sequencing | |
| pCA24Nf-SH | GCCCTTTCGTCTTCACCTCG (SEQ ID NO: 5) |
| pCA24Nr-SH | GAACAAATCCAGATGGAGTTCTGAGGTCATT (SEQ ID NO: 6) |
| lasI-in-f | GCCCAGGTTTTCGGTTGCTGGCG (SEQ ID NO: 7) |
| rfp-lasR-P-f | CGCTAATCCCGCCAACGGGCCAATG (SEQ ID NO: 7) |
| EH-in-f | GTACTCGCAATTCCATCAAC (SEQ ID NO: 8) | glass bottom dishes in M9G for 24 h at 37° C. without shaking. Overnight cultures of *P. aeruginosa* were added into the dishes at an initial turbidity at 600 nm of 0.1, and 15 mM of arginine and 1% arabinose were added to the culture. The dishes were incubated for another 24 h at 37° C.

Confocal microscopy images were taken using a 63×/1.4 oil objective lens (HCX PL APO CS 63.0×1.4 OIL UV) with a TCS SP5 scanning confocal laser microscope (Leica Microsystem, Wetzlar, Germany). Using the confocal z-stack images, 3-D reconstruction of the biofilm architecture was performed using IMARIS software (Bitplane Inc., CT, USA). Biomass was obtained using COMSTAT image-processing software[50]. At least 3 different areas were observed, and average biomass was reported. At least 3 independent cultures were tested in this manner, and representative images are shown. Confocal images were obtained using an argon laser with emission set between ~500 to 540 nm in one photomultiplier tube (green channel) and emission set between ~550 to 650 nm in the other photomultiplier tube (red channel). A double dichoric lens was used to filter emitted light to visualize RFP and a triple dichoric lens was used to filter emitted light to observe both RFP and GFP.

NO assay. The final products of NO produced in vivo are nitrite and nitrate; thus, the sum of the nitrite and nitrate concentrations is directly correlated to the level of NO production[21]. Nitrate and nitrite concentrations were measured using a nitrate/nitrite colorimetric assay kit (Cayman Chemicals). Diluted overnight cultures at an initial turbidity at 600 nm of 0.05 were inoculated into M9G for 48 h at 37° C. Arginine 15 mM was added as the substrate, and 1% arabinose was added to induce NO production. At least 3 independent cultures were tested.

EH Assay. A chromogenic reaction of epoxide epichlorohydrin with 4-nitrobenzylpyridine was used to measure the activity of EH[51] using planktonic cells. The assay was performed in 1.5 mL microcentrifuge tubes as described previously[28]. Diluted overnight cultures at an initial turbidity at 600 nm of 0.05 were inoculated in LB with 1% arabinose at 37° C. The culture (100 µL) at an initial turbidity at 600 nm of 1 was contacted with 400 µL of 5 mM epichlorohydrin in TE buffer (pH 9.0) at 37° C., then 250 µL of 4-nitrobenzylpyridine (100 mM in 80 vol % ethylene glycol and 20 vol % acetone) was added. After heating the samples at 80° C. for 10 min, 250 µL of 50% trimethylamine (in acetone) was added. The samples were measured at 520 nm. At least 3 independent cultures were tested. The protein content of *E. coli* TG1[52] (0.22 mg of protein/mL/OD) was used to calculate the epichlorohydrin degradation rate.

Membrane Biofilms. Biofilms were grown on membranes for 24 h in M9G in a VWR gravity convection incubator (Radnor, Pa., USA). The membrane used was the commercially available DOW NF90 thin film composite polyamide type. An Advantec MFS UHP-76 (Dublin, Calif., USA) stirred cell with effective membrane area of 35.3 cm$^2$ was used for growing biofilms on membranes as well as for conducting permeability tests. A flat sheet of the NF90 membrane was placed under the O-ring and above the spacer of the stirred cell. The inner volume (450 mL) of the stirred cell was sterilized with 95% ethanol, and cells were adjusted to a turbidity of 0.5 at 600 nm in M9G medium. The cells were added to the stirred cell to a total liquid volume of 300 mL and grown without stirring for 24 h to form the biofilm. Small pieces of the membranes (~5×5 mm) were utilized for confocal laser scanning microscopy.

Consortial Biofilms. To challenge the beneficial biofilm with *P. aeruginosa* PAO1/pMRP9-1 and to ascertain the dispersal activity of the beneficial strain, both the NO-control strain, *E. coli* TG1/pBdcAE50Q-lasI-lasR/pBad, and the *E. coli* NO+ beneficial strain (*E. coli* TG1/pBdcAE50Q-lasI-lasR/pBNos) were grown as biofilms on NF90 membranes for 24 h as described above. The medium was discarded and replaced with fresh M9G medium (300 mL) containing 15 mM L-arginine (substrate for NO synthase) and 1.6% L-arabinose inducer for bNos. An overnight culture of *P. aeruginosa* in LB with 1.6% arabinose and 15 mM of arginine was added to each stirred cell to make an initial turbidity of 0.1 at 600 nm. The stirred cells were incubated for 24 h. Small sections of the membranes from different regions were imaged for biofilms under confocal microscopy using combined green and red fluorescence lasers. At least 15 different membrane biofilm samples, spanning 3 independent cultures, were analyzed to get average biofilm thickness and biomass.

RO Flux Assay. Flux experiments were performed immediately following biofilm growth using 0, 5, 10, and 15 mM NaCl. After removing the medium, the stirred cell was washed three times with 15 mM NaCl, and the stirrer and sample withdrawal tubes were loaded into the cells. Simultaneously, solutions of 25% feed NaCl concentrations were loaded into the 1 L Amicon reservoir (EMD Millipore, Billerica, Mass., USA). In this way, any variation of feed concentration during the flux experiment in the dead-end filtration mode was minimized. The reservoir NaCl concentrations were 0, 1.25, 2.5, and 3.75 mM. Thereafter, the reservoir and the stirred cell were pressurized to 50 psi using N2, and the stirring speed was maintained at 400 rpm. Permeate water weight was collected every 30 seconds using an automated A&D FX-300i balance (Bradford, Mass., USA) and analyzed using WinCT RS Weight software (V 3.00). The experiments were continued for 20-30 minutes for each feed concentration. Conductivities of permeate and feed were measured using an Orion Versastar conductivity meter (model VSTAR 50) from Thermo Scientific. The measured flux in grams/min was converted into LMH (liter/m$^2$/h) for membrane performance comparison.

Long-Term Crossflow Filtration Biofilm Challenge Experiments. Biofilm Development under crossflow conditions were performed according to Herzberg and Elimelech (2007) Biofouling of reverse osmosis membranes: Role of biofilm-enhanced osmotic pressure. *J Membrane Sci* 295 (1-2):11-20. with some modifications. A 0.5% bleach solution was circulated through the crossflow RO system built around an Osmonics SEPA® cell (Sterilitech, Kent, Wash.) for 2 h in recirculation mode to disinfect the system. Following disinfection, deionized (DI) water was introduced in flushing mode to rinse the system for 10 min and then trace organic matter was removed with 5 mM EDTA at pH ~11 (1 mM NaOH) under recirculation mode for 30 minutes. The unit was rinsed again with DI water for 30 minutes in flushing mode, and 95% ethanol was recirculated through the system for 1 h for further sterilization. Autoclaved DI water was then introduced to flush the system of residual ethanol. An ethanol-sterilized and autoclaved water-washed NF90 membrane was then loaded in the system along with a feed spacer (as indicated) and membrane compaction was performed overnight with autoclaved DI water with the temperature adjusted to 27° C. at 200 psi. Four liters of M9G media was introduced with 300 µg/mL chloramphenicol (Cm)

and 250 µg/mL carbenicillin (Cb) without arginine/arabinose, and the membrane was conditioned for 4 h at 27° C. at 200 psi. Centrifuged *E. coli* NO− or *E. coli* NO+ cells (5000 rpm for 10 minutes at 4° C.) from overnight cultures were added to the 4 L M9G media to an initial turbidity at 600 nm of 0.01 or 0.05. The *E. coli*. biofilms on the membranes were developed for 24 hr at ~40 psi at 27° C. in recirculation crossflow without any filtration. The feed solution was then removed, the system was flushed with fresh 4 L M9G medium, and centrifuged *P. aeruginosa* PAO1 cells (5000 rpm for 10 minutes at 4° C.) from overnight cultures were added to another freshly prepared 4 L M9G with 300 µg/mL chloramphenicol (Cm) and 250 µg/mL carbenicillin (Cb) supplemented with 15 mM L-arginine and 1.6% L-arabinose at an initial turbidity of 0.002 or 0.01. The challenge experiment was continued for ~72 to 96 h (depending on system stability) at ~200 psi at 27° C. with collection of flux data. After the completion of the experiments, the membranes were collected in 0.85% sterile NaCl solution and immediate confocal microscopy analysis was performed on different sections of the membrane.

EH Assay Via Once-Through RO. *E. coli* TG1/pBdcAE50Q-lasI-lasR/pBNos-echA and control (*E. coli* TG1/pBdcAE50Q-lasI-lasR/pBNos) biofilms were grown on NF90 membranes using M9G supplemented with 15 mM L-arginine (substrate for NO synthase) and 1.6% L-arabinose (inducer of bNos) under static conditions for 24 h. The medium was removed from the stirred cell, and the biofilm was challenged with 10 mM epichlorohydrin in 5 mM NaCl solution with the pH adjusted to $9^{28}$ to maintain a constant pH throughout the experiment and analysis and thus minimizing unwanted dissociation. After incubating 5 min, the RO system was pressurized to 50 psi via $N_2$, permeate samples between 10 to 20 minutes and between 20 to 30 minutes were collected, and 100 pt samples were used for the EH assay.

1. Barnes, R. J. et al. Optimal dosing regimen of nitric oxide donor compounds for the reduction of *Pseudomonas aeruginosa* biofilm and isolates from wastewater membranes. *Biofouling* 29, 203-212 (2013).
2. Baroni, L., Cenci, L., Tettamanti, M. & Berati, M. Evaluating the environmental impact of various dietary patterns combined with different food production systems. *Eur J Clin Nutr* 61, 279-286 (2007).
3. Shannon, M. A. et al. Science and technology for water purification in the coming decades. *Nature* 452, 301-310 (2008).
4. Greenlee, L. F., Lawler, D. F., Freeman, B. D., Marrot, B. & Moulin, P. Reverse osmosis desalination: Water sources, technology, and today's challenges. *Water Res* 43, 2317-2348 (2009).
5. Matin, A., Khan, Z., Zaidi, S. M. J. & Boyce, M. C. Biofouling in reverse osmosis membranes for seawater desalination: Phenomena and prevention. *Desalination* 281, 1-16 (2011).
6. Shrout, J. D. & Nerenberg, R. Monitoring bacterial twitter: Does quorum sensing determine the behavior of water and wastewater treatment biofilms? *Environ Sci Technol* 46, 1995-2005 (2012).
7. Siddiqui, M. F., Sakinah, M., Singh, L. & Zularisam, A. W. Targeting N-acyl-homoserine-lactones to mitigate membrane biofouling based on quorum sensing using a biofouling reducer. *J Biotechnol* 161, 190-197 (2012).
8. Yang, H. L., Lin, J. C. T. & Huang, C. Application of nanosilver surface modification to RO membrane and spacer for mitigating biofouling in seawater desalination. *Water Res* 43, 3777-3786 (2009).
9. Ghayeni, S. B. S., Beatson, P. J., Schneider, R. P. & Fane, A. G. Adhesion of waste water bacteria to reverse osmosis membranes. *J Membrane Sci* 138, 29-42 (1998).
10. Barnes, R. J. et al. The roles of *Pseudomonas aeruginosa* extracellular polysaccharides in biofouling of reverse osmosis membranes and nitric oxide induced dispersal. *J Membrane Sci* 466, 161-172 (2014).
11. Hong, S. H. et al. Synthetic quorum-sensing circuit to control consortial biofilm formation and dispersal in a microfluidic device. *Nat Commun* 3, 613 (2012).
12. Williams, P. & Camara, M. Quorum sensing and environmental adaptation in *Pseudomonas aeruginosa*: a tale of regulatory networks and multifunctional signal molecules. *Curr Opin Microbiol* 12, 182-191 (2009).
13. Kaplan, J. B. Biofilm dispersal: mechanisms, clinical Implications, and potential therapeutic uses. *J Dent Res* 89, 205-218 (2010).
14. Davies, D. G. & Marques, C. N. H. A fatty acid messenger is responsible for inducing dispersion in microbial biofilms. *J. Bacteriol.* 191, 1393-1403 (2009).
15. Barraud, N. et al. Nitric oxide-mediated dispersal in single- and multi-species biofilms of clinically and industrially relevant microorganisms. *Microb Biotechnol* 2, 370-378 (2009).
16. Nakhamchik, A., Wilde, C. & Rowe-Magnus, D. A. Cyclic-di-GMP regulates extracellular polysaccharide production, biofilm formation, and rugose colony development by *Vibrio vulnificus*. *Appl Environ Microbiol* 74, 4199-4209 (2008).
17. Kulesekara, H. et al. Analysis of *Pseudomonas aeruginosa* diguanylate cyclases and phosphodiesterases reveals a role for bis-(3 '-5')-cyclic-GMP in virulence. *Proc Natl Acad Sci USA* 103, 2839-2844 (2006).
18. Ross, P. et al. The cyclic diguanylic acid regulatory system of cellulose synthesis in *Acetobacter xylinum*. Chemical synthesis and biological activity of cyclic nucleotide dimer, trimer, and phosphothioate derivatives. *J Biol Chem* 265, 18933-18943 (1990).
19. Lee, V. T. et al. A cyclic-di-GMP receptor required for bacterial exopolysaccharide production. *Mol Microbiol* 65, 1474-1484 (2007).
20. Barraud, N. et al. Nitric oxide signaling in *Pseudomonas aeruginosa* biofilms mediates phosphodiesterase activity, decreased cyclic di-GMP levels, and enhanced dispersal. *J Bacteriol* 191, 7333-7342 (2009).
21. Gusarov, I. et al. Bacterial nitric-oxide synthases operate without a dedicated redox partner. *J Biol Chem* 283, 13140-13147 (2008).
22. Rossi, A. M., Migliore, L., Loprieno, N., Romano, M. & Salmona, M. Evaluation of epichlorohydrin (ECH) genotoxicity. Microsomal epoxide hydrolase-dependent deactivation of ECH mutagenicity in *Schizosaccharomyces pombe* in vitro. *Mutat Res* 109, 41-52 (1983).
23. Krijgsheld, K. R. & Vandergen, A. Assessment of the impact of the emission of certain organochlorine compounds on the aquatic environment 0.3. Epichlorohydrin. *Chemosphere* 15, 881-893 (1986).
24. Buser, H. R., Muller, M. D., Buerge, I. J. & Poiger, T. Composition of Aldrin, Dieldrin, and Photodieldrin Enantiomers in Technical and Environmental Samples. *J Agric Food Chem* 57, 7445-7452 (2009).
25. Eichelbe, J. W. & Lichtenb, J. J. Persistence of pesticides in river water. *Environ Sci* Technol 5, 541-& (1971).

26. Decker, M., Arand, M. & Cronin, A. Mammalian epoxide hydrolases in xenobiotic metabolism and signalling. *Arch Toxicol* 83, 297-318 (2009).
27. Jacobs, M. H. J., Vandenwijngaard, A. J., Pentenga, M. & Janssen, D. B. Characterization of the Epoxide Hydrolase from an Epichlorohydrin-Degrading *Pseudomonas* sp. *Eur J Biochem* 202, 1217-1222 (1991).
28. Rui, L. Y., Cao, L., Chen, W., Reardon, K. F. & Wood, T. K. Active site engineering of the epoxide hydrolase from *Agrobacterium radiobacter* AD1 to enhance aerobic mineralization of cis-1,2-dichloroethylene in cells expressing an evolved toluene ortho-monooxygenase. *J Biol Chem* 279, 46810-46817 (2004).
29. Pesci, E. C., Pearson, J. P., Seed, P. C. & Iglewski, B. H. Regulation of las and rhl quorum sensing in *Pseudomonas aeruginosa*. *J Bacteriol* 179, 3127-3132 (1997).
30. Ma, Q., Yang, Z. H., Pu, M. M., Peti, W. G. & Wood, T. K. Engineering a novel c-di-GMP-binding protein for biofilm dispersal. *Environ Microbiol* 13, 631-642 (2011).
31. Hong, S. H. et al. Synthetic quorum-sensing circuit to control consortial biofilm formation and dispersal in a microfluidic device. *Nat Commun* 3, 613 (2012).
32. Kim, S. et al. Biofouling of reverse osmosis membranes: Microbial quorum sensing and fouling propensity. *Desalination* 247, 303-315 (2009).
33. Steinle-Darling, E., Zedda, M., Plumlee, M. H., Ridgway, H. F. & Reinhard, M. Evaluating the impacts of membrane type, coating, fouling, chemical properties and water chemistry on reverse osmosis rejection of seven nitrosoalklyamines, including NDMA. *Water Res* 41, 3959-3967 (2007).
34. Zenker, M. J., Borden, R. C. & Barlaz, M. A. Occurrence and treatment of 1,4-dioxane in aqueous environments. *Environ Eng Sci* 20, 423-432 (2003).
35. Plumlee, M. H., Lopez-Mesas, M., Heidlberger, A., Ishida, K. P. & Reinhard, M. N-nitrosodimethylamine (NDMA) removal by reverse osmosis and UV treatment and analysis via LC-MS/MS. *Water Res* 42, 347-355 (2008).
36. Fraser, D. W. et al. Legionnaires Disease—Description of an Epidemic of Pneumonia. *New Engl J Med* 297, 1189-1197 (1977).
37. Best, M. et al. Legionellaceae in the Hospital Water-Supply—Epidemiological Link with Disease and Evaluation of a Method for Control of Nosocomial Legionnaires-Disease and Pittsburgh Pneumonia. *Lancet* 2, 307-310 (1983).
38. Nickel, J. C., Ruseska, I., Wright, J. B. & Costerton, J. W. Tobramycin resistance of *Pseudomonas aeruginosa* cells growing as a biofilm on urinary catheter material. *Antimicrobial agents and chemotherapy* 27, 619-624 (1985).
39. Douglas, L. J. *Candida* biofilms and their role in infection. *Trends Microbiol* 11, 30-36 (2003).
40. Costerton, J. W., Stewart, P. S. & Greenberg, E. P. Bacterial biofilms: A common cause of persistent infections. *Science* 284, 1318-1322 (1999).
41. Singh, P. K. et al. Quorum-sensing signals indicate that cystic fibrosis lungs are infected with bacterial biofilms. *Nature* 407, 762-764 (2000).
42. Hyde, J. A. J., Darouiche, R. O. & Costerton, J. W. Strategies for prophylaxis against prosthetic valve endocarditis: A review article. *J Heart Valve Dis* 7, 316-326 (1998).
43. Sbordone, L. & Bortolaia, C. Oral microbial biofilms and plaque-related diseases: microbial communities and their role in the shift from oral health to disease. *Clin Oral Invest* 7, 181-188 (2003).
44. Cryer, J., Schipor, I., Perloff, J. R. & Palmer, J. N. Evidence of bacterial biofilms in human chronic sinusitis. *Orl J Oto-Rhino-Lary* 66, 155-158 (2004).
45. Malfertheiner, P., Link, A. & Selgrad, M. *Helicobacter pylori*: perspectives and time trends. *Nat Rev Gastro Hepat* 11, 628-638 (2014).
46. Yonezawa, H. et al. Impact of *Helicobacter pylori* Biofilm Formation on Clarithromycin Susceptibility and Generation of Resistance Mutations. *PloS one* 8 (2013).
47. Sambrook, J. F. & Russell, D. W. Molecular cloning: a laboratory manual, Edn. 3rd. (Cold Spring Harbor Laboratory Press, New York; 2001).
48. Sambrook, J., Fritsch, E. F. & Maniatis, T. Molecular Cloning, *A Laboratory Manual*, Edn. 2. (Cold Spring Harbor Laboratory Press, Cold Spring Harbor, N.Y.; 1989).
49. Fletcher, M. The effects of culture concentration and age, time, and temperature on bacterial attachment to polystyrene. *Can J Microbiol* 23, 1-6 (1977).
50. Heydorn, A. et al. Quantification of biofilm structures by the novel computer program COMSTAT. *Microbiology* 146 (Pt 10), 2395-2407 (2000).
51. Rink, R., Fennema, M., Smids, M., Dehmel, U. & Janssen, D. B. Primary structure and catalytic mechanism of the epoxide hydrolase from *Agrobacterium radiobacter* AD1. *J Biol Chem* 272, 14650-14657 (1997).
52. Leungsakul, T., Johnson, G. R. & Wood, T. K. Protein engineering of the 4-methyl-5-nitrocatechol monooxygenase from *Burkholderia* sp. strain DNT for enhanced degradation of nitroaromatics. *Appl Environ Microbiol* 72, 3933-3939 (2006).
53. Jacobs, M. A. et al. Comprehensive transposon mutant library of *Pseudomonas aeruginosa*. *Proc Natl Acad Sci USA* 100, 14339-14344 (2003).
54. Davies, D. G. et al. The involvement of cell-to-cell signals in the development of a bacterial biofilm. *Science* 280, 295-298 (1998).

What is claimed is:

1. A method of producing a living self-controlled biofilm of engineered bacteria cells on a surface, said method comprising:
   a) producing at least one engineered bacteria cell by introducing into said at least one bacteria cell a quorum sensing nucleic acid construct, comprising,
      i. a nucleic acid molecule encoding an autoinducer synthase polypeptide comprising LasI;
      ii. a nucleic acid molecule encoding a transcriptional regulator comprising LasR capable of being activated by said autoinducer synthase polypeptide; and
      iii. a nucleic acid molecule encoding a biofilm dispersal protein comprising BdcA to produce said at least one engineered bacteria cell comprising said construct; and
   b) producing a self-controlled biofilm of said at least one engineered bacteria cells, wherein said quorum sensing nucleic acid construct in response to activation of said transcriptional regulator and production of said biofilm dispersal protein reduces the thickness of said self-controlled biofilm compared to biofilm not comprising said quorum sensing nucleic acid construct.

2. The method of claim 1, further comprising introducing into said at least one bacteria cell a nucleic acid molecule encoding nitric oxide synthase.

3. The method of claim 1, further comprising introducing into said bacteria a nucleic acid molecule encoding epoxide hydrolase.

4. The method of claim 1, wherein said thickness of said biofilm is at least six fold less than said biofilm not comprising said quorum sensing nucleic acid construct.

5. The method of claim 1, wherein said surface comprises a reverse osmosis membrane.

6. The method of claim 1, wherein said at least one bacteria cell comprises a gram negative bacteria cell.

7. A living self-controlled biofilm of engineered bacteria, said engineered bacteria comprising a nucleic acid construct comprising:
   a) a nucleic acid molecule encoding an auto inducer synthase polypeptide comprising LasI;
   b) a nucleic acid molecule encoding a transcriptional regulator comprising LasR, capable of being activated by said auto inducer synthase polypeptide; and
   c) a nucleic acid molecule encoding a biofilm dispersal protein comprising BdcA to produce engineered bacteria comprising said construct and producing a self-controlled biofilm of said engineered bacteria.

8. The biofilm of claim 7, further comprising a nucleic acid molecule encoding nitric oxide synthase.

9. The biofilm of claim 7, further comprising a nucleic acid molecule encoding epoxide hydrolase.

10. The biofilm of claim 7, further comprising a nucleic acid molecule encoding nitric oxide synthase and a nucleic acid molecule encoding epoxide hydrolase.

* * * * *

SEQUENCE LISTING

<160> NUMBER OF SEQ ID NOS: 9

<210> SEQ ID NO 1
<211> LENGTH: 28
<212> TYPE: DNA
<213> ORGANISM: Artificial Sequence
<220> FEATURE:
<223> OTHER INFORMATION: lasI-SalI- Forward primer

<400> SEQUENCE: 1
gctgagcttc ttcagtcgac tatttgga

<210> SEQ ID NO 2
<211> LENGTH: 31
<212> TYPE: DNA
<213> ORGANISM: Artificial Sequence
<220> FEATURE:
<223> OTHER INFORMATION: lasI-HindIII- Reverse Primer

<400> SEQUENCE: 2
aagctcagca aagcttcgtc atgaaaccgc c                                31

<210> SEQ ID NO 3
<211> LENGTH: 25
<212> TYPE: DNA
<213> ORGANISM: Artificial Sequence
<220> FEATURE:
<223> OTHER INFORMATION: EH HindIII- Forward Primer

<400> SEQUENCE: 3
atagcaagct tacaacggtt tccct                                       25

<210> SEQ ID NO 4
<211> LENGTH: 28
<212> TYPE: DNA
<213> ORGANISM: Artificial Sequence
<220> FEATURE:
<223> OTHER INFORMATION: EH SalI- Reverse Primer

<400> SEQUENCE: 4
ttattgctgt cgaccagtca tgctagcc                                    28

<210> SEQ ID NO 5
<211> LENGTH: 20
<212> TYPE: DNA
<213> ORGANISM: Artificial Sequence
<220> FEATURE:
<223> OTHER INFORMATION: pCA24Nf-SH Sequencing Primer

<400> SEQUENCE: 5
gccctttcgt cttcacctcg                                             20

<210> SEQ ID NO 6
<211> LENGTH: 31
<212> TYPE: DNA
<213> ORGANISM: Artificial Sequence
<220> FEATURE:
<223> OTHER INFORMATION: pCA24Nr-SH Sequencing Primer

<400> SEQUENCE: 6
gaacaaatcc agatggagtt ctgaggtcat t                                31

<210> SEQ ID NO 7
<211> LENGTH: 23
<212> TYPE: DNA
<213> ORGANISM: Artificial Sequence
<220> FEATURE:
<223> OTHER INFORMATION: lasI-in-f Sequencing Primer

<400> SEQUENCE: 7
gcccaggttt tcggttgctg gcg                                         23

<210> SEQ ID NO 8
<211> LENGTH: 25
<212> TYPE: DNA
<213> ORGANISM: Artificial Sequence
<220> FEATURE:
<223> OTHER INFORMATION: rfp-lasR-P-f Sequencing Primer

```
<400> SEQUENCE: 8
cgctaatccc gccaacgggc caatg                                         25

<210> SEQ ID NO 9
<211> LENGTH: 20
<212> TYPE: DNA
<213> ORGANISM: Artificial Sequence
<220> FEATURE:
<223> OTHER INFORMATION: EH-in-f Sequencing Primer

<400> SEQUENCE: 9
gtactcgcaa ttccatcaac                                               20
```